(12) United States Patent
Khajavi et al.

(10) Patent No.: US 11,317,985 B2
(45) Date of Patent: May 3, 2022

(54) SAFETY-BLADE DISPENSER AND RELATED METHODS

(71) Applicant: STARTBOX, LLC, Atlanta, GA (US)

(72) Inventors: Kaveh Khajavi, Atlanta, GA (US); David E. Lane, II, Falkville, AL (US); Luke Boland, Englewood, CO (US); Christopher Davis, Arlington, VA (US); John G. Kerwood, Canton, GA (US)

(73) Assignee: STARTBOX, LLC, Atlanta, GA (US)

( * ) Notice: Subject to any disclaimer, the term of this patent is extended or adjusted under 35 U.S.C. 154(b) by 0 days.

(21) Appl. No.: 16/572,158

(22) Filed: Sep. 16, 2019

(65) Prior Publication Data

US 2020/0261177 A1    Aug. 20, 2020

Related U.S. Application Data

(63) Continuation of application No. 15/587,130, filed on May 4, 2017, now Pat. No. 10,413,378.
(Continued)

(51) Int. Cl.
*B65D 83/10* (2006.01)
*A61B 50/30* (2016.01)
(Continued)

(52) U.S. Cl.
CPC ...... *A61B 50/3001* (2016.02); *A61B 17/3215* (2013.01); *A61B 17/3217* (2013.01); *A61B 50/20* (2016.02); *A61B 50/362* (2016.02); *A61B 90/94* (2016.02); *A61B 90/96* (2016.02); *B65D 83/10* (2013.01); *A61B 17/3211* (2013.01); *A61B 2050/008* (2016.02);
(Continued)

(58) Field of Classification Search
None
See application file for complete search history.

(56) References Cited

U.S. PATENT DOCUMENTS

| 909,110 A | 1/1909 | O'Neil |
| 2,109,017 A | 2/1938 | Rodrigues |
| (Continued) | | |

FOREIGN PATENT DOCUMENTS

| WO | 2015103279 | 7/2015 |
| WO | 2017059452 | 4/2017 |

OTHER PUBLICATIONS

International Search Report and Written Opinion issued for International Application No. PCT/US2016/055210, dated Mar. 13, 2017.

*Primary Examiner* — Gene O Crawford
*Assistant Examiner* — Ayodeji T Ojofeitimi
(74) *Attorney, Agent, or Firm* — Meunier Carlin & Curfman LLC

(57) ABSTRACT

Safety-blade dispensers for safely storing surgical blades prior to surgery and optionally for retrieving used surgical blades after surgery. In either case, the safety-blade dispenser is configured to store one or more surgical blades in an orientation that allows a user to simply and safely attach a surgical tool handle to the surgical blades (and optionally remove the handle from the surgical blades) without requiring the user to physically touch or manipulate the surgical blades by hand. The safety-blade dispensers disclosed herein may be used alone or in conjunction with a system and method of preventing wrong-site surgery.

20 Claims, 74 Drawing Sheets

Related U.S. Application Data

(60) Provisional application No. 62/331,790, filed on May 4, 2016, provisional application No. 62/331,819, filed on May 4, 2016, provisional application No. 62/332,330, filed on May 5, 2016.

(51) Int. Cl.

| | | |
|---|---|---|
| *A61B 50/20* | (2016.01) | |
| *A61B 50/36* | (2016.01) | |
| *A61B 90/94* | (2016.01) | |
| *A61B 90/96* | (2016.01) | |
| *A61B 17/3215* | (2006.01) | |
| *A61B 17/3217* | (2006.01) | |
| *A61B 17/3211* | (2006.01) | |
| *A61B 50/00* | (2016.01) | |
| *A61B 90/00* | (2016.01) | |

(52) U.S. Cl.
CPC .  *A61B 2050/0059* (2016.02); *A61B 2050/314* (2016.02); *A61B 2090/0807* (2016.02)

(56) References Cited

U.S. PATENT DOCUMENTS

| | | | |
|---|---|---|---|
| 2,624,453 A | 1/1953 | Muros | |
| 2,653,704 A | 9/1953 | Nelson | |
| 3,080,998 A | 3/1963 | La Cas | |
| 3,093,266 A | 6/1963 | Kuhnl | |
| 3,244,317 A | 4/1966 | Raybin | |
| 3,460,712 A * | 8/1969 | Lowry | B26B 21/24 221/102 |
| 3,542,245 A | 11/1970 | Braginetz | |
| 3,848,770 A | 11/1974 | Iten | |
| 3,910,455 A | 10/1975 | Ferraro | |
| 4,106,620 A | 8/1978 | Brimmer et al. | |
| 4,395,807 A | 8/1983 | Eldridge, Jr. | |
| 4,826,042 A | 5/1989 | Vujovich | |
| 4,850,512 A | 7/1989 | Vujovich | |
| 4,903,390 A | 2/1990 | Vidal | |
| 5,088,173 A | 2/1992 | Kromer | |
| 5,181,609 A | 1/1993 | Spielmann | |
| 5,251,783 A | 10/1993 | Gringer | |
| 5,257,692 A | 11/1993 | Heacox | |
| 5,662,221 A | 9/1997 | Abidin | |
| 5,727,682 A | 3/1998 | Abidin | |
| 5,875,532 A | 3/1999 | Musgrave | |
| 5,894,925 A | 4/1999 | Sukiennik | |
| 5,938,027 A | 8/1999 | Soroff | |
| 6,158,616 A | 12/2000 | Huang | |
| 6,216,868 B1 | 4/2001 | Rastegar | |
| 6,874,629 B1 | 4/2005 | Wortrich | |
| 7,398,880 B2 | 7/2008 | Henry | |
| 10,413,378 B2 * | 9/2019 | Khajavi | A61B 17/3217 |
| 2004/0178214 A1 | 9/2004 | Wei | |
| 2007/0039844 A1 | 2/2007 | Zyzelewski | |
| 2009/0018864 A1 | 1/2009 | Gecelter | |
| 2010/0170913 A1 | 7/2010 | Shoshani | |
| 2011/0015938 A1 | 9/2011 | Rabinowitz | |
| 2011/0233229 A1 | 9/2011 | Schekalla | |
| 2013/0126550 A1 | 5/2013 | Schneider | |
| 2013/0159015 A1 | 6/2013 | O'Con | |
| 2014/0034665 A1 | 2/2014 | Walter | |
| 2014/0110298 A1 | 4/2014 | Khajavi | |
| 2014/0263393 A1 | 9/2014 | Garavaglia | |
| 2016/0304269 A1 | 10/2016 | Erdmann | |
| 2017/0174412 A1 | 6/2017 | Wonderley | |

\* cited by examiner

| | |
|---|---|
| TOTAL SURGICAL PROCEDURES | 252 |
| SURGICAL PROCEDURES WITH SEV-2 NEAR-MISS DATA | 24 |
| SURGICAL PROCEDURES WITH SEV-1 NEAR MISS DATA | 3 |
| TOTAL SUCCESSFUL SURGICAL PROCEDURES | 252 |

SAFETY-BLADE DISPENSER AND RELATED METHODS

CROSS-REFERENCES TO RELATED APPLICATIONS

In accordance with 37 C.F.R. 1.76, a claim of priority is included in an Application Data Sheet filed concurrently herewith. The present application is a continuation of U.S. patent application Ser. No. 15/587,130 filed May 4, 2017 entitled "SAFETY-BLADE DISPENSER AND RELATED METHODS," which claims priority to U.S. Provisional Patent App. No. 62/331,790 filed May 4, 2016 entitled "SAFETY BLADE CONTAINER", U.S. Provisional Patent App. No. 62/332,330 filed May 5, 2016 entitled "SAFETY BLADE CONTAINER", and U.S. Provisional Patent App. No. 62/331,819 filed May 4, 2016 entitled "SYSTEM AND METHOD FOR PREVENTING WRONG-SITE SURGERIES." The contents of each of the above referenced applications are herein incorporated by reference in its entirety.

FIELD OF THE INVENTION

The present invention relates generally to surgery and, more specifically, safety blade containers for use in dispensing surgical blades for use in surgical procedures and optionally retrieving used surgical blades after surgical procedures, wherein the safety blade containers may be used as part of a system for preventing wrong-site surgeries.

BACKGROUND OF THE INVENTION

A persistent safety issue is that of needle-stick and other sharps-related injuries to OR personnel, including scalpel or blade-related injuries. The Center for Disease Control estimates that each year approximately 385,000 needle-stick and other sharps-related injuries (averaging over 1000 a day), of which blade-related injuries account for almost 10%. Scalpel blades are necessarily extremely sharp and, as a result, are more likely to penetrate the flesh of a surgeon or other OR personnel more deeply than needle-stick injuries. Blade-related injuries can therefore be monumental for OR personnel, including contracting diseases stemming from blood-borne pathogens such as HIV/AIDS, hepatitis-C, hepatitis-B, etc. . . . , as well as the loss of income during recovery and rehabilitation and the potential loss of occupation due to permanent physical injuries (e.g. to the hand of a surgeon).

Wrong-site surgeries are also a persistent problem within the healthcare system. As defined by the Joint Commission on Accreditation of Healthcare Organizations (JCAHO), wrong-site surgery includes wrong side or site of the body, wrong procedure, and wrong-patient surgeries. A multitude of factors have been identified that may contribute to an increased risk of wrong-site surgery. Despite the implementation of strategies to prevent wrong patient, wrong site, wrong side surgery, regrettably this seemingly most preventable of complications still occurs. The incorrect assumption of a medical professional's infallibility, coupled with organized medicine's focus on the individual's medical mistakes rather than a systems approach have contributed to this problem.

In an attempt to improve patient safety, compliance with the Universal Protocol for Preventing Wrong Site, Wrong Procedure, Wrong Person Surgery is required of all Joint Commission accredited organizations. As a part of the universal protocol, a "pause" or "time out" is required. This serves as a final verification of: (1) the correct patient; (2) the correct procedure, site and side; and as applicable, (3) the availability of implants or instrumentation, prior to making incision. This is a time when all members of the surgical team are supposed to pause to review the case, and agree that the correct procedure is being done on the correct patient, at the correct site, and on the correct side. In theory, this would ensure that any errors that had been made could be detected prior to incision. In reality, the "time out" seldom occurs; and when it does, not in any uniform or regular manner. Without a uniform or regular procedure, ritualized compliance, i.e. going through the motions, results in many institutions. The universal protocol cannot enforce a pause, and does not specify a protocol as to what should happen during a pause. The universal protocol does not specify a particular time for the pause to occur, and it does not specify a protocol as to what should happen during the pause; that is to say, what information should be communicated by whom, and to whom. While guidelines may be suggested, each institution determines how to comply, therefore standardization is not achieved.

The present invention is directed at addressing the unmet needs of preventing or reducing blade-related injuries to OR personnel, including doing so while also preventing or reducing wrong-site surgeries.

SUMMARY OF THE INVENTION

The present invention addresses the unmet needs described above by providing a variety of safety-blade dispensers suitable for use independently from or in conjunction with a system and method for preventing wrong-site surgeries such as that shown and described in commonly owned and co-pending International Patent Application PCT/US16/55210 (filed 3 Oct. 2016) entitled "System and Method for Preventing Wrong-Site Surgeries", published as WO2017-059452 on Apr. 6, 2017, the contents of which is hereby incorporated by reference as is set forth herein in its entirety ("the '210 PCT").

The system and method of the '210 PCT includes computer software system configured to provide a user with a method of preventing wrong site surgeries, in combination with any of the various safety blade-dispensers. The safety-blade dispensers can optionally include at least one component, such as a label, paper, or tape, which prevents or impedes a surgeon from accessing one or more surgical instruments stored within until after a "time-out" is performed by the surgeon or authorized OR personnel to confirm various details (e.g. correct patient, correct procedure, correct equipment, etc. . . . ) before starting the intended surgical procedure. The computer software system can be run on any of a variety of computing devices, such as a computer (e.g. stationary desktop and/or laptop) and/or a hand-held computing device (e.g. smart-phones such as IPHONE and/or a tablet device such as an IPAD or SURFACE PRO) used within the medical environment. The "medical environment" includes anywhere along the continuum in which patient and medical team (including the doctor, office personnel, nurses, medical technicians, surgeons, administrators) interact, from the surgeon's office (where the initial consultation and decision for surgery is made) to the operating room (where the surgery takes place). The term may also include personnel involved with post-surgical data collection and/or analysis, such as (but not limited to) (a) insurance companies for the patient, hospital and/or surgeon, (b) state and/or federal agency departments/programs (e.g. Medicare/Medicaid) which reimburse funds to the hospital and/or surgeon, (c) any other agency (private and/or governmental) which generates payment to the patient, hospital and/or surgeon for the specific surgical case, and/or (d) quality control and/or hospital administration to identify areas of improvement and/or best practices.

The system and related methods of preventing wrong-site surgeries and blade-related injuries utilize computer software system to support and provide several functionalities, including but not necessarily limited to voice recording, recording playback, an electronic patient-identifying component (such as a patient ID band) capable of being scanned, safety blade-dispenser capable of being scanned, and any of a variety of analytics generated or based upon data acquired through the use of the system from "decision-to-incision", that is, from the decision to have surgery (made in the surgeon's office) through the actual surgery (in the OR). Scanning of the patient ID band and/or safety blade-dispenser may be accomplished by scanning functionality of the computer, hand-held device and/or scanning systems separate from the system that cooperate and communicate with the system. The system may use any of a variety of suitable biometric identification technologies (e.g. iris scan, finger-prints, genetics, etc. . . . ) in order to identify the patient (and/or the guardian of the patient if the patient is a minor or incapacitated) at any point in the medical environment.

The safety blade-dispenser can include a variety of scalpel blades for the surgeon to select from in order to perform the first incision of the operation. The safety blade-dispenser (and/or label described below) can optionally be color-coded to indicate the laterality of the surgery (e.g. rose or red for "right" sided surgery, lavender for "left" sided surgery, and a neutral color (such as grey) for a surgery with no-laterality). The safety blade-dispenser can optionally include a label with a QR code capable of being scanned and linked with patient-data from the patient ID band via the software assembly to create a unique identifier for the particular safety-blade dispenser assigned to the patient during the pre-operative assessment in the hospital after admission on the day of surgery. This unique identifier ensures that the patient receives the correct type of blade-dispenser, meaning the correct laterality of the intended surgery, and can be tracked throughout the remainder of the medical environment and associated with any data captured throughout the entire medical environment to ensure it is correct and used to perform the intended surgery. The label can only be removed from the safety-dispenser after a timeout has been performed by the surgeon or authorized OR personnel. Once the label is removed, the surgeon then and only then has access to a variety of scalpel blades in the blade dispenser, the desired one of which can be safely advanced out of the dispenser for engagement to a handle such that the first incision can be made and the operation commenced.

The safety blade-dispenser can optionally be initially provided sealed in transparent double sterile packaging (which is then placed in a non-sterile container with a transparent window). The transparent packaging/window allows for the identifying information on the confirmation label (e.g. QR code and/or laterality indicator) to be scanned before the safety blade-dispenser is removed from any of the packaging. In this manner, one can avoid the need to have the same identifying information on multiple levels of the packaging. This reduces manufacturing costs and the complexity of matching multiple packaging components to ensure they all have the same identifying information, which would otherwise be required.

The system of preventing wrong-site surgeries and blade-related injuries allows for tracking of a variety of data from pre-hospitalization to the actual surgical procedure, which the software system can use to generate any of a variety of analytics. The analytics may be based upon, but not necessarily limited to, so-called "near miss" data (that is, errors that were caught and avoided during the use of the system), surgery type and laterality, surgical outcomes, surgical complications, patient demographics, geographic information, as well as the date, time, location and personnel associated with each interaction or use of the system for efficiency and accountability. For example, analytics based on "near miss" data may provide the hospital and/or insurers and/or quality improvement specialists valuable data as to where errors or possible errors may have occurred in order to drive remediation efforts to minimize or avoid such errors in the future. The analytics may also be used to identify best practices based on the data collected, either within the hospital system ("intra-system") and/or amongst multiple different hospital systems ("inter-system"), and assessed to identify best practices for further reducing wrong-site surgery errors.

Certain surgeries (including but not limited to spine surgery) can be performed at more than one level or location within a particular organ, structure or region of the patient's anatomy, which can create challenges for the surgeon to correctly identify the level of the intended surgery. According to one aspect of the disclosure, the system of preventing wrong-site surgeries and blade-related injuries may include a correct site verification process that extends beyond the "Timeout Recorded" step and may be performed before and/or after the time-out is conducted by the surgeon. More specifically, the software is capable of merging and comparing two images (e.g. a pre-op diagnostic image located in the hospital database and a radiographic image taken during surgery or a radiographic image taken during a prior surgery at the same or close surgical location) to determine if the intended site or level is correct.

The system of the present disclosure may include an additional feature regarding imaging the patient for the intended surgery. More specifically, the software system may allow the surgeon to specify that the patient undergo certain pre-surgical imaging (such as computed tomography (CT), positron emission tomography (PET, etc. . . . ) for use in the pre-surgical work-up or clearances as well as during the surgery. For example, the software may be configured such that the surgeon (during the "Decision" stage) may select or toggle a "Imaging Required" option, along with the ability to designate or describe the specific imaging he or she is requesting, which may be saved in the patient's electronic profile. If imaging is required, this information may be used by the surgery scheduler (at the Scheduling stage) to help schedule the requested imaging. The software may also include related functionality for use as the patient continues through the medical, such as (but not necessarily limited to) providing a selection or toggle an "Imaging Available" option wherein medical personnel (e.g. pre-op personnel) can check the system 10 to ensure the requested imaging is, in fact, available for use by the surgeon in the OR, as well as providing the surgeon the ability to review the imaging, if available, and optionally select or toggle a "Imaging Reviewed" option. Providing the ability for a surgeon to request and review imaging may help safeguard against the possibility that imaging read by other medical professionals (e.g. radiologists) may have been performed or documented inaccurately, which may cause inaccurate information to be in the patient profile. In this case, the surgeon can assess the imaging directly in the OR (or after admission) and determine if any such mistakes were made. If not, the surgery can continue. If so, the surgery can be stopped.

According to one aspect of the disclosure, a system for preventing or tracking a wrong-site error during a surgical procedure associated with an individual interacting within a medical environment is described. The system comprises a computer implemented electronic device having a screen for displaying images, a microphone for creating audio files, a speaker for playing recorded audio files, a processor operable to execute instructions, and a data storage medium for storing instructions which when executed by the processor cause the processor to save and display an electronic profile for an individual interacting within a medical environment, record and play audio files relating to the medical procedure, and enable an electronically recorded time out to be conducted prior to starting of the surgical procedure associated with the individual. The system further comprises a surgical supply carrier comprising one or more surgical instruments or components to be used during the surgical procedure for the individual, the surgical supply carrier including storage media comprising the electronic profile of the individual linked to identifying information of the surgical supply carrier such that a unique surgical carrier is associated with the patient.

The surgical supply carrier may have at least one component that prevents or impedes an individual from accessing the one or more surgical instruments or components stored therein.

The surgical supply carrier may be a safety blade dispenser comprising one or more surgical blades and is adapted to assist securing the one or more surgical blades to a surgical blade handle with minimal contact by a user.

The surgical supply carrier or electronic identifying component may be adapted to be secured to the individual interacting within a medical environment including a tracking mechanism.

The tracking mechanism may be an RFID tag.

The electronic profile of the individual may include one or more types of data that identifies the person, the medical procedure that is scheduled to be performed on the individual, and an indication of procedural laterality.

The indication of procedural laterality may include a color-based notation.

The audio information may include a notation describing what procedure is scheduled to be performed on the individual.

The instructions, when executed by the processor, may further cause the processor to display an analysis of transactions that occurred during a time period for which the individual interacted within said medical environment.

The analysis display may include wrong-site surgery near miss data, wrong-site surgery error data, or combinations thereof.

The computer implemented electronic device may be configured to include a decision input indication that the surgical procedure has stopped.

The processor may display data associated with the identification of the individual patient.

The processor may display information related to a surgical procedure associated with a patient.

The information related to a surgical procedure associated with a patient may include the surgical procedure required.

The information related to a surgical procedure associated with a patient may include information related to laterality of the surgical procedure required.

The information related to laterality of a the surgical procedure required may be a color coding specific for a left side surgery, a right side surgery, or a neutral surgery.

The computer implemented electronic device may include a camera.

The computer implemented electronic device may be configured to scan and interpret optical data.

The surgical supply carrier or electronic identifying component may contain optical data.

The optical data may be in the form of a bar code or QR code.

The computer implemented electronic device may be configured to read biometric data.

The biometric data may include fingerprint data, face recognition data, iris recognition data, retina scan data, DNA data, or combinations thereof.

The computer implemented electronic device may be configured to track and indicate which medical personnel performed a check on said individual as said individual travels within said medical environment.

According to another broad aspect of the disclosure, there is a method of preventing or tracking a wrong-site error during a surgical procedure associated with an individual interacting within a medical environment comprising the steps of: (a) using a computer implemented electronic device having a screen for displaying images, a microphone for recording audio files, a speaker for playing recorded audio files, a processor operable to execute instructions, and a data storage medium for storing instructions which when executed by the processor cause the processor to perform multiple functions which prevent or track wrong-site error associated with an individual interacting within a medical environment, said electronic device including an electronic patient profile comprising an audio message containing information relating to said individual, said information comprising at least the patient name or other identification information and a description of said surgical procedure; (b) assigning a surgical supply carrier to said individual based on information from said electronic patient profile, wherein the step of assigning includes linking said electronic profile of said individual to identifying information of said surgical supply carrier such that a unique surgical carrier is associated with said individual; (c) tracking said surgical supply carrier as said individual progresses throughout the medical environment to obtain and record data related to the interactions of said individual within said medical environment, including data regarding wrong site surgical error; and (d) enabling personnel within the medical environment to listen to the recorded audio message at multiple times as said individual engages with one or more personnel within said medical environment.

The method of preventing or tracking a wrong-site error during a surgical procedure associated with an individual interacting within a medical environment may further include the steps of: at a site prior to surgery, obtaining said surgical supply carrier and conducting a pre-surgery assessment by comparing information related to said individual with said information related to surgical supply carrier; and documenting said pre-surgery assessment by providing said computer implemented electronic device with a notation that the information associated with said individual was the same or different as the information associated with the surgical supply carrier.

The method of preventing or tracking a wrong-site error during a surgical procedure associated with an individual interacting within a medical environment may further include the steps of: at a site of surgery, obtaining said surgical supply carrier and conducting a surgery assessment by comparing information related to said individual with said information related to surgical supply carrier; and documenting said pre-surgery assessment by providing said computer implemented electronic device with a notation that the information associated with said individual was the same or different as the information associated with the surgical supply carrier.

The method of preventing or tracking a wrong-site error during a surgical procedure associated with an individual interacting within a medical environment may further include the steps of: performing a final time-out; and saving said final time-out in said a computer implemented electronic device.

The method of preventing or tracking a wrong-site error during a surgical procedure associated with an individual interacting within a medical environment may further including the steps of providing an analysis of transactions that occurred during a time period for which said individual interacted within said medical environment.

The analysis may include wrong-site surgery near miss data, wrong-site surgery error data, or combinations thereof.

According to another aspect, there is surgical sharps dispenser for use in a surgical procedure, comprising a generally rectangular housing unit sized and configured for holding in a single user's hand, the housing unit having a perimeter defined by first and second opposing faces, first and second opposing ends, and first and second opposing sides, the housing unit further including an interior cavity within the perimeter, the first end including at least one aperture formed therein and at least one sharps holder assembly adapted to releasably hold one surgical sharp, the at least one sharps holder assembly slideably positioned within said interior cavity and moveable between a first position in which a held surgical sharp is fully contained within said interior cavity to a second position in which a portion of said held surgical sharp protrudes through said aperture.

The first and second sides may include scalloped edges.

The surgical sharp may be a scalpel blade, said scalpel blade having a leading end comprising a blade portion and a trailing end comprising a connector portion.

The scalpel blade may be positioned within the sharps holder assembly such that the trailing end protrudes from the housing unit when the sharps holder assembly is in the second position.

The surgical sharp may be a scalpel, said scalpel having a leading end comprising a blade portion and a trailing end comprising a handle.

The scalpel may be positioned within said sharps holder assembly such that a portion of said handle protrudes from said housing unit when said sharps holder assembly is in said second position.

The at least one sharps holder assembly may comprise four sharps holder assemblies positioned side by side.

The surgical sharps dispenser may further include a confirmation label removably attached to the housing, the confirmation label positioned such that movement of the at least one sharps holder assembly is prevented while the confirmation label is attached to the housing.

A portion of the attached confirmation label may cover at least a portion of the first panel, a portion of the second panel, and the first end of the housing.

The confirmation label may include electronically scannable code, the electronically scannable code containing at least one of patient information and surgical procedure information.

The electronically scannable code may be one of a QR code and a bar code.

The attached confirmation label may include at least one visual indicator conveying to a user the laterality of the surgical procedure.

The at least one visual indicator may include at least one of words and color.

The surgical sharps dispenser may further include a packaging assembly adapted to receive the surgical sharps dispenser prior to the surgical procedure.

The packaging assembly may include a first transparent sterile pouch, a second transparent sterile pouch, and a non-sterile outer container.

The surgical sharps dispenser may be sealed within said first transparent sterile pouch, which is sealed within said second transparent sterile pouch, which is placed within said non-sterile outer container.

The outer container may include a transparent window.

The surgical sharps dispenser may be placed within said packaging assembly such that said electronically scannable code is scannable through said first transparent sterile pouch, said second transparent sterile pouch, and said transparent window while contained within said packaging assembly.

The safety-blade dispensers disclosed herein are configured to store one or more surgical blades in an orientation that allows a user to simply and safely attach a surgical tool handle to the surgical blades without the need for user intervention with his/her hands. The dispenser may include a lock mechanism for securing the container closed, and may contain an electronic tracking mechanism. In addition to dispensing blades in a safe manner, the safety-blade dispensers of the present application may also have an optional blade removal feature to enable the removal of the blade after the surgical procedure without any manual touching of the blade by a user. By eliminating the need for a user to manually touch or manipulate the blade from the blade handle, the likelihood for inadvertent blade or needle-stick injuries is effectively minimized or reduced.

Accordingly, it is an objective of the invention to provide a container for safely dispensing surgical blades for use in surgery and optionally safely removing surgical blades after surgery.

It is a further objective of the invention to provide a container for safely dispensing surgical blades for use in surgery and optionally safely removing surgical blades after surgery wherein the surgical blades are in an orientation that allows a user to simply and safely attach a surgical tool handle to the surgical blade and optionally remove the surgical blade from the surgical tool handle without the user touching the surgical blades with his/her hand.

It is a further objective of the invention to provide any of a variety of safety-blade dispensers for use in systems and methods for preventing wrong-site surgeries with the ability to consistently produce, capture, and store reliable and mineable wrong site surgery data, electronic wrong site surgery near miss data, electronic wrong site surgery error data and/or an electronic patient surgical profile.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
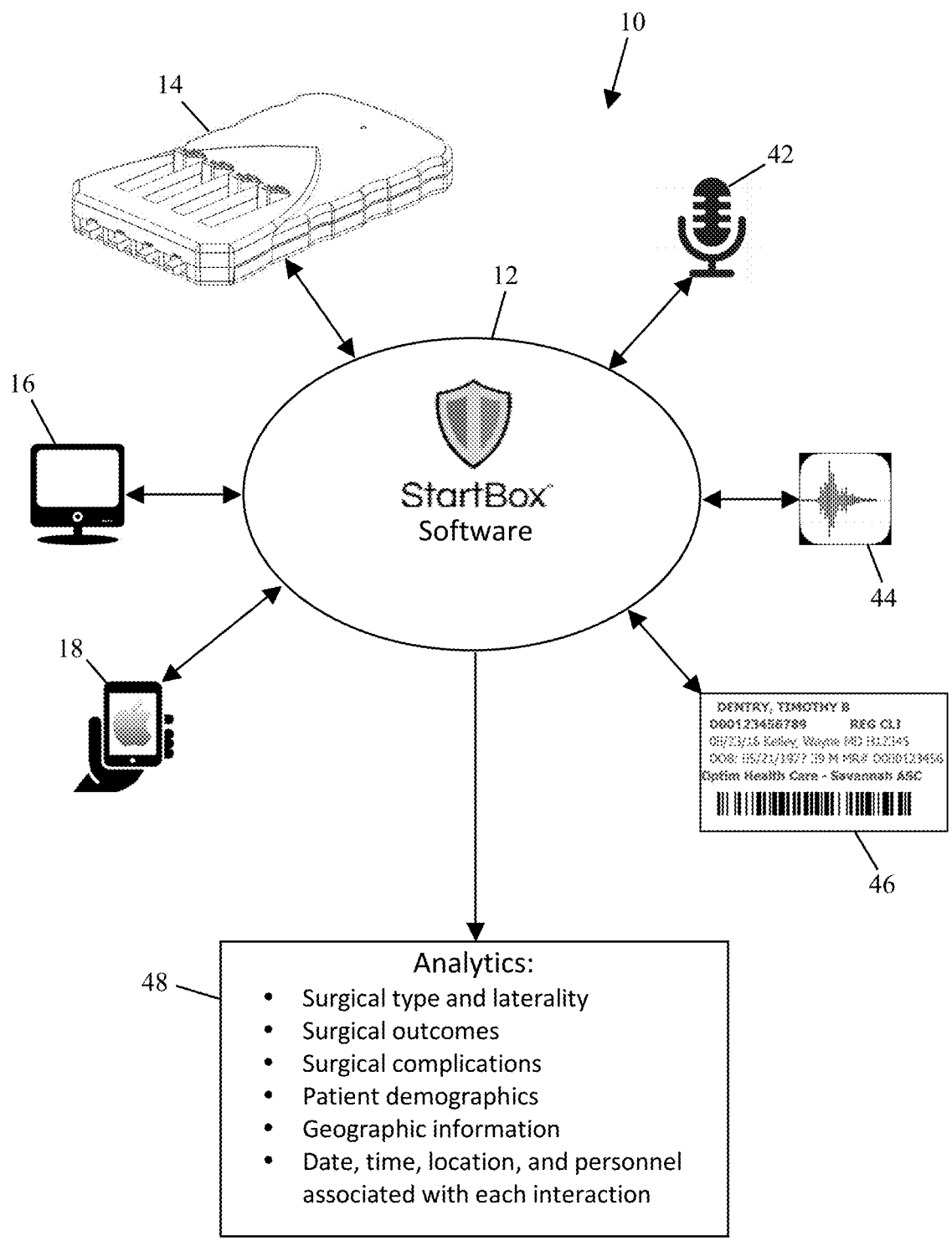
FIG. 1 is a graphical representation of an exemplary wrong-site surgery prevention system which may include any of the various safety-blade dispensers of the present disclosure.
Figure 2:
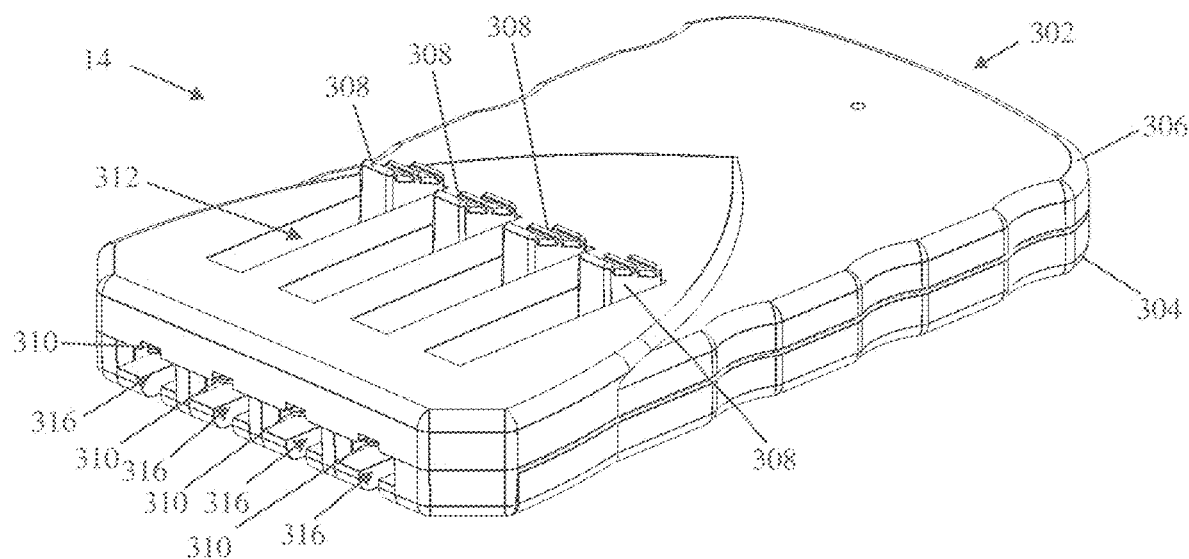
FIG. 2 is a perspective view of one example of the safety blade-dispenser of FIG. 1.
Figure 3:
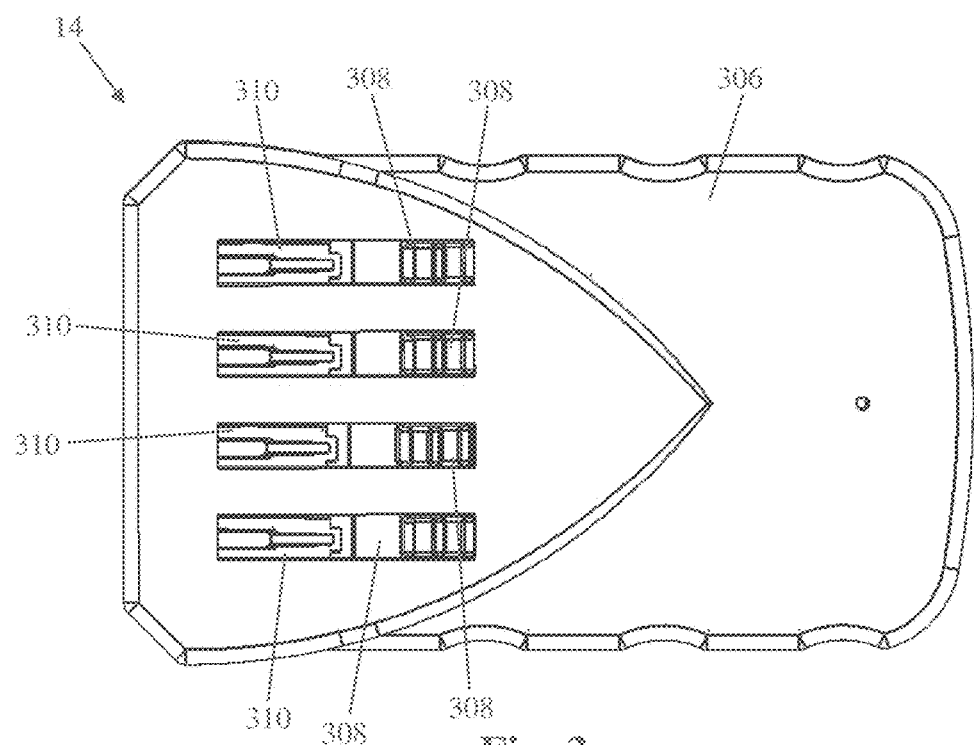
FIG. 3 is a top plan view of the safety blade-dispenser of FIG. 2.
Figure 4:
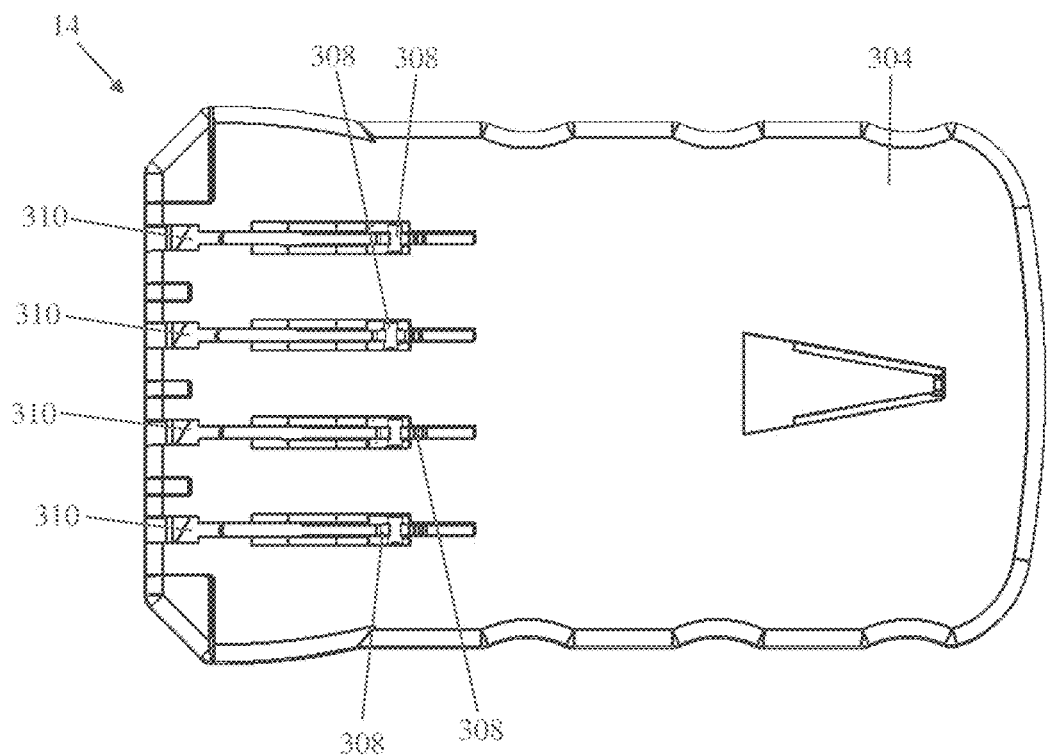
FIG. 4 is a bottom plan view of the safety blade-dispenser of FIG. 2.
Figure 5:
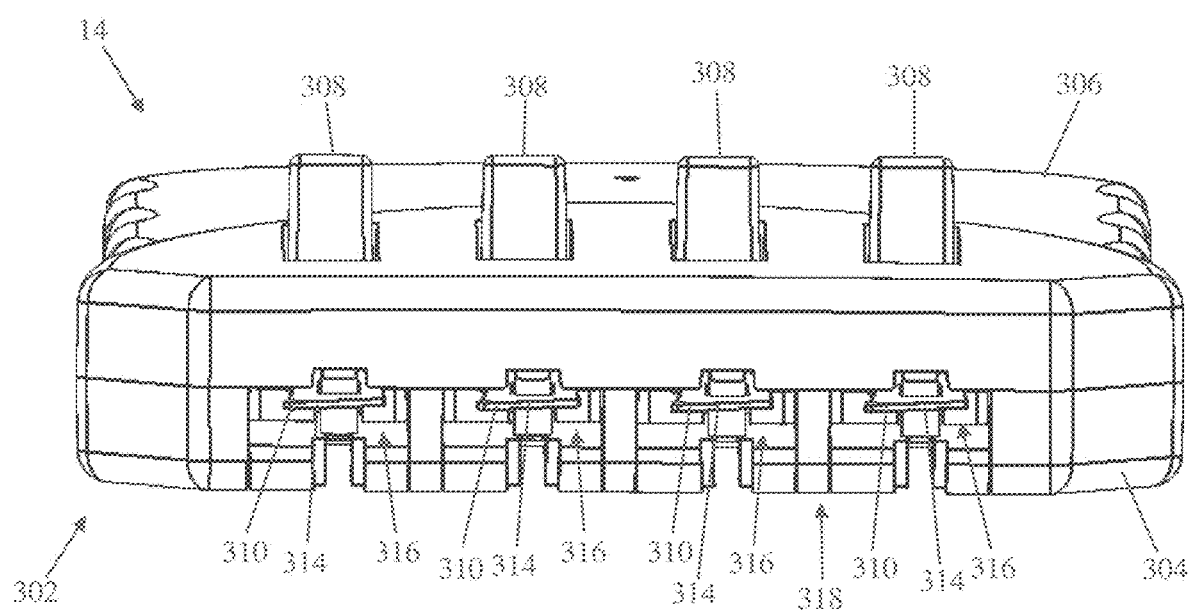
FIG. 5 is a front perspective view of the safety blade-dispenser of FIG. 2.
Figure 6:
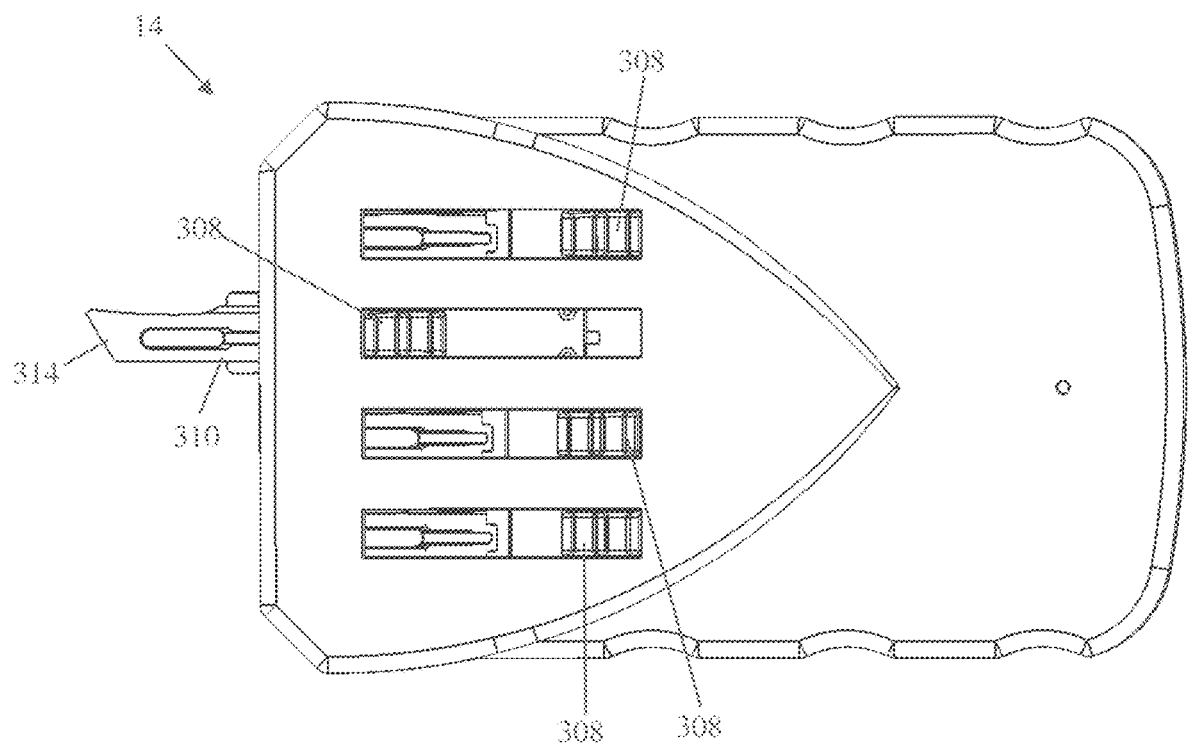
FIG. 6 is a top plan view of the safety blade-dispenser of FIG. 2 with one blade advanced to a removable position.
Figure 7:
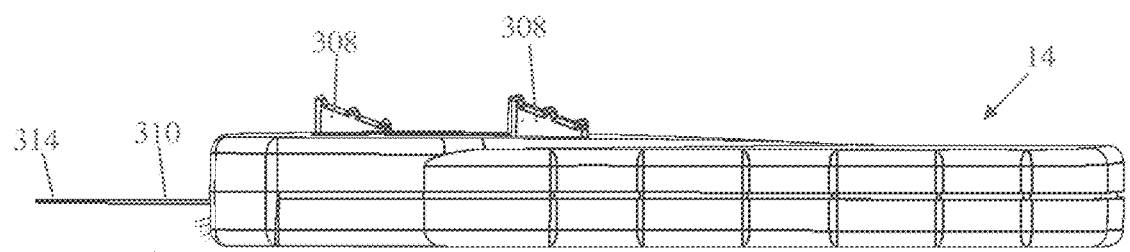
FIG. 7 is a side plan view of the safety blade-dispenser of FIG. 6.
Figure 8:
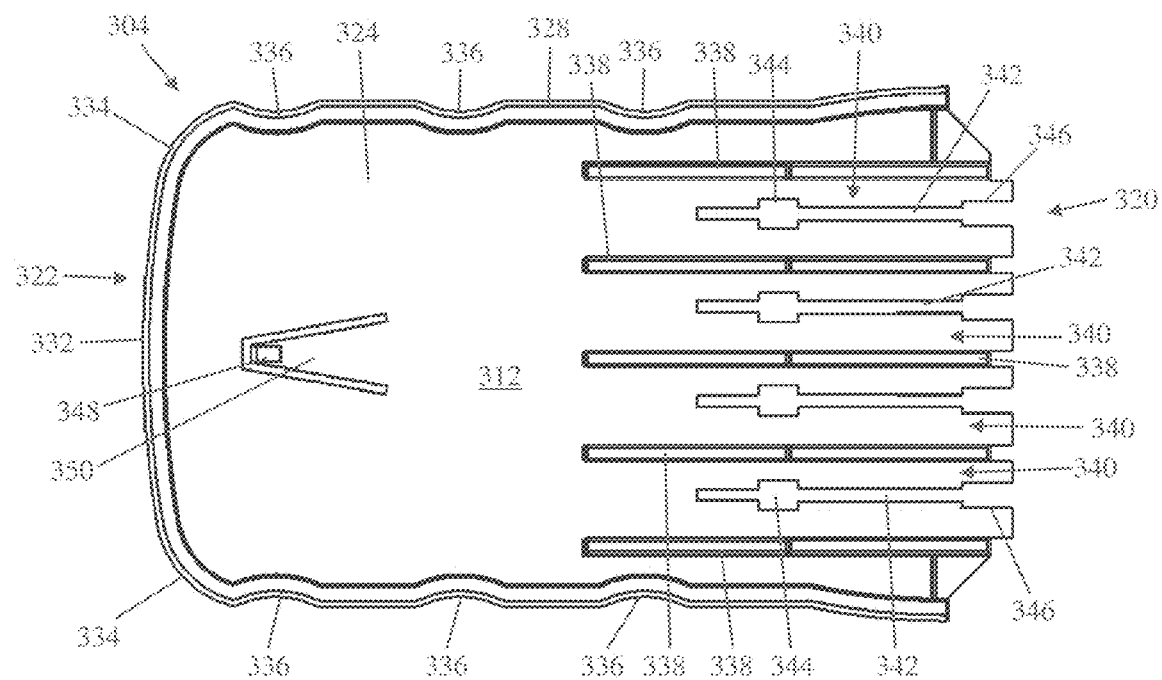
FIG. 8 is a plan view of a first housing panel forming part of the safety blade-dispenser of FIG. 2.
Figure 9:
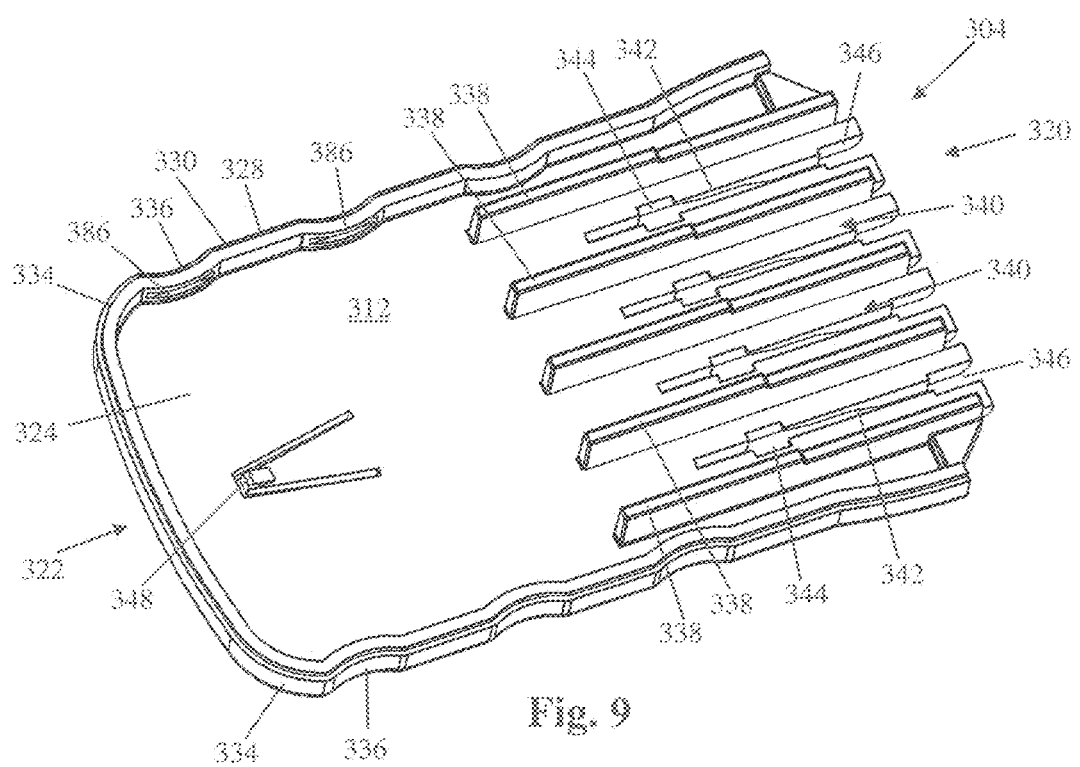
FIG. 9 is a perspective view of the first housing panel of FIG. 8.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

FIG. 1 is a graphical representation of an exemplary wrong-site surgery prevention system which may include any of the various safety-blade dispensers of the present disclosure for preventing or reducing blade-related injuries to OR personnel. As shown in the example embodiment of FIG. 1, a system 10 includes computer software system 12 configured to provide a user with a method of preventing wrong site surgeries, in combination with a safety blade-dispenser 14, as shown and described in the '210 PCT incorporated into this disclosure above. The safety blade dispenser 14 comprises at least one component, such as a label, paper, or tape, which prevents or impedes a surgeon from accessing one or more surgical instruments stored within until after a "time-out" is performed by the surgeon or authorized OR personnel before starting the intended surgical procedure. The computer software system 12 can be run on any of a variety of computing devices, such as a computer 16 (e.g. stationary desktop and/or laptop) and/or a hand-held computing device 18 (e.g. smart-phones such as IPHONE and/or a tablet device such as an IPAD or SURFACE PRO) used within the medical environment. The "medical environment" includes anywhere along the continuum in which patient and medical team (including the doctor, office personnel, nurses, medical technicians, surgeons, administrators) interact, from the surgeon's office (where the initial consultation and decision for surgery is made) to the operating room (where the surgery takes place). The term may also include personnel involved with post-surgical data collection and/or analysis, such as (but not limited to) (a) insurance companies for the patient, hospital and/or surgeon, (b) state and/or federal agency departments/programs (e.g. Medicare/Medicaid) which reimburse funds to the hospital and/or surgeon, (c) any other agency (private and/or governmental) which generates payment to the patient, hospital and/or surgeon for the specific surgical case, and/or (d) quality control and/or hospital administration to identify areas of improvement and/or best practices. The system and related methods of preventing wrong-site surgeries and sharps or blade-related injuries utilize computer software system 12 to support and provide several functionalities. These include, but are not necessarily limited to, voice recording 42, recording playback 44, an electronic patient-identifying component (such as a patient ID band 46) capable of being scanned, safety blade-dispenser 14 capable of being scanned, and any of a variety of analytics 48 generated or based upon data acquired through the use of the system 10 from "decision-to-incision", that is, from the decision to have surgery (made in the surgeon's office) through the actual surgery (in the OR). Scanning of the patient ID band 46 and/or safety blade-dispenser 14 may be accomplished by scanning functionality of the computer 16, hand-held device 18 and/or scanning systems separate from the system 10 which cooperate and communicate with the system 10. The system 10 may use any of a variety of suitable biometric identification technologies (e.g. iris scan, finger-prints, genetics, etc. . . . ) in order to identify the patient (and/or the guardian of the patient if the patient is a minor or incapacitated) at any point in the medical environment.

FIGS. 2-22 illustrate a specific example of the safety-blade dispenser 14 suitable for use with the system and methods of preventing wrong-site surgeries and blade-related injuries 10 in a surgical procedure, although it is also possible that the safety blade-dispenser 14 may be used independently of the system and methods of preventing wrong-site surgeries and blade-related injuries 10. The safety blade-dispenser 14 described herein provides a compact and convenient vessel for storage and delivery of a variety of surgical sharps, including but not limited to surgical blades (shown by way of example herein throughout), scalpels, needles, probes, syringes, and the like. As will be described below, the safety blade-dispenser 14 may be provided with a removable confirmation label and/or additional features to help reduce the incidence of wrong site surgeries. Generally, the safety blade-dispenser 14 described herein by way of example comprises a generally rectangular container having a storage portion and a handle portion, the storage portion including four blade holders arranged side-by-side in a 1.times.4 matrix configuration. The blade holders are slideable in the same direction such that all four surgical blades are removed on the same side of the device. Although shown and described in relation to this example embodiment, other box shapes and/or configurations of surgical blades are possible without departing from the scope of this disclosure.

Referring to FIGS. 2-7, the safety blade-dispenser 14 of the present example includes a housing 302 comprising a first housing panel 304 and a second housing panel 306 and at least one blade holder assembly 308 configured to releaseably hold a surgical blade 310. The first housing panel 304 and the second housing panel 306 mate to form the completed housing 302. Preferably, the safety blade-dispenser 14 includes a plurality of blade holder assemblies 308. By way of example only, the safety blade-dispenser 14 described herein includes four blade holder assemblies 308, however any number of blade holder assemblies 308 is possible. The blade holder assemblies 308 are moveable between a first position in which the surgical blade 310 is fully contained within the housing 302 (e.g. FIGS. 2-5) and a final position in which at least a portion of the surgical blade 310 is protruding from the housing 302 (e.g. FIGS. 6-7) to enable removal of the surgical blade 310 from the housing 302. By way of example, the movement may be unidirectional or bidirectional.

The housing 302 is generally compact in size, allowing the safety blade-dispenser 14 to be held and operated in the palm of a single user's hand, while being large enough to contain and dispense at least one surgical blade 310. The housing 302 is generally rectangular in shape with rounded and/or scalloped edges 336 for ease of gripping. The housing 302 may be made of plastic or any other suitable material. The housing 302 further has an interior cavity 312, see FIG. 9, flanked by the first and second housing panels 304, 306, in which the blade holder assemblies 308 and surgical blades 310 reside. The blades 310 emerge from the interior cavity 312 through distal openings 316 (e.g., apertures) formed within the distal end 318 of the housing 302, with the proximal end 314 of the blade 310 being presented for association with a suitable receiver (e.g. scalpel handle). Once the blade 310 has been attached to the receiver, it may be fully removed from the blade holder assembly 308 and used in the surgical procedure.

FIGS. 8-11 illustrate the first housing panel 304 in greater detail. The first housing panel 304 comprises a generally planar, generally rectangular member having a first end or distal end 320, a second opposing or proximal end 322, an interior surface 324 and an exterior surface 326. The interior surface 324 faces the interior cavity 312 when the first housing panel 304 is mated to the second housing panel 306 to form the housing 302. The interior surface 324 is generally smooth and generally planar and is flanked by a peripheral ridge 328 that forms a portion of the sidewalls 330 of the housing 302. The peripheral ridge 328 may have several ergonomic features that enable a user to comfortably and securely grip and operate the safety blade-dispenser 14 in a single hand, including but not limited to a curved proximal edge 332, rounded proximal corners 334, and a plurality of scalloped indentations 336. The curved proximal edge 332 and rounded proximal corners 334 enable a smooth feel in a user's hand while the scalloped indentations 336 provide extra grip for a user's fingers.

A plurality of parallel, elongated walls 338 extend longitudinally inward from the distal end 320 toward the proximal end 322. The space between two elongated walls 338 forms a channel 340 that is sized and configured to slideably receive one blade holder assembly 308 therein. Therefore, the number of elongated walls 338 provided depends upon the number and/or type of surgical blades 310 (or other surgical sharps) a particular safety blade-dispenser 14 contains. In the instant example, the first housing panel 304 includes five elongated walls 338 spaced apart to form four channels 340 to receive the four blade holder assemblies 308 therein. Each channel 340 further includes an elongated slit 342 formed through the first housing panel 304 between the interior and exterior surfaces 324, 326 and extending inward from the distal end 320. As will be described in further detail below, the elongated slit 342 enables controlled translation of the blade holder assembly 308 within the channel 340. The elongated slit 342 is configured to slideably receive the post 420 of the blade holder assembly 308 therethrough. Each elongated slit 342 further includes a first, or proximal widening 344 and a second, or distal widening 346. The proximal widening 344 allows passage of the crossbar 422 of the blade holder assembly 308 through the first housing panel 304 during assembly and is shown by way of example as a generally rectangular aperture. The distal widening 346 allows the shaped end 418 of the blade holder assembly 308 to pass through the first housing panel 304 while it pivots away from the surgical blade 310 (and out of the central aperture 428) to enable removal of the surgical blade 310 once the blade holder assembly 308 is fully translated. By way of example, the distal widening 346 comprises a generally rectangular cutaway having one edge at the proximal end 320.

The first housing panel 304 further includes a lock tab 348 configured to prevent the first housing panel 304 from dissociating from the second housing panel 306 absent a sufficient targeted force. The lock tab 348 comprises a flange 350 that is biased inward (e.g. into the interior cavity 312 of the housing 302). When the housing 302 is properly assembled, the lock tab 348 abuts the lock post 380 of the second housing panel 306 (see FIG. 12), preventing dissociation of the first and second housing panels 304, 306. To unlock the safety blade-dispenser 14, a user inserts a suitable unlocking tool through the proximal unlock aperture 378 of the second housing panel 306 so that the unlocking tool engages the lock tab 348. The user then exerts a sufficient force to cause the lock tab 348 to pivot against the inward bias and lift over the lock post 380, enabling the first and second housing panels 304, 306 to be dissociated from one another. This might be necessary for example if the user wanted to load different set of surgical blades 310 before beginning the surgical procedure.

Figure 10:
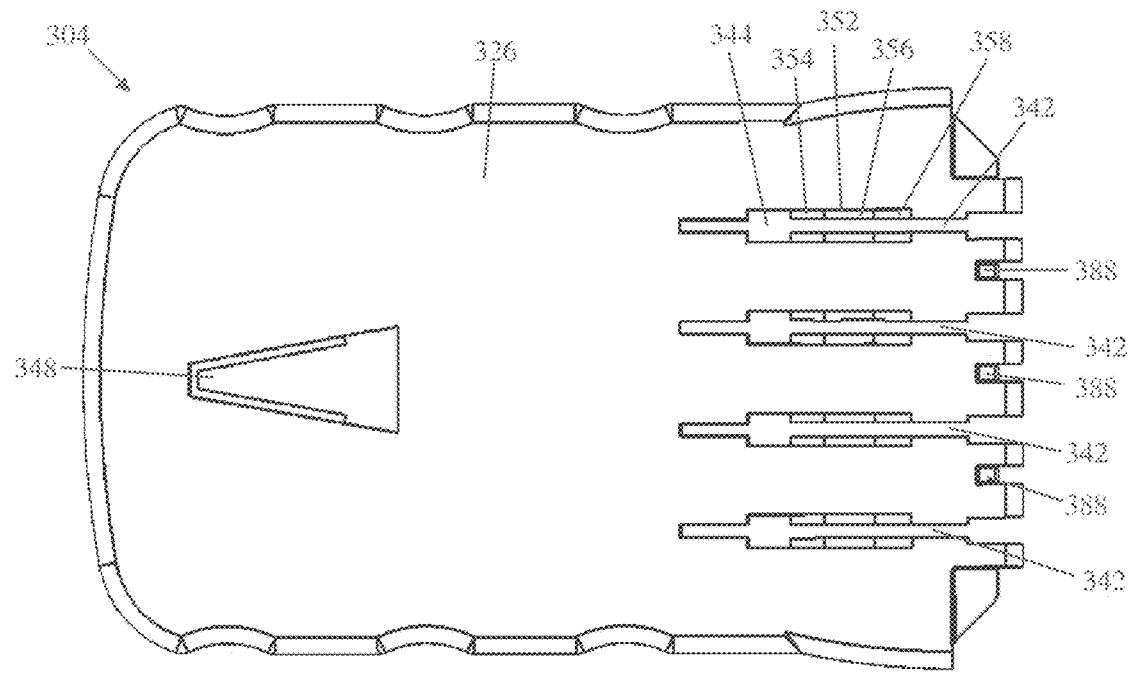
FIG. 10 is another plan view of the first housing panel of FIG. 8.
Figure 11:
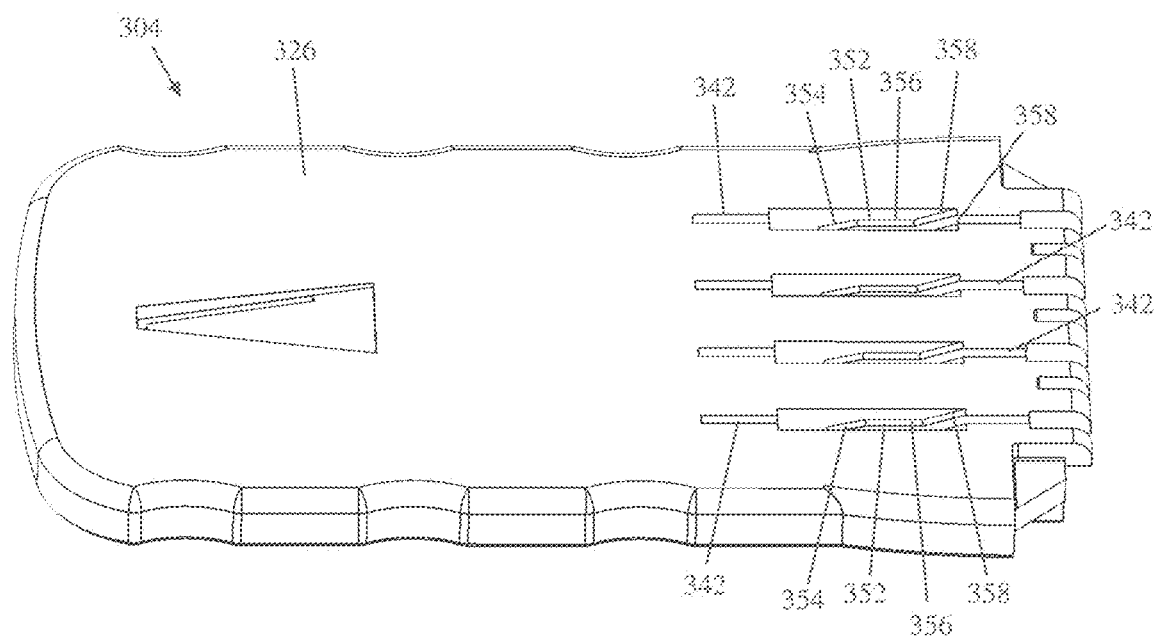
FIG. 11 is another perspective view of the first housing panel of FIG. 8.

Referring now to FIGS. 10-11, the exterior surface 326 faces away from the interior cavity 312 when the first housing panel 304 is mated to the second housing panel 306 to form the housing 302, and is the surface that interacts with a user's hand. As such, the exterior surface 326 may be provided with one or more frictional elements to improve a user's grip on the device. The exterior surface 326 further includes a pair of ramped ledges 352 flanking each elongated slit 342. Each ramped ledge 352 includes a first beveled portion 354, a generally level intermediate portion 356, and a second beveled portion 358. The first beveled portion 354 is positioned adjacent the proximal widening 344 and includes the thinnest portion of the ramped ledge 352. The intermediate portion 356 is generally level (e.g. generally parallel to the exterior surface 326). The second beveled portion 358 is positioned adjacent the intermediate portion 356 and includes the thickest portion of the ramped ledge 352. As will be explained in further detail below, the ramped ledges 352 interact with the blade holder assembly 308 to release the surgical blade 310 from the holder assembly 308, thereby making the blade 310 available for interaction with an appropriate receiver (e.g. scalpel handle).

Figure 12:
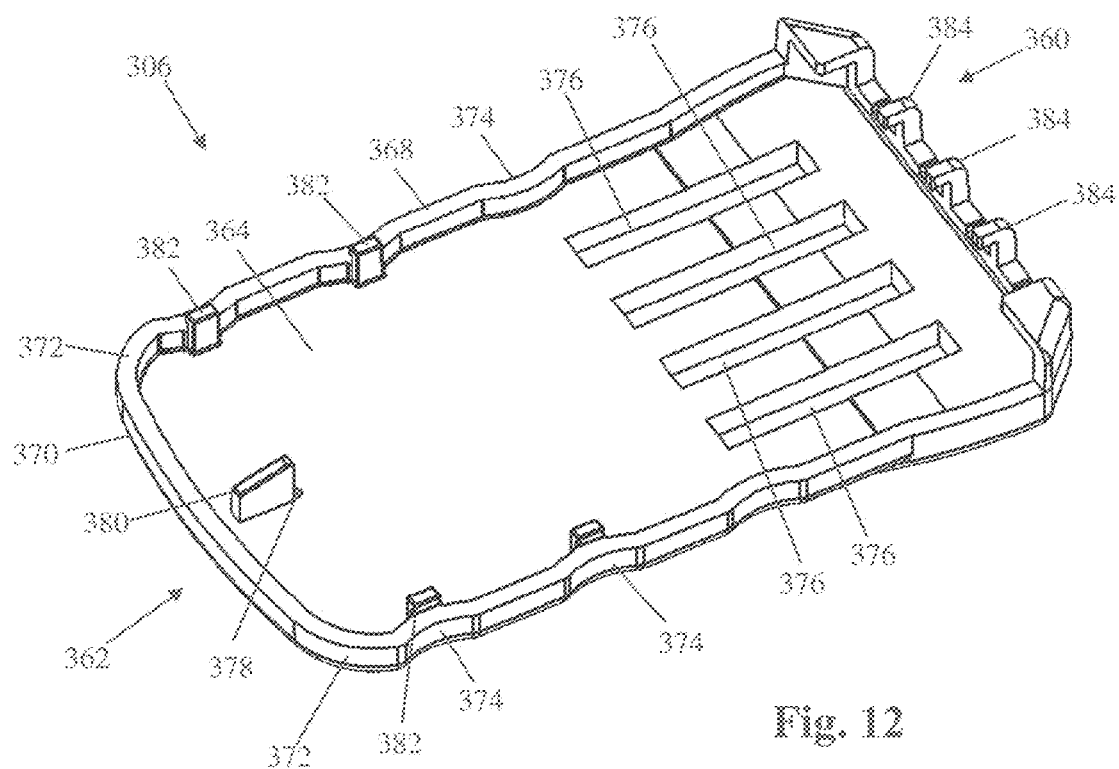
FIG. 12 is a perspective view of a second housing panel forming part of the safety blade-dispenser of FIG. 2.
Figure 13:
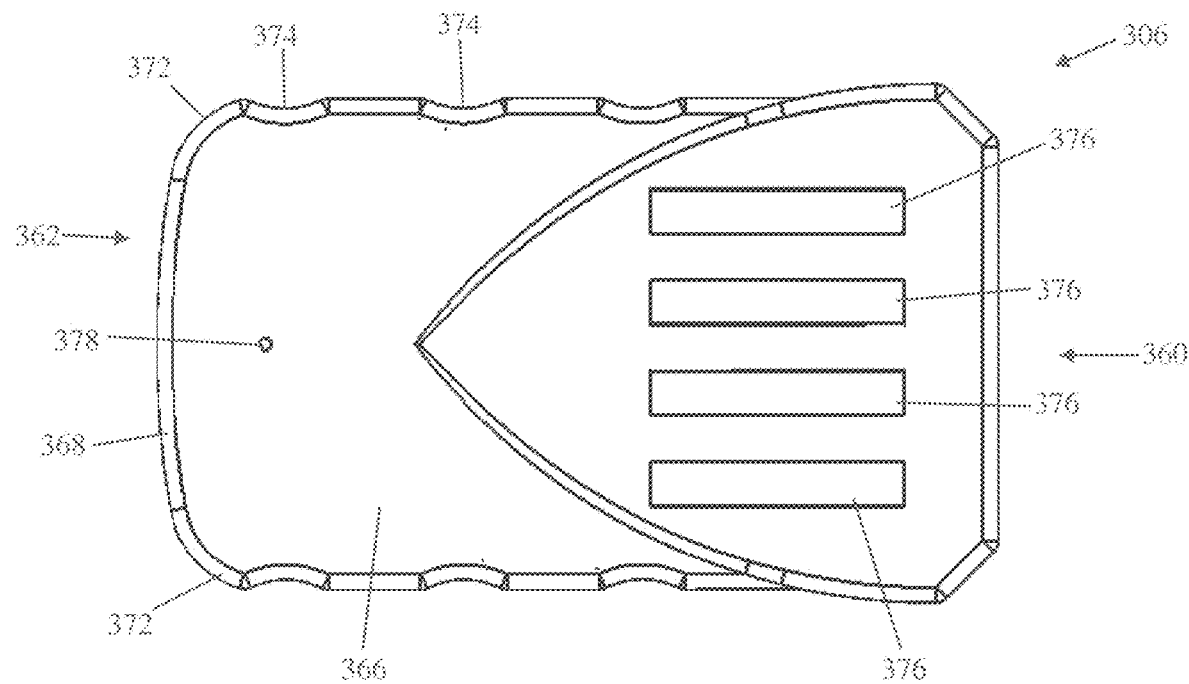
FIG. 13 is a plan view of the second housing panel of FIG. 12.

FIGS. 12-13 illustrate the second housing panel 306 in greater detail. The second housing panel 306 comprises a generally planar, generally rectangular member having a first or distal end 360, a second opposing or proximal end 362, an interior surface 364 and an exterior surface 366. The interior surface 364 faces the interior cavity 312 when the second housing panel 306 is mated to the first housing panel 304 to form the housing 302. The interior surface 364 is generally smooth and generally planar and is flanked by a peripheral ridge 368 that forms a portion of the sidewalls 330 of the housing 302. The peripheral ridge 368 may have several ergonomic features that enable a user to comfortably and securely grip and operate the surgical sharp dispenser 300 in a single hand, including but not limited to a curved proximal edge 370, rounded proximal corners 372, and a plurality of scalloped indentations 374. The curved proximal edge 370 and rounded proximal corners 372 enable a smooth feel in a user's hand while the scalloped indentations 374 provide extra grip for a user's fingers.

The second housing panel 306 further includes a plurality of elongated openings 376 positioned near the distal end 360. The elongated openings 376 not only function to allow passage of the engagement flange 396 of the blade holder assembly 308 through the second housing panel 306, but also provide a visible window through which a user can see the surgical blades 310 contained therein. The proximal unlock aperture 378 is positioned near the proximal end 362 and allows a user to unlock the safety blade-dispenser 14 if so desired. The lock post 380 is positioned near the proximal end 362 and extends from the interior surface 364. As explained previously, the lock post 380 interacts with the lock tab 348 to prevent the housing 302 from coming apart until desired by the user. Proximal coupling flanges 382 and distal coupling flanges 384 are configured to engage the proximal coupling apertures 386 and the distal coupling apertures 388, respectively, on the first housing panel 304 to hold the housing 302 together.

Figure 14:
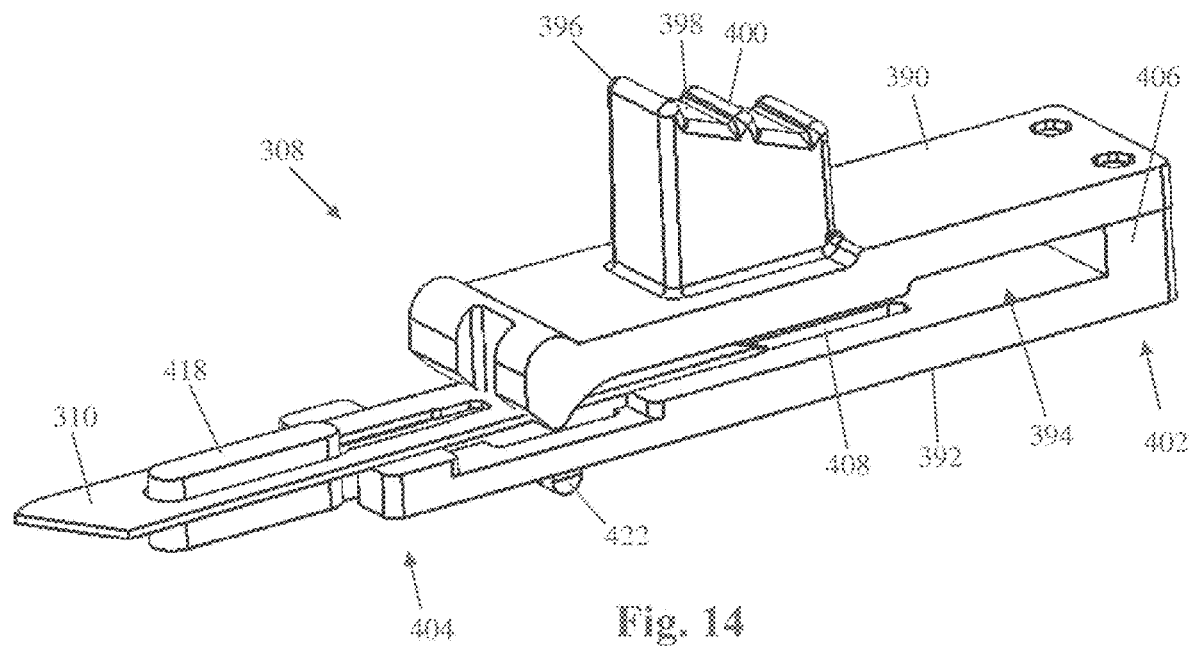
FIG. 14 is a perspective view of a blade holder assembly forming part of the safety blade-dispenser of FIG. 2.
Figure 15:
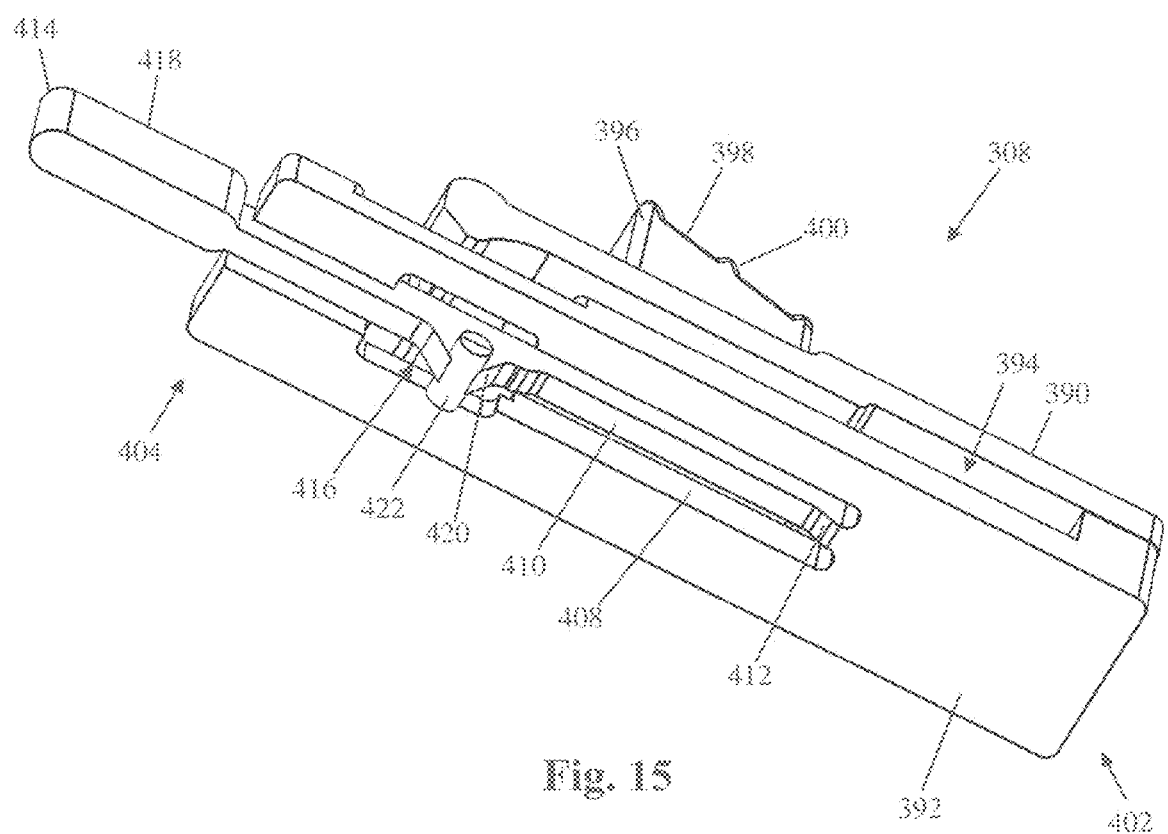
FIG. 15 is another perspective view of the blade holder assembly of FIG. 14.
Figure 16:
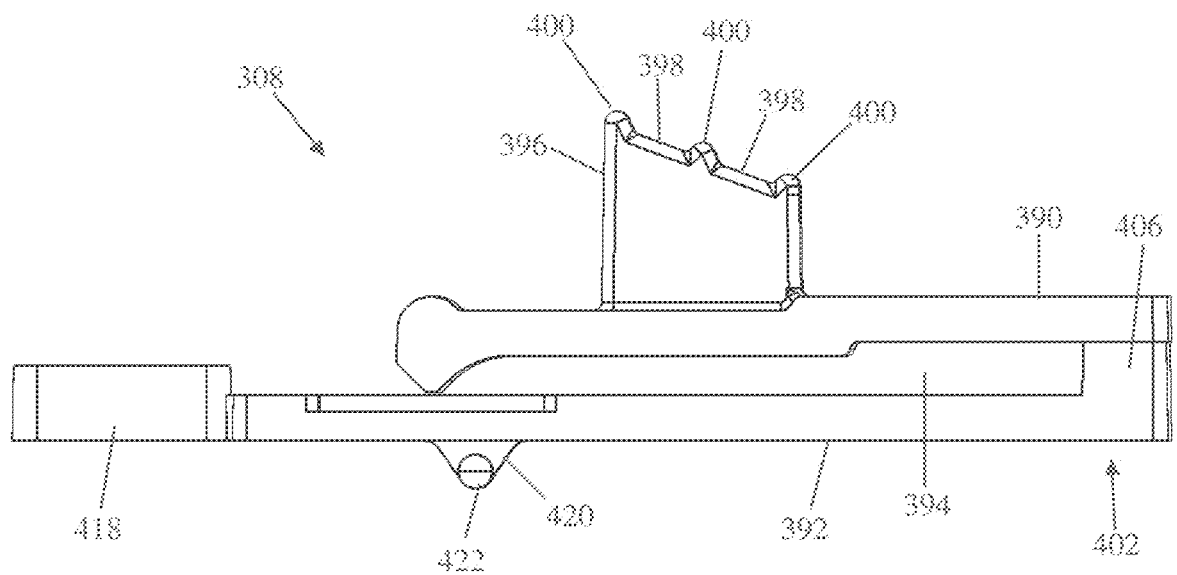
FIG. 16 is a side plan view of the blade holder assembly of FIG. 14.

FIGS. 14-16 illustrate one example of a surgical blade holder assembly 308 in greater detail. The surgical blade holder assembly 308 described herein includes a top panel 390 connected to a bottom panel 392 in such a way that creates a space 394 in between the top and bottom panels 390, 392. The top panel 390 includes an engagement flange 396 extending generally perpendicularly away from the top panel 390. The engagement flange 396 extends through an elongated opening 376 of the second housing panel 306 and includes an angled top surface 398 that may include one or more friction elements 400 (e.g. ridges) to improve the ability of a user to move the blade holder assembly 308 during use.

The bottom panel 392 by way of example has a generally rectangular shape, and includes a first or proximal end 402 and a second or distal end 404. The proximal end 402 includes an attachment post 406 extending from the upper surface of the bottom panel 392, to which the top panel 390 is attached thus creating the space 394. The bottom panel 392 further includes an elongated recess 408 formed therein and extending from the distal end 404 into the interior of the bottom panel 392. An elongated flange 410 having a proximal end 412, a distal end 414, and an intermediate portion 416 extends proximally back through the elongated recess 408. The proximal end 412 of the elongated flange 410 is attached to (or may be an integral extension of) the bottom panel 392. The distal end 414 of the elongated flange 410 includes a shaped end 418 sized and configured to securely engage the central aperture 428 of the surgical blade 310. The shaped end 418 extends beyond the distal end 404 of the bottom panel 392. The intermediate portion 416 includes a post 420 having a crossbar 422 positioned at the end of the post 420. The post 420 is sized to extend through and translate within the elongated slit 342 of the first housing panel 304.

The crossbar 422 interacts with the ramped ledges 352 flanking each elongated slit 342 as the blade holder assembly 308 is translated during use. More specifically, as the blade holder assembly 308 is translated distally along the channel 340, the crossbar 422 first engages the first beveled portions 354 of the ramped ledges 352. This initial interaction provides some physical resistance to the translational movement of the blade holder assembly 308 and helps prevent unintentional ejection of the surgical blades 310. That is, in order to overcome the physical resistance to translation, the user must apply a greater force to the engagement flange 396. Once the crossbar 422 reaches the intermediate portions 356, the proximal end 314 of the surgical blade 310 starts to emerge from the corresponding distal opening 316. At this point the user may view a size marking on the proximal end 314 of the blade 310 to confirm it is the intended surgical blade 310. Additional force is needed to traverse the second beveled portion 358 as it is beveled at a greater angle than the first beveled portion 354. This interaction forces the elongated flange 410 to temporarily bend, which urges the shaped end 418 out of the central aperture 428 of the surgical blade 310 (e.g. FIG. 7), allowing the surgical blade 310 to be engaged with another instrument (e.g. scalpel handle) and removed from the safety blade-dispenser 14.

Figure 17:
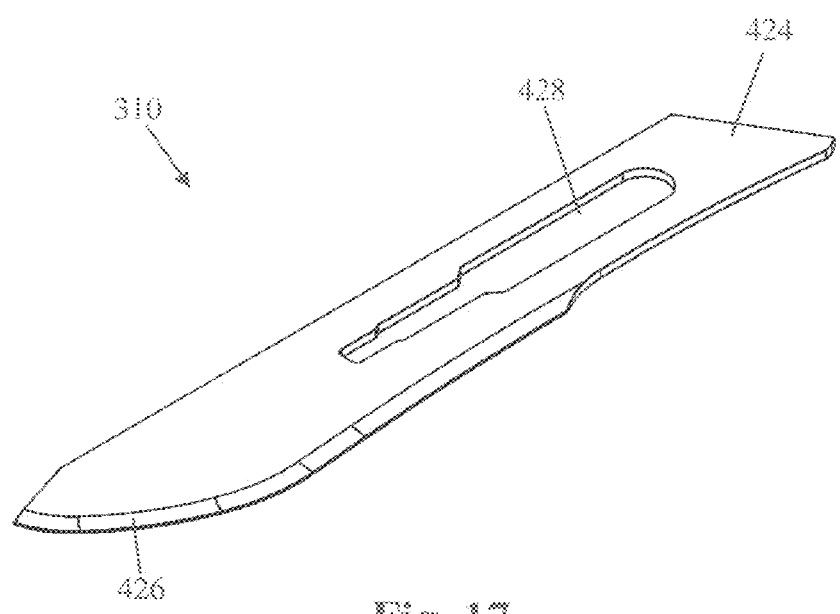
FIG. 17 is a perspective view of an example of a surgical blade configured for use with the safety blade-dispenser of FIG. 2.

FIG. 17 illustrates one example of a surgical blade 310 suitable for use with the safety blade-dispenser 14 of the present disclosure. By way of example, the surgical blade 310 includes an engagement portion 424 and a blade 426. The engagement portion 424 includes a central aperture 428 having a size and shape that is complementary to the shaped end 418 so as to securely receive the shaped end 418 therein.

Figure 18:
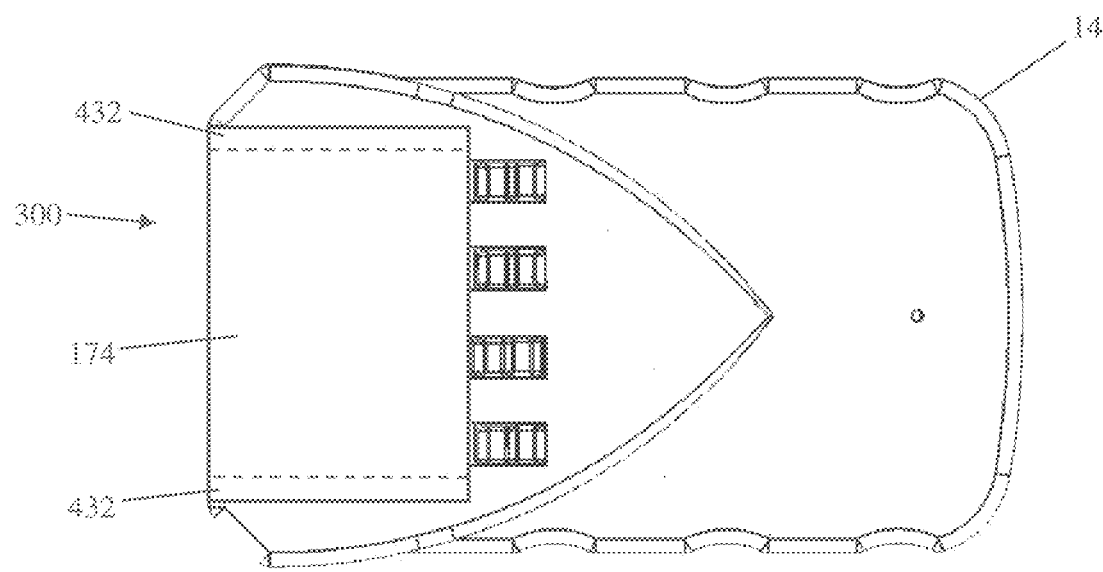
FIGS. 18 and 19 are plan views of the safety blade-dispenser of FIG. 2 with a confirmation label attached.
Figure 19:
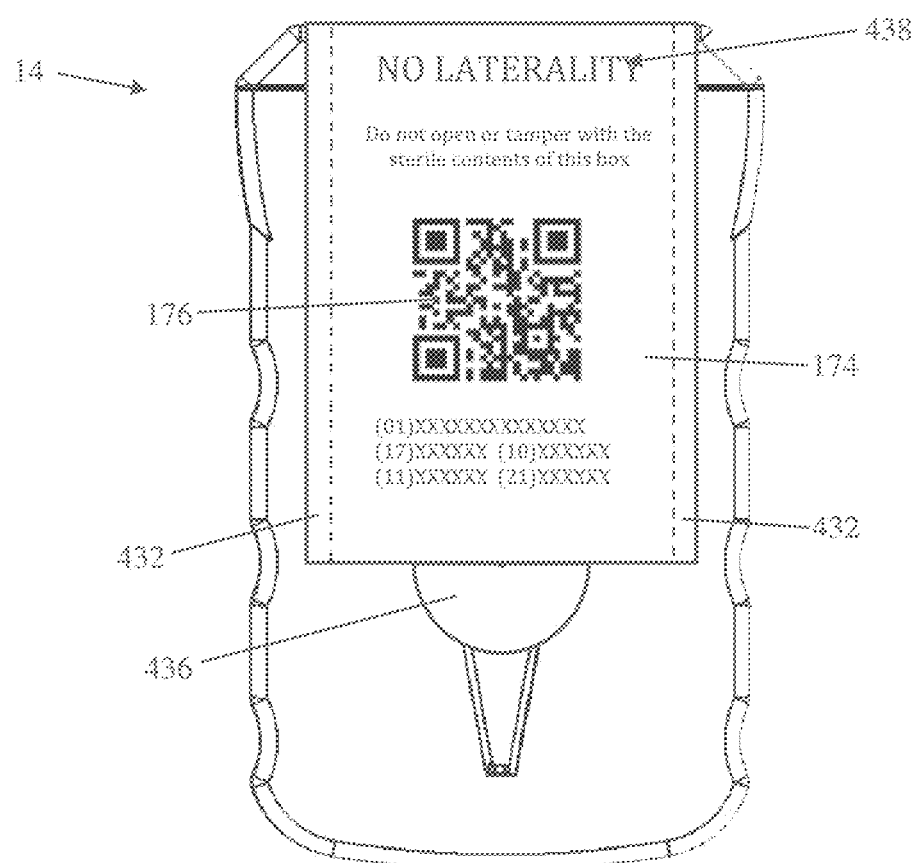

Referring to FIGS. 18-19, the safety blade-dispenser 14 shown and described herein may be provided with a confirmation label 174 to help reduce the prevalence of wrong site surgeries. The confirmation label 174 is placed in a manner that renders the surgical blades 310 inaccessible unless and until the user removes the label 174. The confirmation label 174 does not have adhesive on it, but is affixed to the safety blade-dispenser 14 via attached sticky strips 432 from which the label 174 can be torn away. By way of example, the confirmation label 174 may include any suitable patient data printed on the label and/or contained in an electronically scannable code (e.g. QR code 176, bar code, and the like) that the user must scan before removing the confirmation label 174. The confirmation label 174 further includes a pull-tab 436 to enable more efficient removal. In addition to patient data, the confirmation label 174 may include a laterality indicator 438 that immediately visually conveys to the user the laterality, if any, of the procedure. This laterality indicator 438 may include words and/or be color coded. For example, the label may include the words "LEFT" and/or be colored lavender to indicate a left side surgery, "RIGHT" and/or red color to indicate a right side surgery, and "NO LATERALITY" and/or gray color to indicate no laterality. Once the confirmation label 174 has been removed, it can be attached to the patient record by any suitable means.

Figure 20:
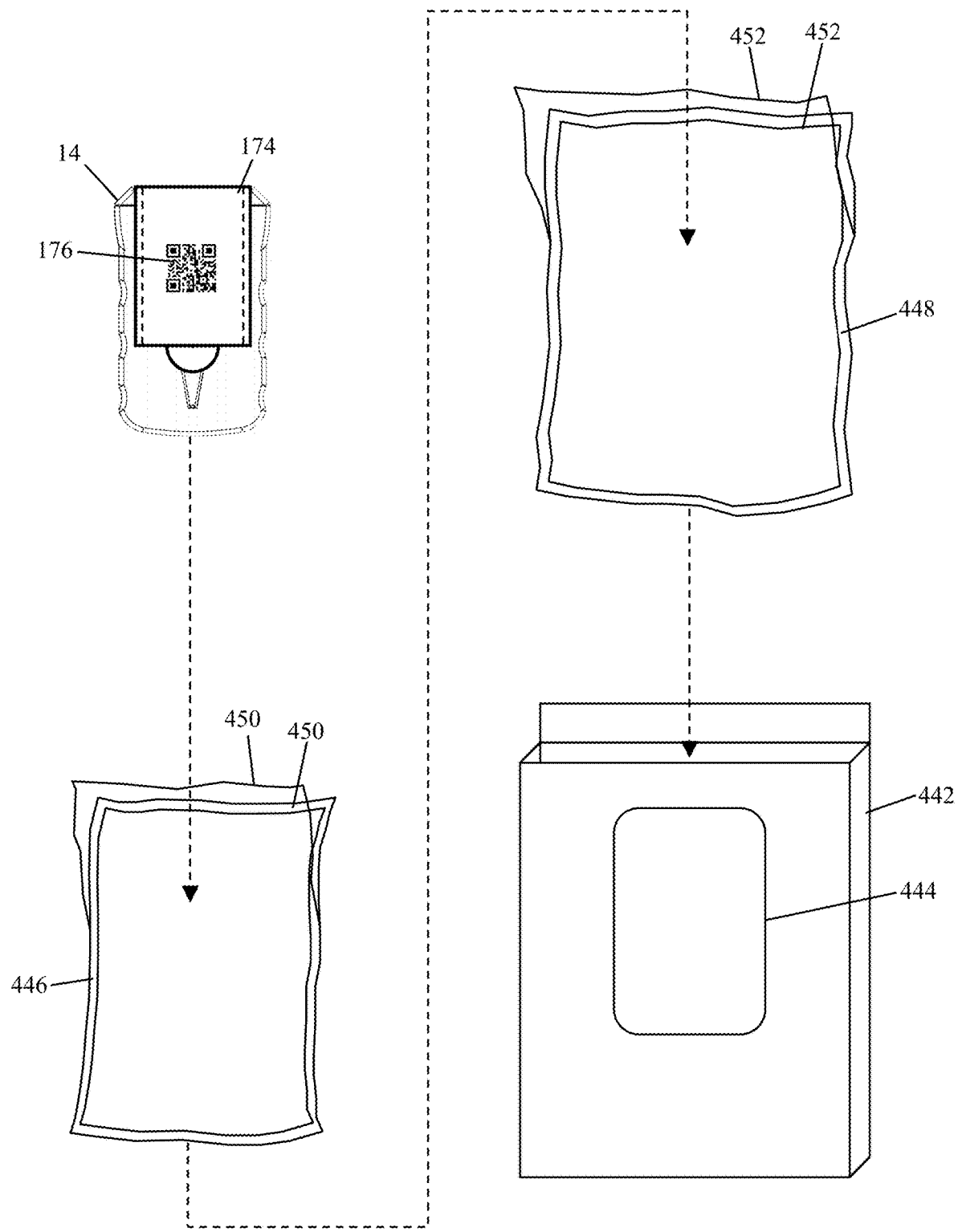
FIG. 20 is an exploded perspective view of the safety blade-dispenser of FIG. 2 with dual inner packaging (sterile and transparent) and an outer container with transparent viewing window according to an aspect of the present disclosure.
Figure 21:
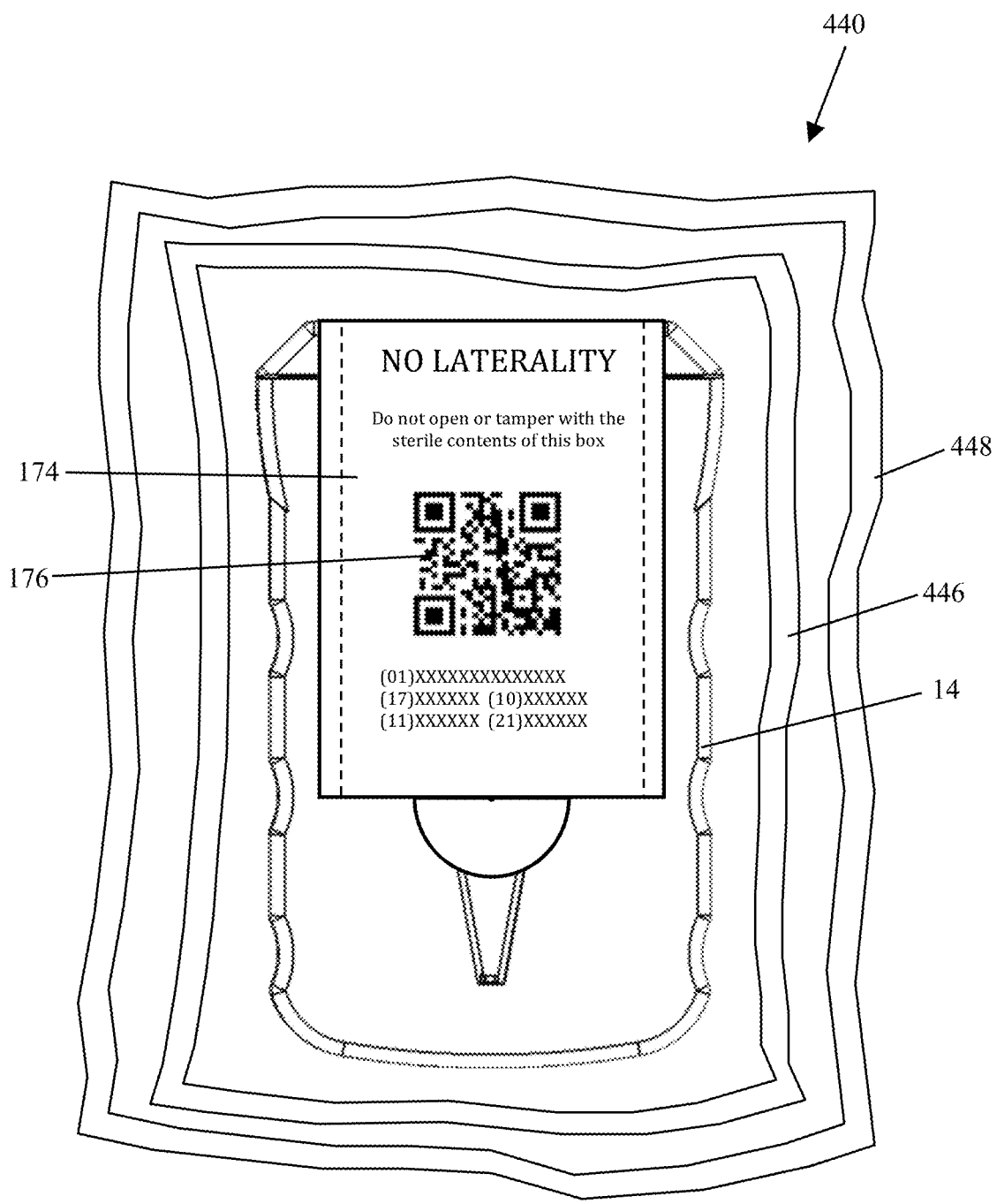
FIG. 21 is a plan view of the safety blade-dispenser of FIG. 20 sealed within the dual sterile and transparent inner packaging.
Figure 22:
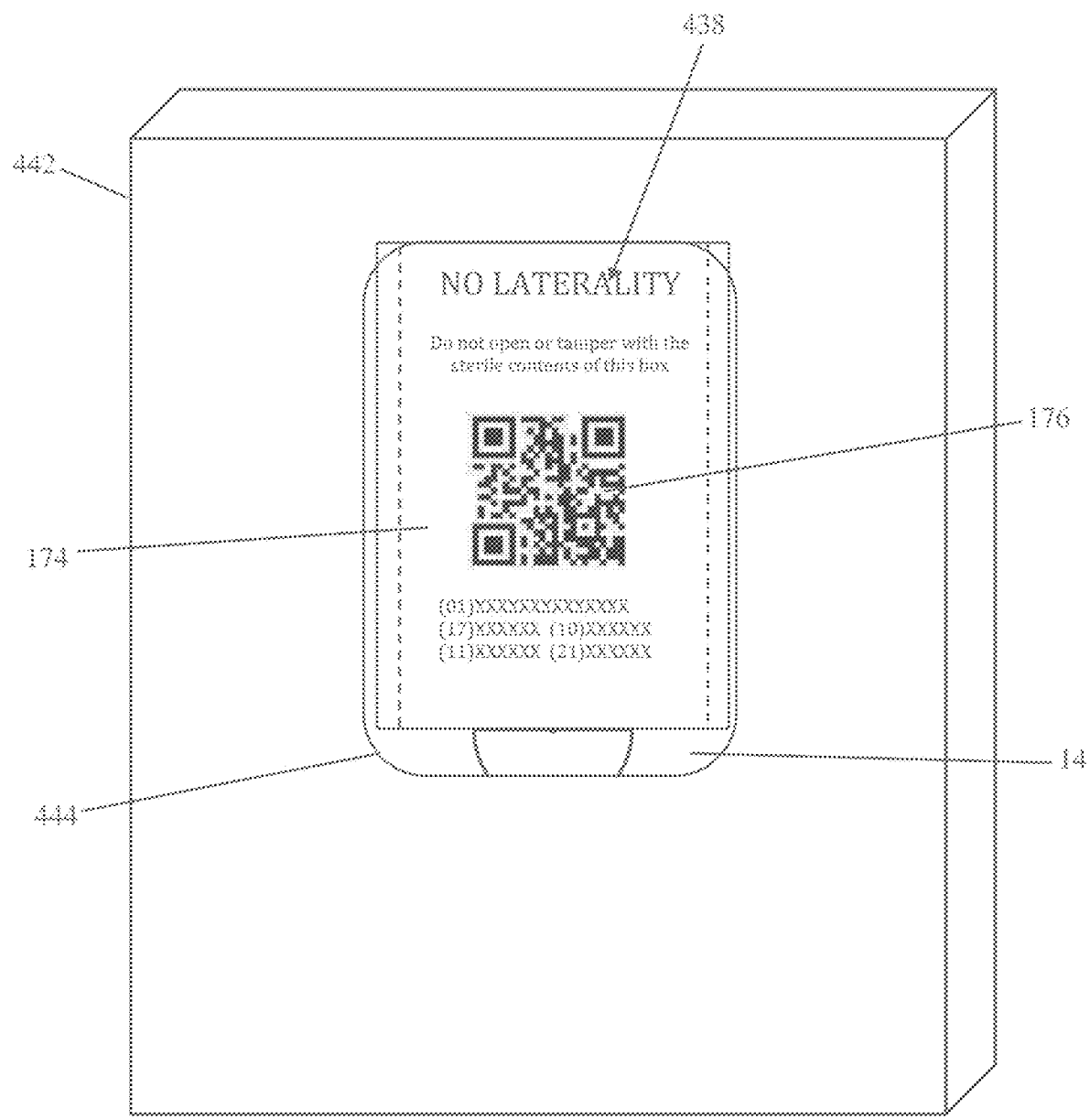
FIG. 22 is a perspective view of the safety blade-dispenser of FIG. 21 sealed within the dual sterile and transparent inner packaging and further enclosed within the outer container with transparent viewing window for viewing the label of the safety-blade dispenser while fully sealed and packaged.

As shown in FIGS. 20-22, the safety blade-dispenser 14 of the present disclosure is preferably provided within double sterile packaging 440 disposed within a container 442 having a transparent window section 444. More specifically, the safety blade-dispenser 14 is disposed within a first sterile package 446, which is then sealed within a second sterile package 448. Both the first and second sterile packages 446, 448 are transparent and relatively easy to open (using pull-apart flaps 450, 452 positioned on one end of each package 446, 448, respectively). The combined sterile packages 446, 448 are disposed within the container 442 such that identifying information on the confirmation label 174 (e.g. QR code 176 and/or laterality indicator 438) may be scanned through the transparent window section 444 of the container 442 and the transparent first and second sterile packages 446, 448. In this manner, one can avoid the need to have the same identifying information on any of the packaging (i.e. first sterile package 446, second sterile package 448, or outer container 442). This reduces manufacturing costs and the complexity of matching multiple packaging components to ensure they all have the same identifying information, which would otherwise be required but for the transparent sterile packages 446, 448 within the container 442 having the transparent window section 444 through which the identifying information on the label 174 may be scanned.

Although the safety blade-dispenser 14 is shown and described as having four blade holder assemblies 308 arranged side-by-side (e.g. 1.times.4 matrix), other configurations are possible. For example, a narrower container may be provided where the blades 310 are arranged in a planar 2.times.2 matrix configuration, where two blades 310 are ejected in one direction and the other two blades are ejected in the opposite direction. The planar configuration allows all four viewing apertures to be on the same side of the device for ease of counting the blades. Another possible configuration includes a stacked 2.times.2 matrix configuration, where all four blades 310 may be ejected in the same direction, but only two are visible at any one time. The user would have to rotate the container to view the other two blades. In another alternative example, a non-rectangular container may be provided wherein the blades 310 are ejected at a slight angle. Blade configuration in such a container may be 1.times.4, 2.times.2 or any other configuration that is safe for the user.

The blades 310 provided in the safety blade-dispenser 14 have been carefully selected in advance of the patient's surgery. Therefore, it is critical that the safety blade-dispenser 14 be in the physical vicinity of the patient at all times prior to the procedure. One such possibility is that the safety blade-dispenser 14 (as provided in FIGS. 21-22 in double sterile packaging 440 and outer container 442 with a confirmation label 174 clearly visible) is attached to the patient's medical chart in a non-obstructive manner. The attachment may be accomplished by any suitable method, for example including but not limited to elastic band, tape, binder clip (integrated or stand-alone), hook and loop fasteners (e.g. Velcro), suction cup, zip tie, hole for ring binder, and the like. Another possibility is to attach the safety blade-dispenser 14 directly to the patient, for example via a wristband or ankle band. Still another possible location may be to attach the safety blade-dispenser 14 to the patient's IV stand or drip bag.

Figures 23, 24:
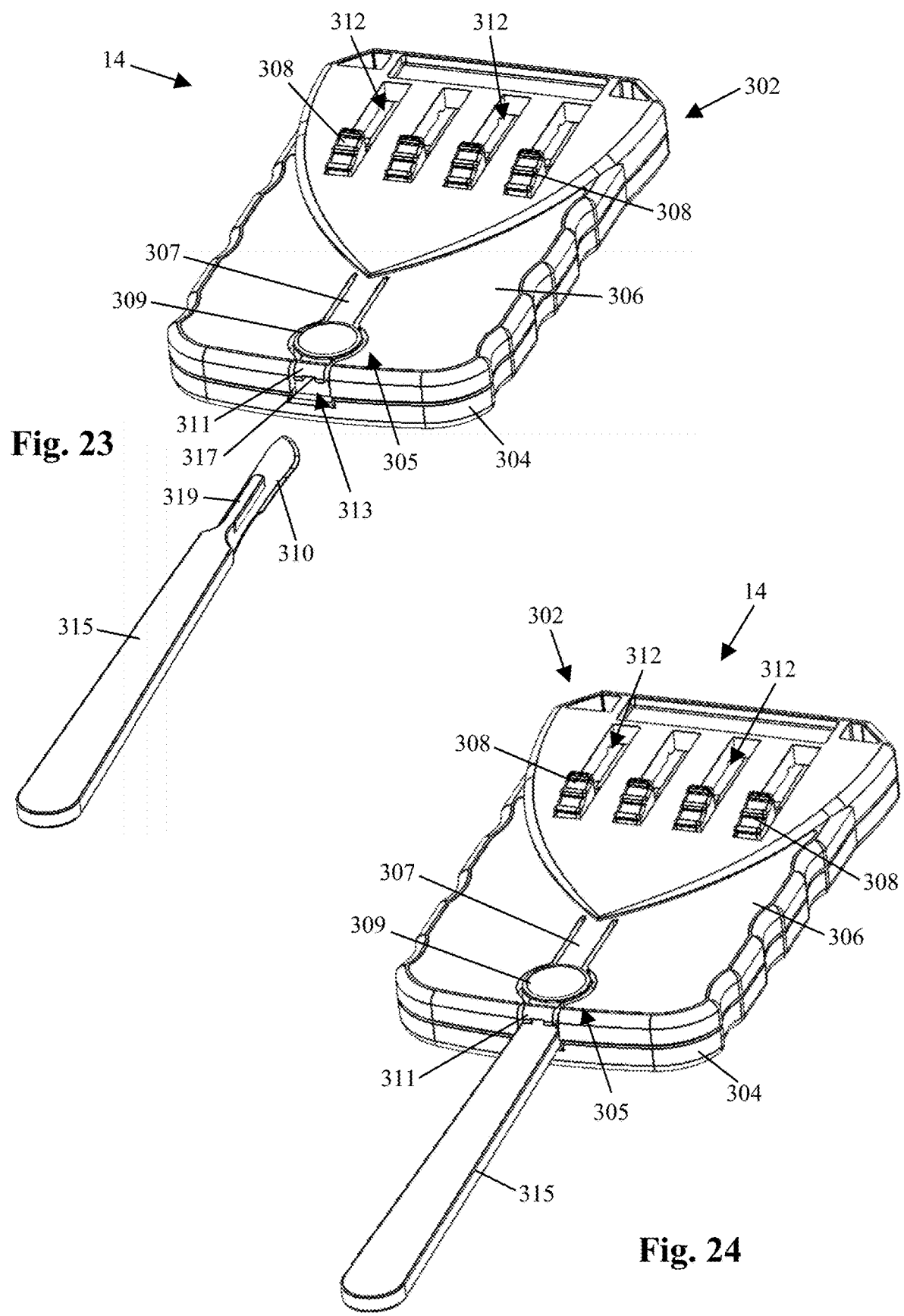
FIG. 23 is a safety-blade dispenser of the type shown in FIG. 2 with an optional blade removal feature, illustrating a blade and handle positioned to be inserted into a blade removal aperture.
FIG. 24 is the safety-blade dispenser of FIG. 23 with the optional blade removal feature, illustrating the blade and handle positioned within the housing to remove the blade.

FIGS. 23 and 24 illustrate an optional blade removal feature that may be provided as part of the safety-blade dispenser 14 according to one aspect of the present disclosure. In particular, the housing 302 may be equipped with a flexible element 305 formed as an integral and contiguous part of the second housing member 306. The flexible element 305 includes an elongated first section 307, an expanded second section 309, and an end section 311. The elongated first section 307 extends rearwardly from a generally central region of the second housing member 306. The expanded second section 309 has an expanded or enlarged periphery relative to that of the elongated first section 307 and the end section 311. By way of example only, the expanded or enlarged periphery of the expanded second section 309 may take the form of a generally circular or disc-shape, although it will be appreciated that any number of suitable shapes may be employed without departing from the present disclosure. The end section 311 extends rearwardly from the expanded second section 309 and forms part of a boundary of blade removal aperture 313.

The blade removal aperture 313 extends into the interior cavity 312 of the housing 302 and is dimensioned to receive the surgical blade 310 and a distal region of a blade handle 315. More specifically, the interior surface of the end section 311 (and optionally the expanded second section 309) is equipped with an elongated recess or notch 317 that matches the approximate profile of a blade engagement arm 319 of the blade handle 315.

When a user wants to remove the surgical blade 310 from the blade handle 315, he or she can simply align the blade handle 315 and blade 310 with the longitudinal axis of the blade removal aperture 313 and then introduce the distal region of the scalpel (that is, the blade 310, the blade engagement arm 319, and a distal section of the blade handle 315 as shown in FIG. 24). At that point, the user may press down upon the expanded second section 309 of the flexible element 305 in order to pinch or otherwise retain the blade 310. With the blade 310 temporarily immobilized due to the compression of the expanded section 309 (such as by the user pressing their thumb against the expanded section 309 with one hand), the user may then tilt or otherwise angle the blade handle 315 to release the blade 310 from the blade engagement arm 319.

Once the blade 310 has been disengaged from the handle 315, the flexible element 305 may then be released such that the handle 315 may be removed from the blade removal aperture 313 while the blade 310 remains within the internal cavity 312 of the housing 302. In this manner, the user may safely remove the blade 310 after surgery without needing to physically touch or manipulate the blade with their hands, which represents an improved safety profile due to the reduction in blade related injuries due to blade handling. The internal cavity 312 may be dimensioned to house or retain one or multiple retrieved blades after use in surgery. The confirmation label 174 may be dimensioned to cover the blade retrieval aperture 313 prior to use of the blade dispenser 14 in surgery. After the removal of the blade(s), tape or any other suitable blocking mechanism may be employed to prevent the egress of any of the retrieved blades 310 that have been removed and stored within the housing 302, if required.

Figure 25:
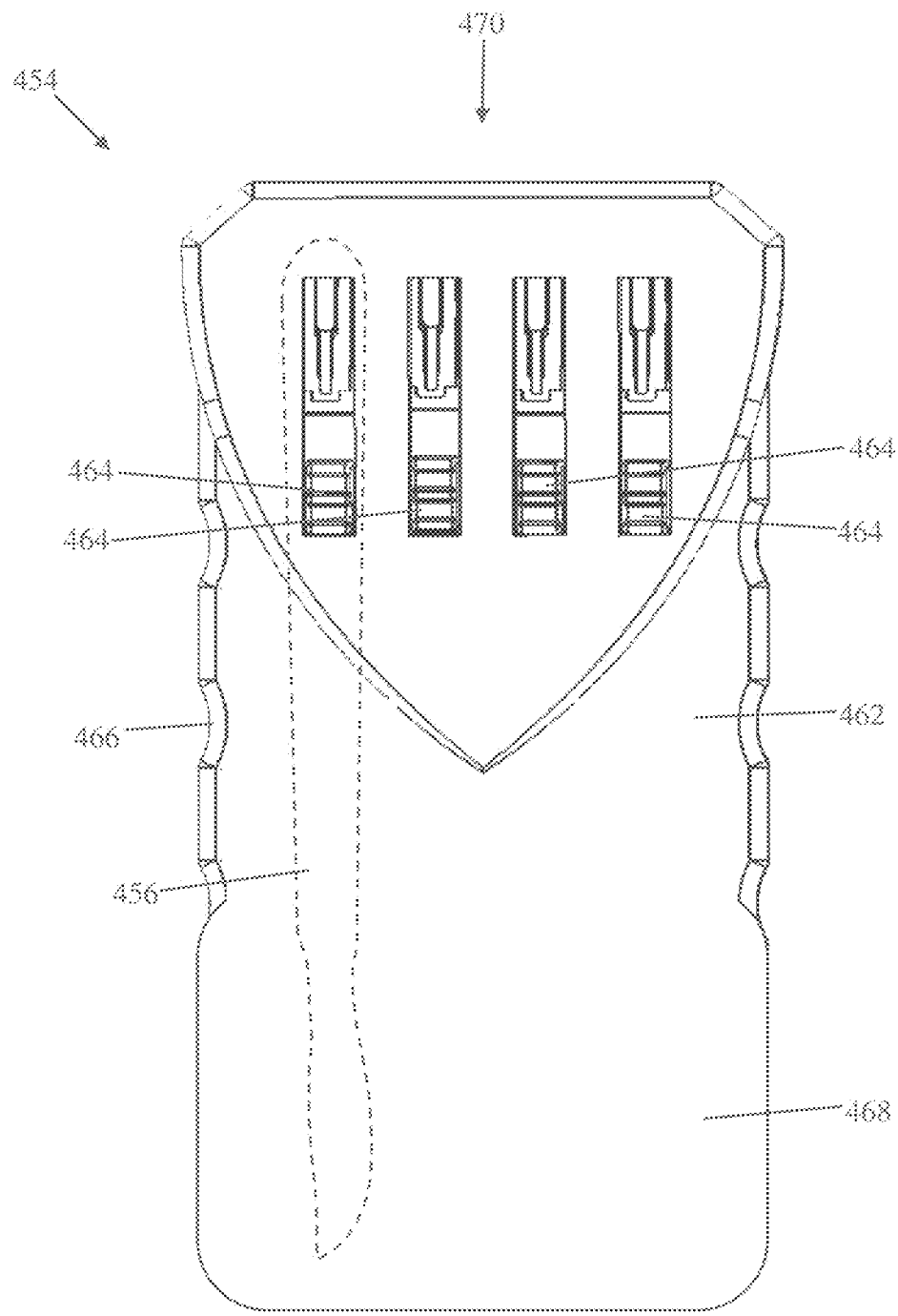
FIG. 25 is a plan view of an alternative example of a safety blade-dispenser of the type shown in FIG. 2 configured to hold an assembled or unitary scalpel (that is, blade and handle)
Figure 26:
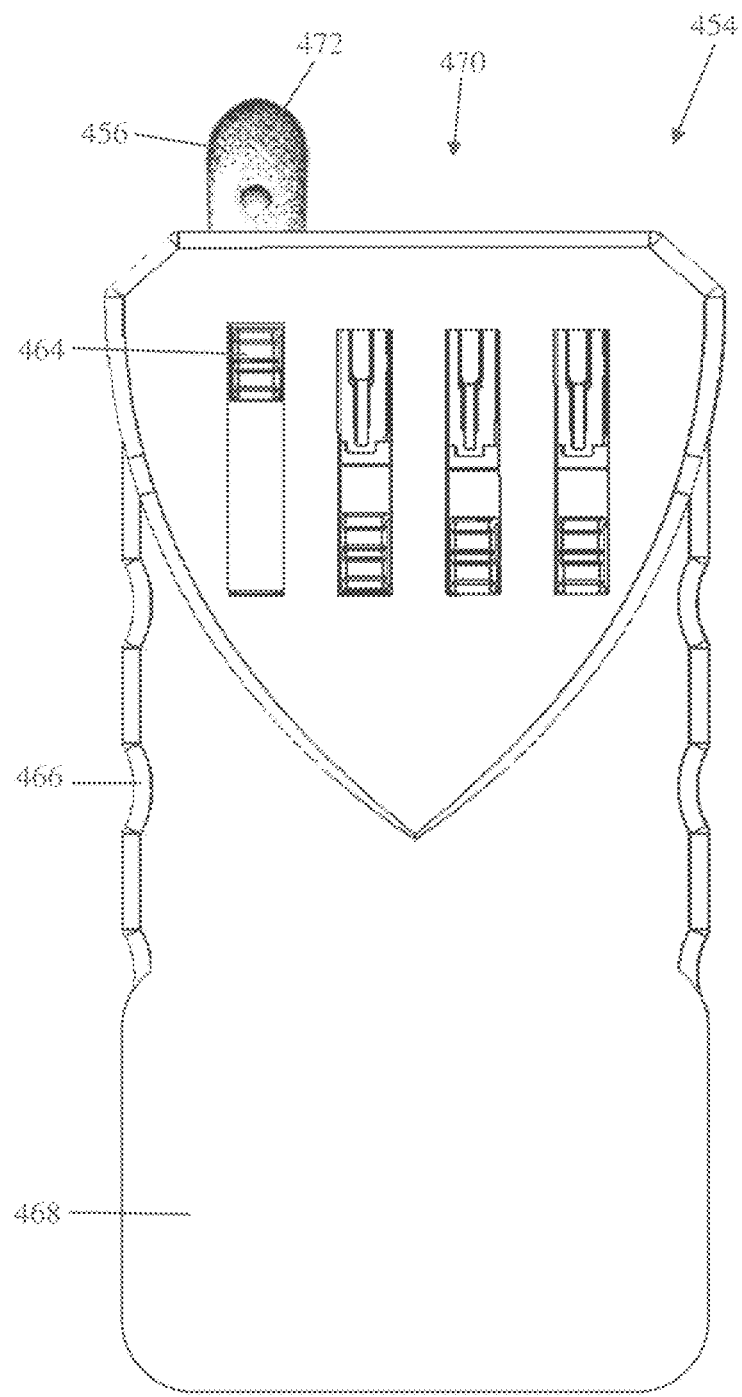
FIG. 26 is a plan view of the safety blade-dispenser of FIG. 23 with one scalpel handle advanced to a removable position.
Figure 27:
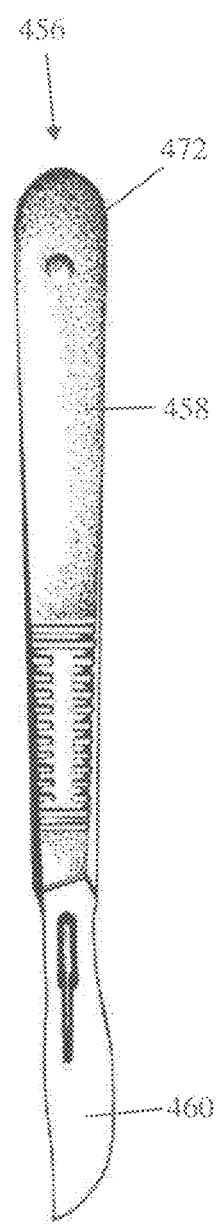
FIG. 27 is a plan view of one example of a scalpel suitable for use with the safety blade-dispenser of FIG. 23.
Figure 28:
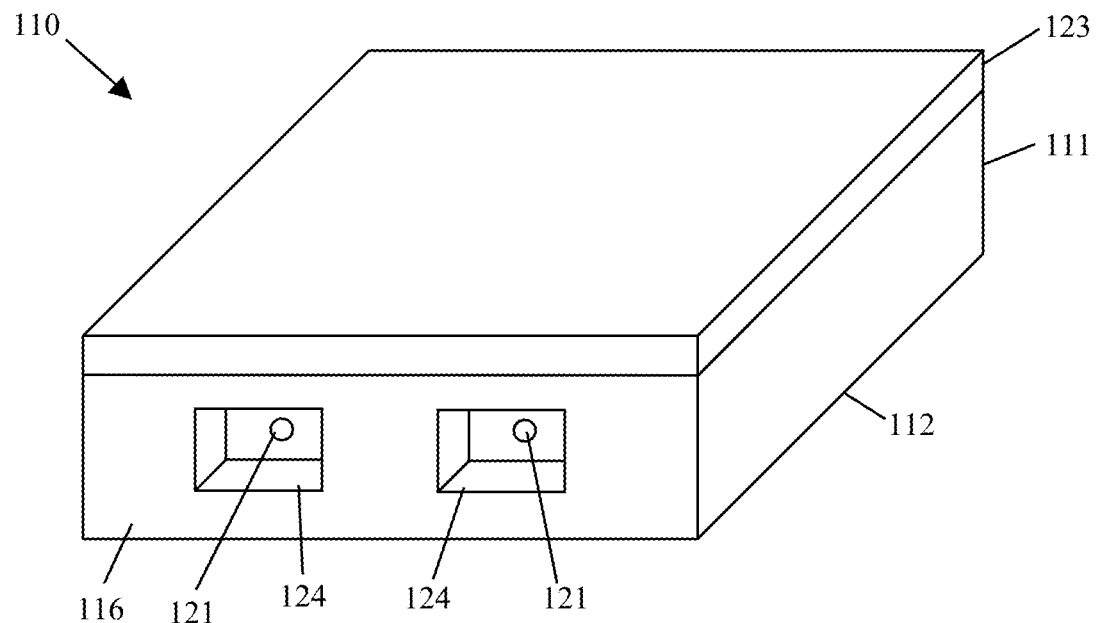
FIG. 28 is a perspective view of a safety-blade dispenser according to another aspect of the present disclosure.

The safety blade-dispenser 14 described above comprises one example of a sharps dispenser that is specifically configured (by way of example) to safely contain and eject surgical sharps 310 in the form of scalpel blades that must be subsequently attached to a handle prior to use in surgery. In some instances, however, it may be beneficial to select and eject a cutting instrument with the blade and handle pre-assembled (or integrally formed). FIGS. 25-26 illustrate one example of a surgical sharps dispenser 454 configured to safely contain and selectively eject one or more larger surgical sharps, such as a complete scalpel 456 including a handle 458 and a blade 460 shown by way of example in FIG. 27.

The surgical sharps dispenser 454 of the present example is similar in form and function to the safety blade-dispenser 14 described above such that identical features will not be described a second time. However it should be understood that any of the features described above in regard to safety blade-dispenser 14, alone or in combination, may be applied to the surgical sharps dispenser 454 without reservation. Generally, the surgical sharps dispenser 454 described herein by way of example comprises a generally rectangular container having a storage portion and a handle portion, the storage portion including four surgical sharps holder assemblies arranged side-by-side in a 1.times.4 matrix configuration. The holder assemblies are slideable in the same direction such that all four surgical sharps are removed on the same side of the device.

The surgical sharps dispenser 454 of the present example includes a housing 462 comprising at least one sharps holder assembly 464 configured to releaseably hold a surgical sharp (e.g. scalpel 456). Preferably, the surgical sharps dispenser 454 includes a plurality of sharps holder assemblies 464. By way of example only, the surgical sharps dispenser 454 described herein includes four sharps holder assemblies 464, however any number of sharps holder assemblies 464 is possible. The sharps holder assemblies 464 are moveable between a first position in which the surgical sharp 456 is fully contained within the housing 462 (e.g. FIG. 23) and a final position in which at least a portion of the surgical sharp 456 is protruding from the housing 462 (e.g. FIG. 24) to enable removal of the surgical sharp 456 from the housing 462. By way of example, the movement may be unidirectional or bidirectional.

The housing 462 is generally compact in size, allowing the surgical sharps dispenser 454 to be held and operated in the palm of a single user's hand, while being large enough to contain and dispense at least one surgical sharp 456. Like the housing 302 of the surgical sharps dispenser 300 described above, the housing 462 is generally rectangular in shape with rounded and/or scalloped edges 466 for ease of gripping. The housing 462 further includes an extended proximal end 468 to accommodate larger surgical sharps such as the scalpels 456 of the present example. The housing 462 further has an interior cavity in which the sharps holder assemblies 464 and surgical sharps 456 reside. The sharps 456 emerge from the interior cavity through openings formed within the distal end 470 of the housing 462, with the proximal end 472 of the scalpel 454 being presented for removal from the sharps holder assembly 464 for subsequent use in the surgical procedure.

Figure 31:
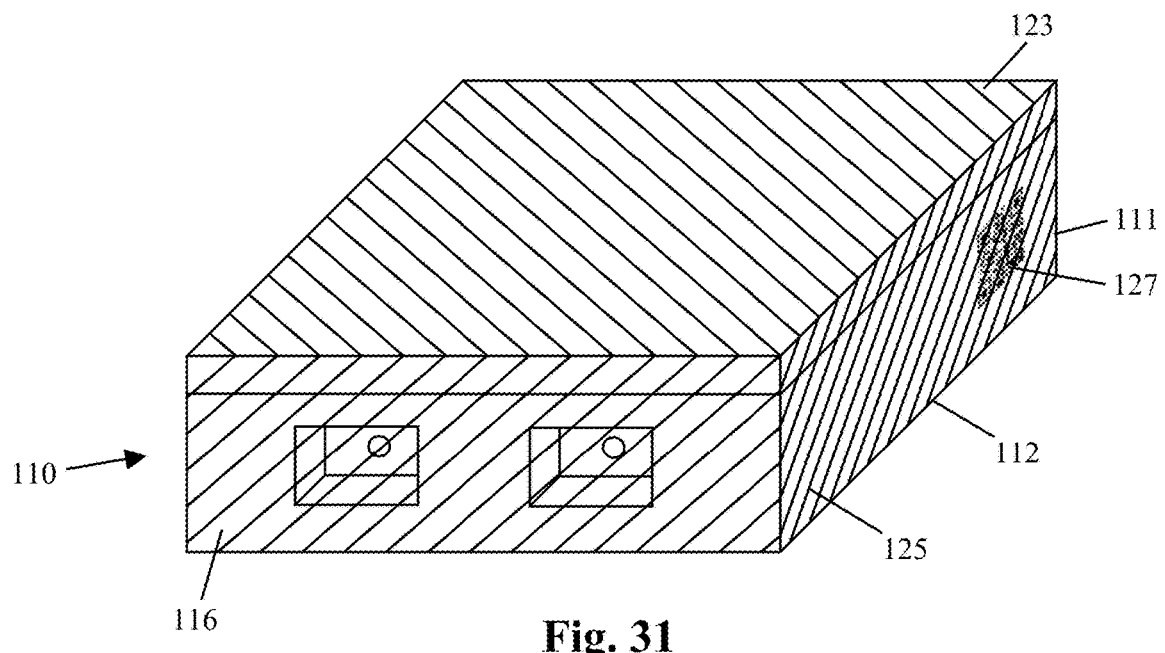
FIG. 31 is a perspective view of the safety-blade dispenser of FIG. 28 with an external covering material and a tracking component.
Figure 32:
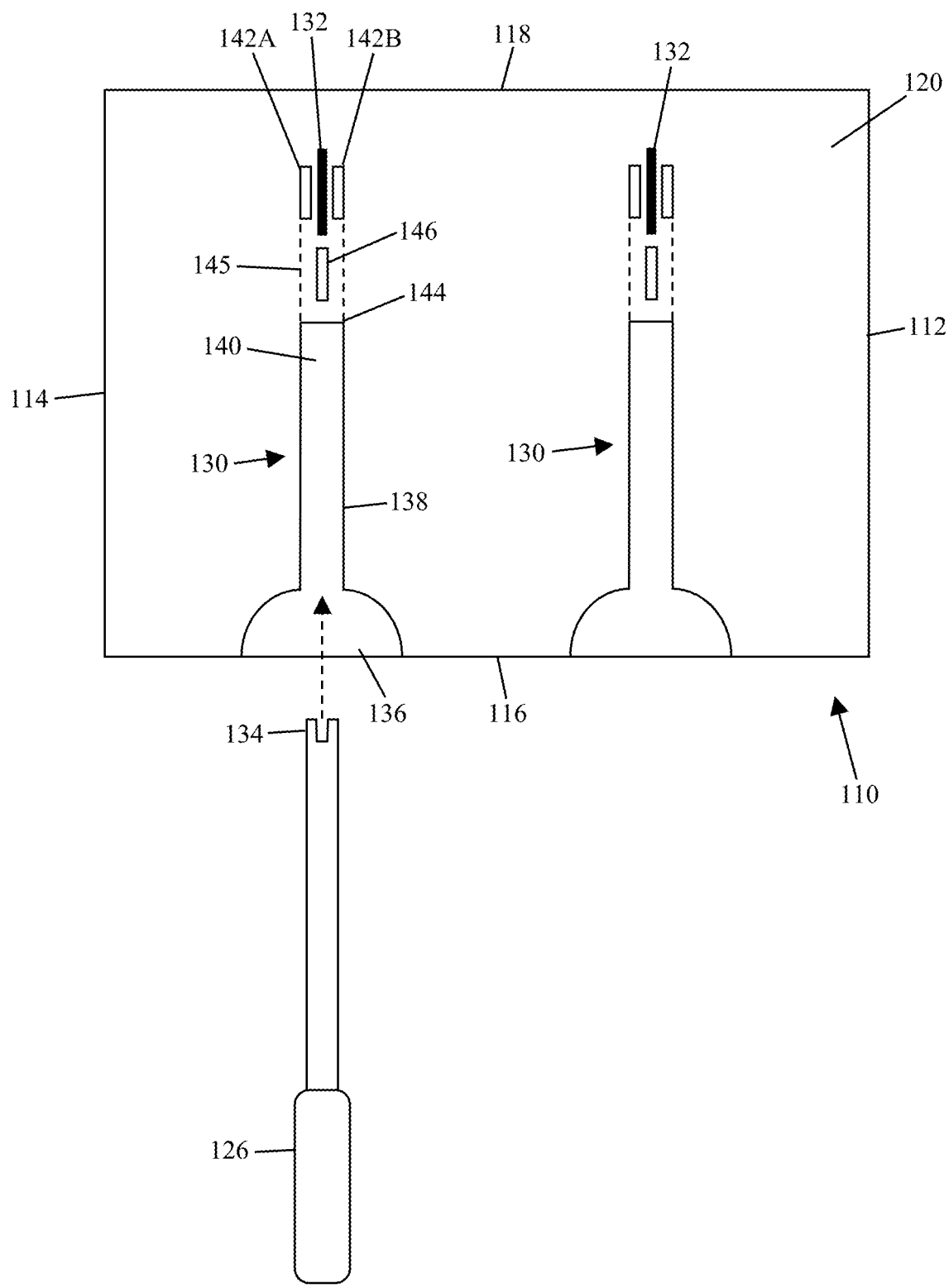
FIG. 32 is a cross-sectional view of the safety-blade dispenser of FIG. 28.

FIGS. 28-33 illustrate an alternate safety-blade dispenser 110 for safely storing surgical blades according to an aspect of the present disclosure. The surgical blade storage container 110 comprises a lower portion 111 comprising a first set of opposing side walls 112 and 114 arranged in a generally parallel orientation, and a second set of opposing end walls 116 and 118. The end walls 116 and 118 are arranged in a generally parallel orientation. A bottom wall 120 connects side walls 112 and 114 and end walls 116 and 118 to form an interior 122, see FIG. 30. The arrangement of the side walls 112, 114, end walls 116, 118, and the bottom wall 120 forms a partially enclosed structure. An upper portion 123 secures to the side walls 112, 114 and end walls 116, 118 to form an enclosed structure. Preferably, the upper portion 123 and the lower portion 111 are sealed together to form a single unit. A material 125, indicated as diagonal lines shown in FIG. 31, may be used to maintain the surgical blade storage container 110 as a sterile component. The material 125 may be a sterile plastic or paper wrap sized and shaped to cover the entire surgical blade storage container 110. Alternatively, the material 125 may be applied to one or more portions of the surgical blade storage container 110. The surgical blade storage container 110 may further include a tracking mechanism or monitoring mechanism. As seen in FIG. 31, positioned on side wall 112 is a tracking and/or monitoring mechanism using, for example, a data capture and/or display device or system or other digital information options, illustrated herein as a Quick Response Code (QR code) 127. Alternatively, a bar code (an optical machine-readable representation of data) such as a Universal Product Code (UPC) may be used. The QR code can be programmed with various patient identifying information similar to that of the labels described previously, including the patient name or other identification means, type of surgery, site of surgery, and physician name. As such, when a physician or medical support team member scans the QR code 127 with a bar code reader, scanner, or camera, they will be able to view the information. The surgical blade storage container 110 may also utilize an alternative embodiment of a tracking and/or monitoring mechanism, such as radio-frequency identification (RFID) transponder.

The RFID transponder generally comprises a chip for storage and/or processing, an antenna for transmitting and receiving information, and an inlay for supporting the chip and antenna. While any RFID transponder known to one of skill in the art may be used, the RFID transponder may be an active tag having a battery which runs the microchip circuitry or a passive tag without a battery and using a RFID reader which is designed to send electromagnetic waves to induce the tag's antenna to power the microchip circuitry. The transponder may be a read-only tag which contains data pre-written thereon, a write-once tag which allows the user to write data to the tag one time, or a full read and write tag which enables the user to write new data to the transponder as needed. The inlay may be a substrate film which can support and hold the chip and antenna. Alternatively, the inlay can be a label or tag having self-adhesion coating to ensure that the RFID chip and antenna adhere to a surface. The inlay may be embedded in plastic castings or casted in polyurethane resin coating.

Referring back to FIG. 28, the surgical blade storage container 110 comprises at least one surgical blade inlet entrance 124, illustrated herein as a recessed or set back region. The at least one surgical blade inlet entrance 124 contains an opening 121 which allows a blade handle 126 (see FIG. 32) to move through end wall 116 and into and out of the interior region 122. The at least one surgical blade inlet entrance 124 is sized and shaped to allow at least a portion of the surgical blade handle 126 to fit within upon insertion. In addition, the at least on surgical blade inlet entrance 124 may also be sized and shaped to accommodate a blade handle having a surgical blade attached thereto upon removal. The opening 124 leads to a guide member, referred to generally as a surgical blade handle guide 130. The surgical blade handle guide 130 is designed to guide at least a portion of the surgical blade handle 126 to a surgical blade 132 stored within. As such, upon insertion of the surgical blade handle 126, the distal end 134, i.e. the end which connects to, and holds a surgical blade, is automatically guided to where the surgical blade is positioned, thereby preventing the user from direct contact with the surgical blade upon connection.

Figure 29:
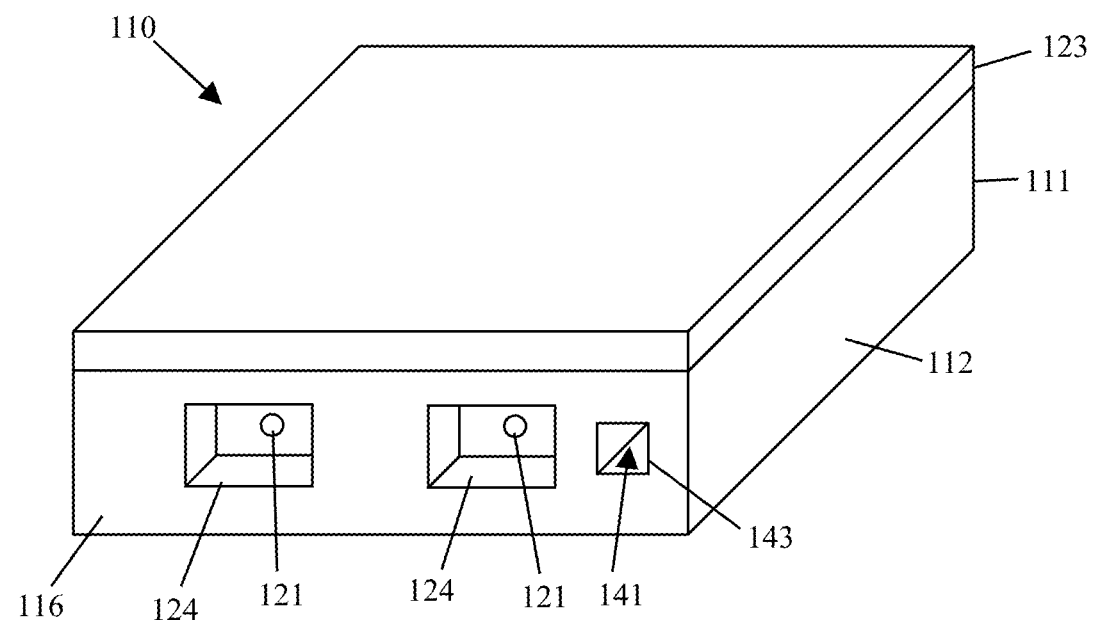
FIG. 29 is a perspective view of the safety-blade dispenser of FIG. 28 with an optional feature of a blade handle recess according to an aspect of the present disclosure.
Figure 30:
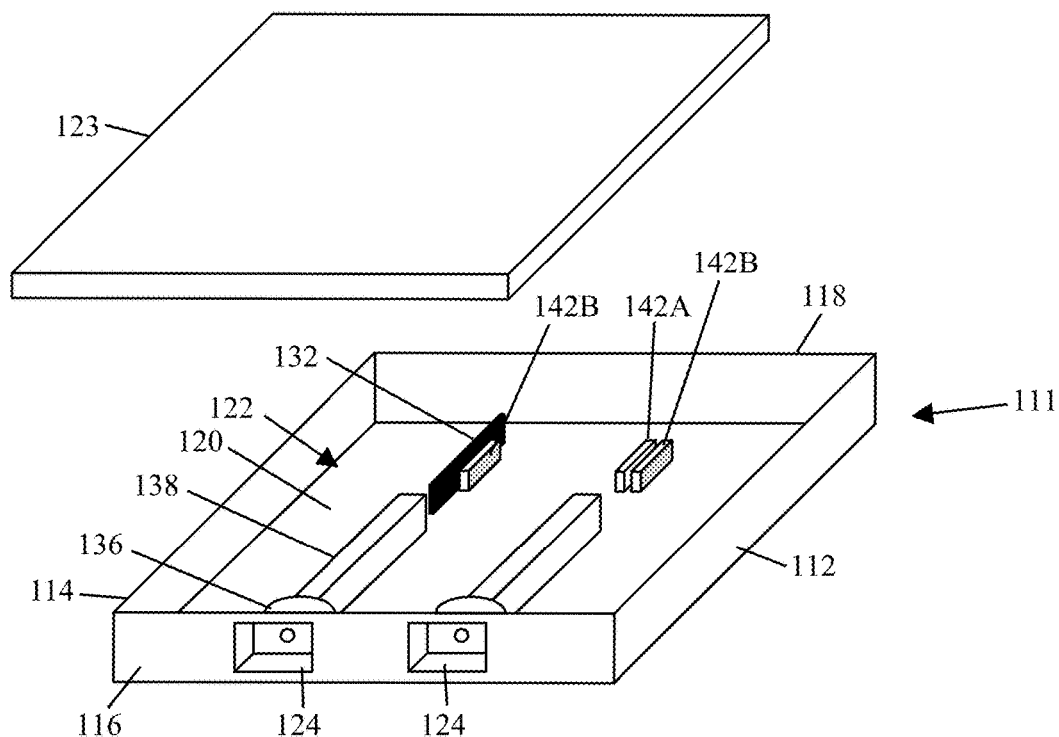
FIG. 30 is an exploded view of the safety-blade dispenser of FIG. 28.
Figure 33:
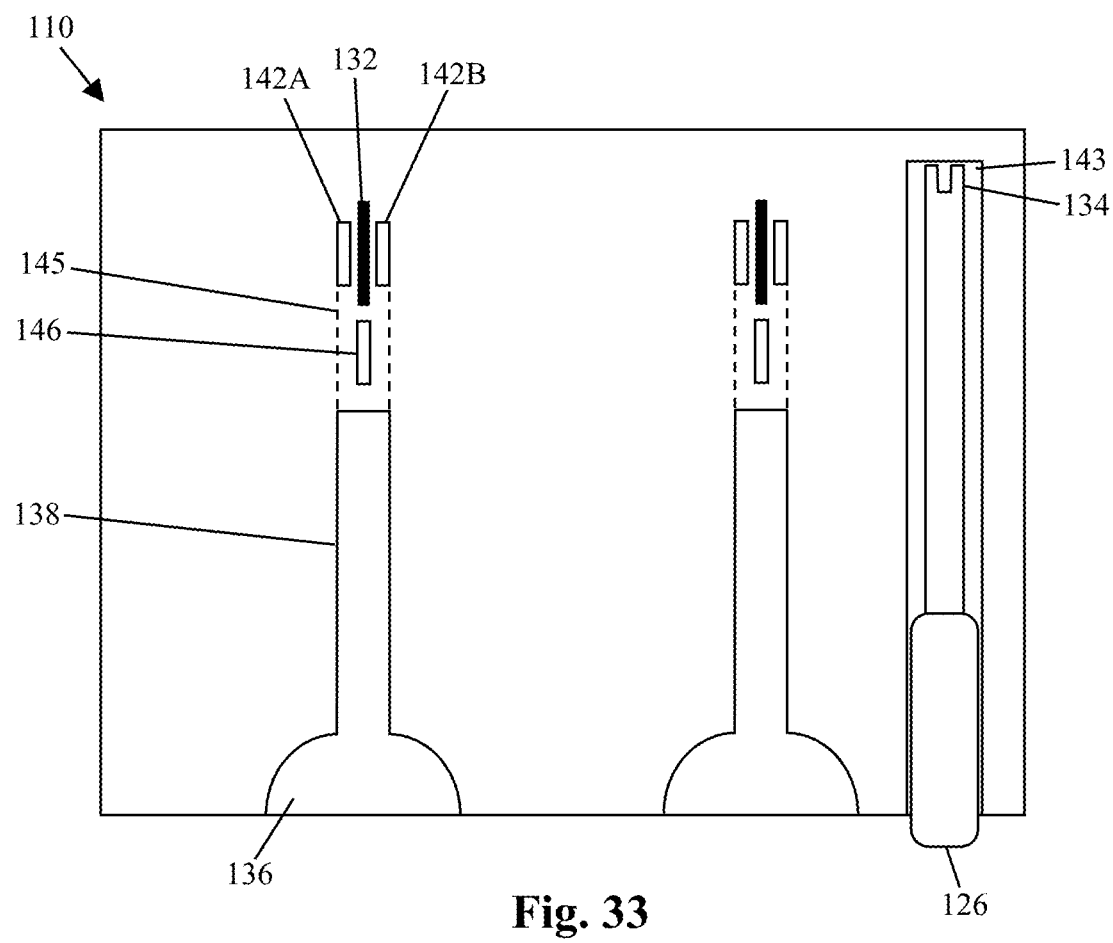
FIG. 33 is a cross-sectional view of the safety-blade dispenser of FIG. 29.

FIG. 29 illustrates the surgical blade storage container 110 having an additional feature of a surgical blade handle storage lumen 141 (see also FIG. 33). The surgical blade handle storage lumen 141 is sized and shaped to receive and store the surgical blade handle 126 (see FIG. 33) through opening 143.

The surgical blade handle guide 130 contains a blade inlet 136. The blade inlet 136 is sized and shaped to guide the surgical blade handle 126 towards a blade channel 138. The blade inlet 136, therefore, may be configured to contain a larger outer area which is directed towards or is angled towards the blade channel 138. Such arrangement allows the user a greater degree of freedom to insert the surgical blade handle into the at least one surgical blade inlet entrance 124 and the blade inlet 36 and ensure alignment with the surgical blade 132. The blade channel 138 is shown as an elongated tubular structure having an interior lumen 140 constructed to receive at least a portion of the surgical blade handle 126 to provide further guidance towards the surgical blade 132.

As the at least a portion of the surgical blade handle 126 moves through the blade inlet 136, the at least a portion of the surgical blade handle 126 is directed to the surgical blade so that the surgical blade handle distal end 134 aligns with a portion of the surgical blade that connects thereto. The surgical blade 132 may contain one or more maintenance structures, illustrated as walls 142A and 142B, which maintain the surgical blade 132 in a proper orientation or location, such as parallel to wall 120, at an angle to wall 120, or in alignment with an open end 144 of the blade channel 138. If required, a blade coupler 146 may be positioned between the distal end of the blade channel 138 and the surgical blade 132. The blade channel 138 may be sized to allow a gap between the distal open end 144 and the surgical blade 132, or may run up to the surgical blade 132 or maintenance structures 142A or 142B, see dashed lines 45.

Figure 34:
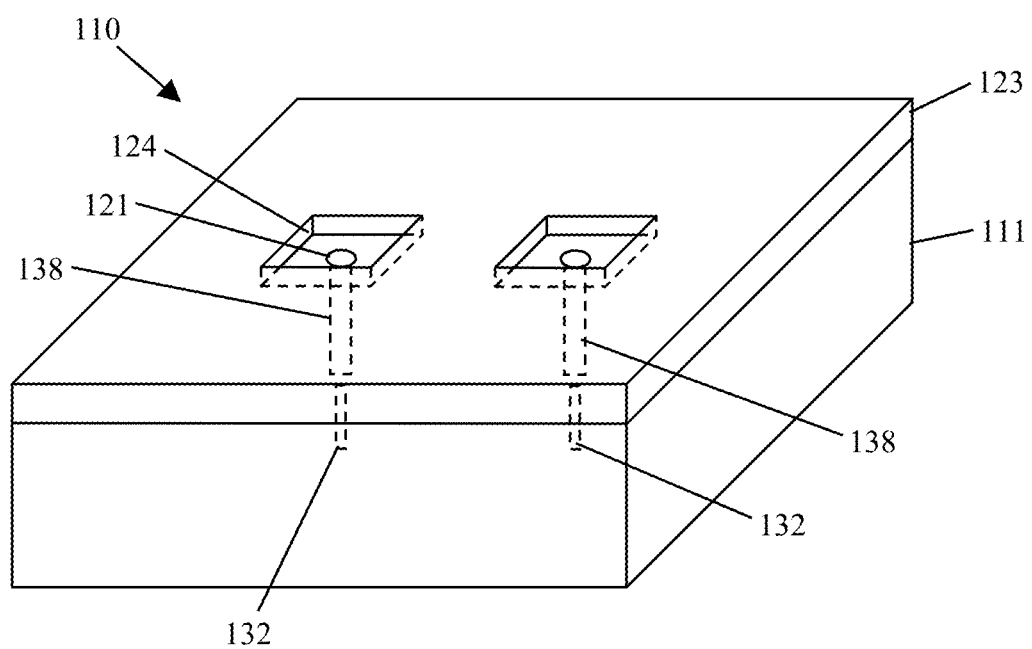
FIG. 34 is a perspective view of a safety-blade dispenser of the type shown in FIG. 28, with alternative placement of the blade inlets.
Figure 35:
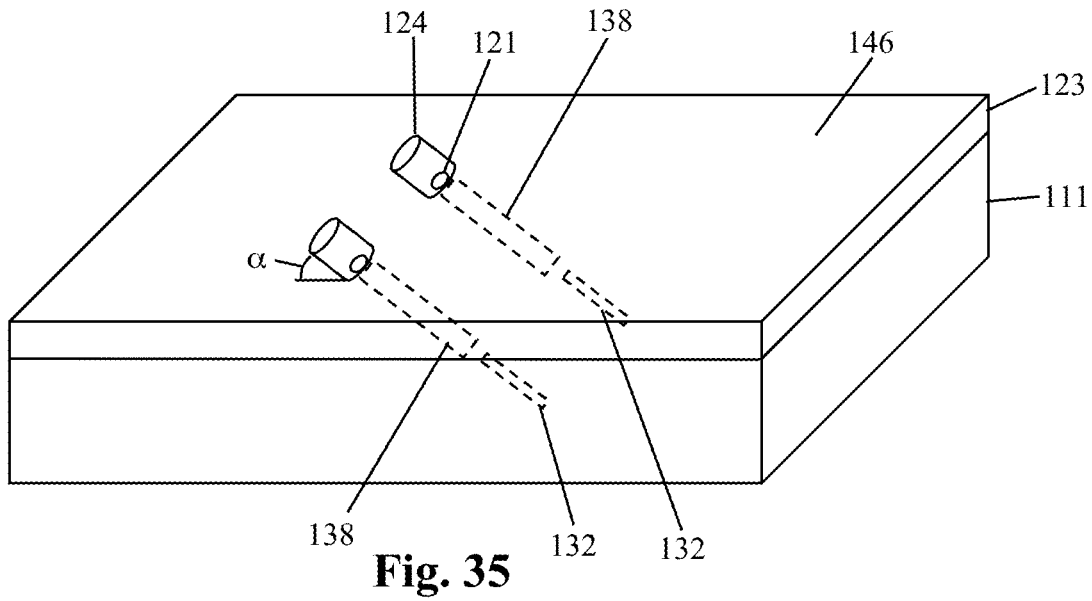
FIG. 35 is a perspective view of a safety-blade dispenser of the type shown in FIG. 28, with alternative placement of the blade inlets.

FIGS. 34-37 illustrate the surgical blade storage container 110 having the at least one surgical blade inlet entrance 124 arranged in different locations or orientations. FIG. 34 shows the at least one surgical blade inlet entrance 124 located on the upper portion 111. In this orientation, the surgical blade handle guide 130 would be arranged in a perpendicular orientation (as opposed to a parallel orientation) relative to wall 120. The surgical blade 132 would be arranged in a perpendicular orientation (as opposed to a parallel orientation) relative to wall 120 as well. FIG. 35 illustrates the at least one surgical blade inlet entrance 124 extending upwardly and outwardly from the outer surface 146 of the upper portion 111. Preferably, the at least one surgical blade inlet entrance 124 is oriented at an angle, .alpha., from the outer surface 146 of the upper portion 111. In this orientation, the surgical blade handle guide 130 would be arranged at an angle (as opposed to a parallel or perpendicular orientation) relative to wall 120. The surgical blade 132 would be arranged at an angle (as opposed to a parallel or perpendicular orientation) relative to wall 120 as well.

Figure 36:
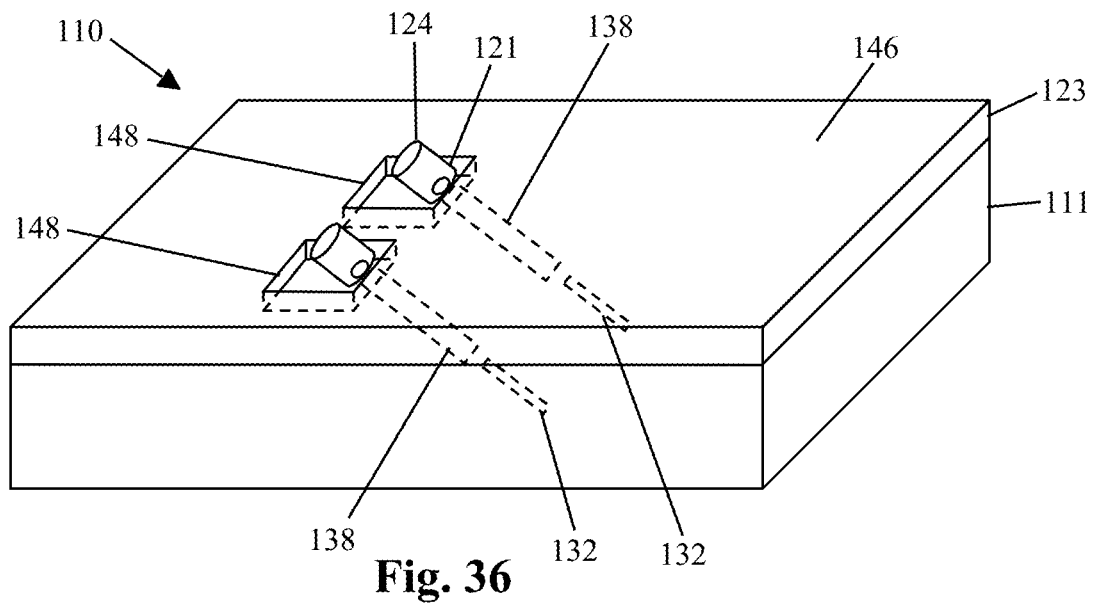
FIG. 36 is a perspective view of a safety-blade dispenser of the type shown in FIG. 28, with rotatable blade inlets shown oriented in a blade-insertion position.
Figure 37:
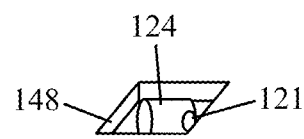
FIG. 37 is a perspective view of rotatable blade inlets shown oriented in a non-insertion position of a safety-blade dispenser of the type shown in FIG. 28.

FIGS. 36-37 illustrate an embodiment of the surgical blade storage container 110 in which the at least one surgical blade inlet entrance 124 rotates or pivots between an open position, FIG. 36, to allow insertion of the surgical blade handle 126, and a closed position, FIG. 37, which prohibits insertion of the surgical blade handle 126. The outer surface 146 of the upper portion 111 may contain a recessed region 148 sized and shaped to accommodate the at least one surgical blade inlet entrance 124 when in the closed position, thereby allowing the at least one surgical blade inlet entrance 124 to be flush with or positioned below the outer surface 146.

Figure 38:
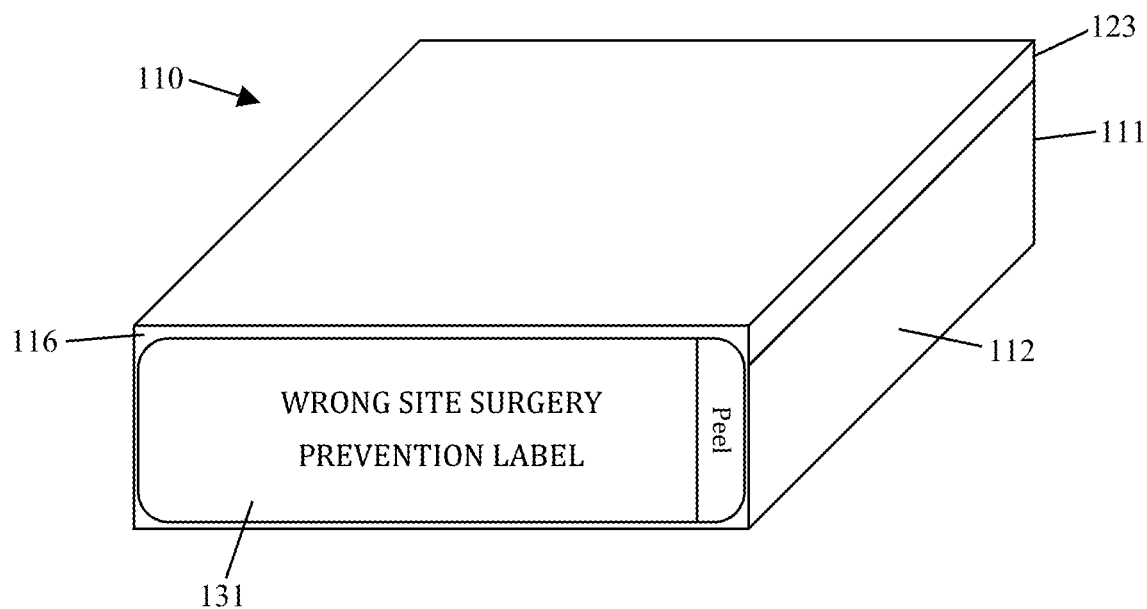
FIG. 38 is a perspective view of a safety-blade dispenser of the type shown in FIG. 28, with a wrong-site surgery prevention label attached to an end wall to cover the blade inlets.

The surgical blade storage container may include a confirmation and signature label 131 (see FIG. 38). The label 131 is removable and covers the at least one surgical blade inlet entrance 124 so access to the surgical blade 132 stored within the surgical blade storage container 110 cannot be obtained until the label is removed. In the embodiment shown in FIG. 38, the confirmation and signature label 131 has a front side that can be written upon and that includes a checklist to be filled out by the surgical technician, in addition to fields where surgical team members sign after confirming that the information entered in the checklist is correct. For example, the checklist preferably provides for confirming the correctness of the patient name, the type/name of the surgical procedure, the laterality of the incision (left, right, or no laterality), and the laterality of the pathology (left, right, midline, or no laterality), and for confirming that the proper instrumentation and any surgical implants are present and accounted for. It will be understood that the confirmation and signature label 131 may be customized for the same or other surgical uses, and thus is not limited to the specific representation depicted herein. Thus, in alternative embodiments, the checklist may call for the same surgery-related information of the depicted embodiment, only some of this information, or additional information.

Preferably, the confirmation and signature label 131 is adhesive-backed and has a pull tab so that it can be easily removed from the surgical blade storage container 110 and, if desired, placed in the medical record (the patient's record/chart/file) after it has been signed and removed. The confirmation and signature label 131 must allow at least the surgeon, or other surgical team members, to fill in the surgical-site information within an input field of the label, i.e. the surgical-site information to conduct a pre-surgery assessment confirming the correct surgical site.

The surgical blade storage container 110 can be configured to provide easy and rapid visualization using a visual indicator to alert the surgical team as to which side (left or right), sometimes referred to as "laterality", of the patient for which a surgical procedure is to take place. All or some portion of the surgical blade storage container 110 may have a color coding of some shade of red, for example as a pink/rose color, to indicate a right side surgical procedure. All or some portion of the surgical blade storage container 110 may have a color coding of some shade of a purple based color, preferably a lavender color, to indicate a left side surgical procedure. Alternative visual indicators may include symbols, letters, words or phrases. In any embodiment, the surgeon or surgical team member can easily ensure that the position of the surgical site or laterality aligns with the color of the container. Gray can be used to indicate neutrality, or no laterality.

Figure 39:
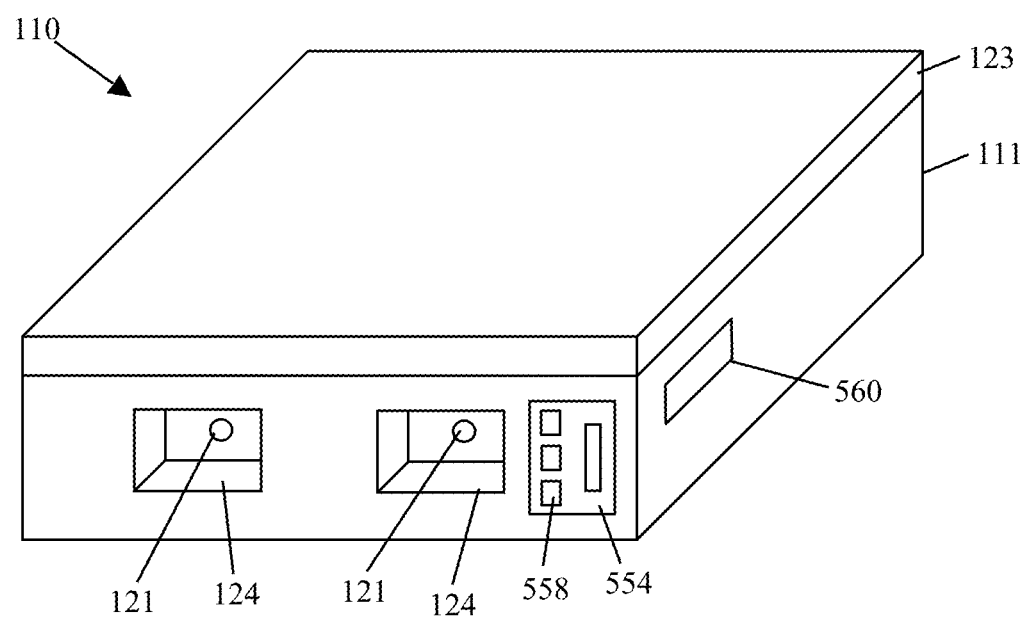
FIG. 39 is a perspective view of a safety-blade dispenser of the type shown in FIG. 28 modified to have a central control unit.
Figure 40:
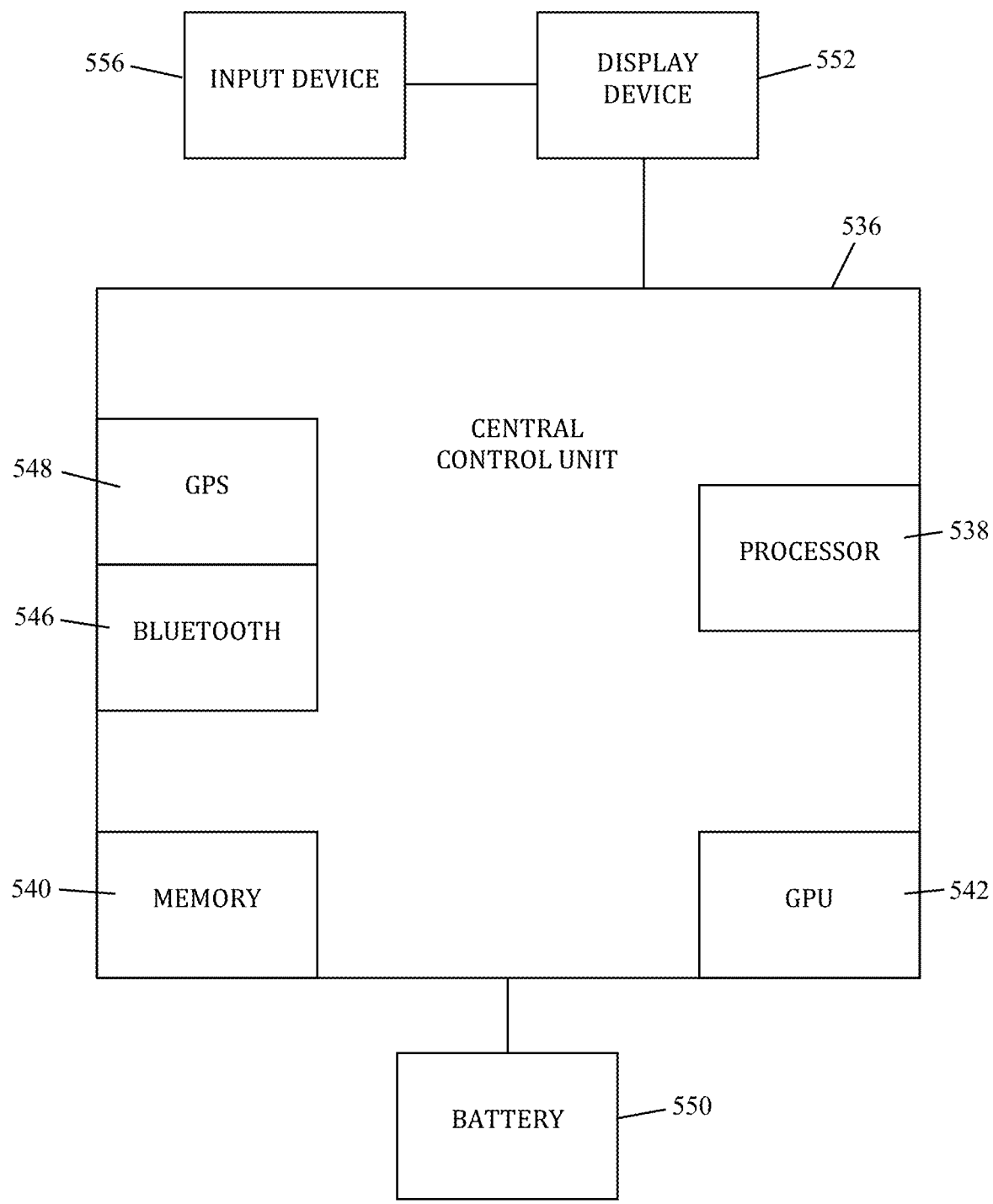
FIG. 40 is a schematic diagram of the components of an illustrative example of a central control unit shown generally in FIG. 39.
Figure 41:
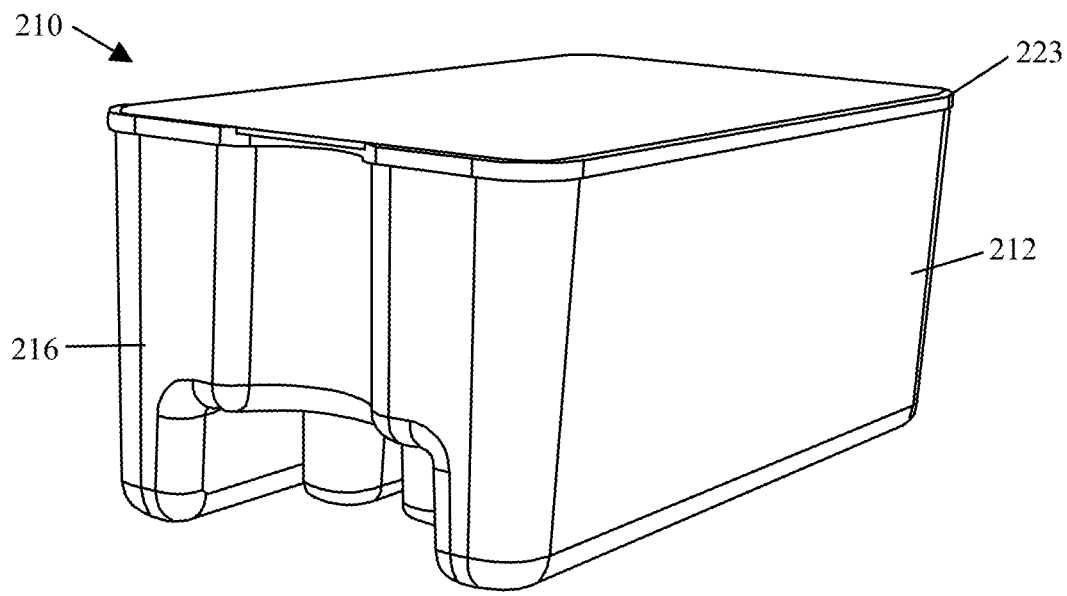
FIG. 41 is a perspective view of an alternate safety-blade dispenser according to the present disclosure.
Figure 42:
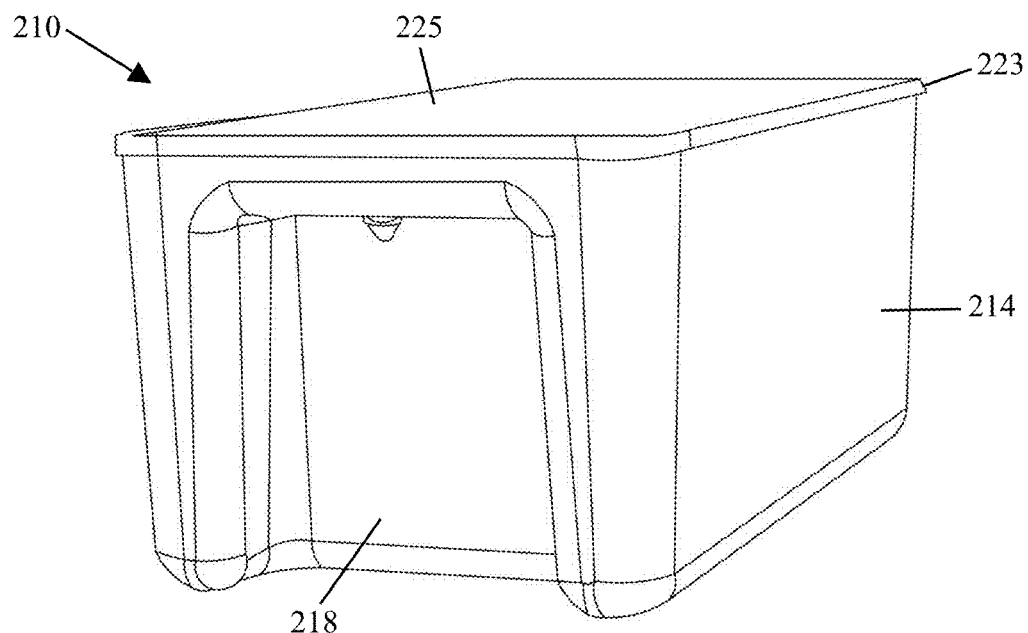
FIG. 42 is an alternative perspective view of the safety-blade dispenser shown in FIG. 41.
Figure 43:
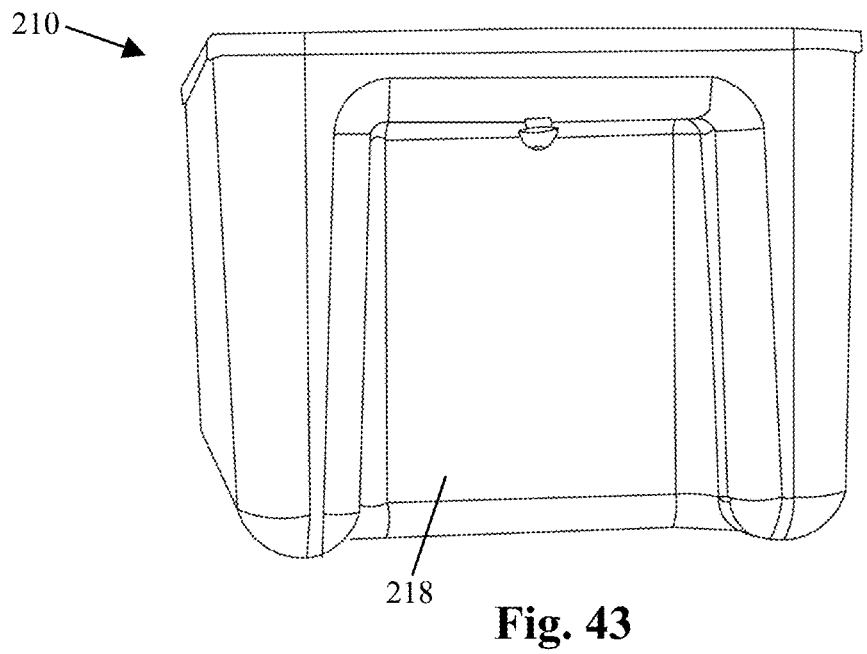
FIG. 43 is a front view of the safety-blade dispenser shown in FIG. 41.
Figure 44:
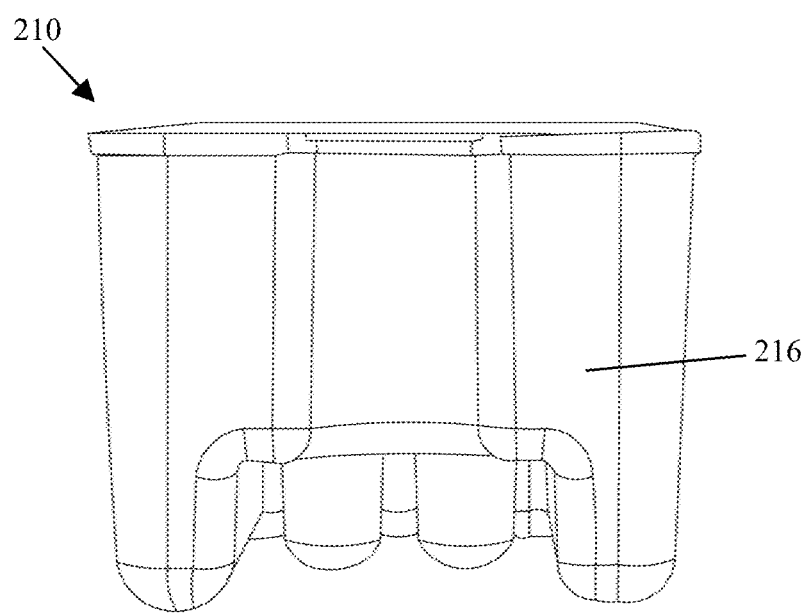
FIG. 44 is a back view of the safety blade container illustrated in FIG. 41.
Figure 45:
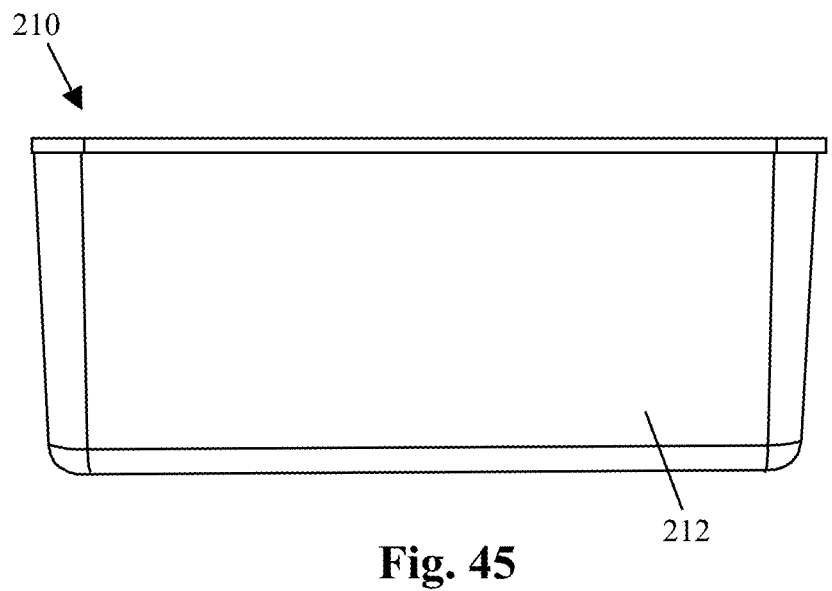
FIG. 45 is a left side view of the safety blade container illustrated in FIG. 41.
Figure 46:
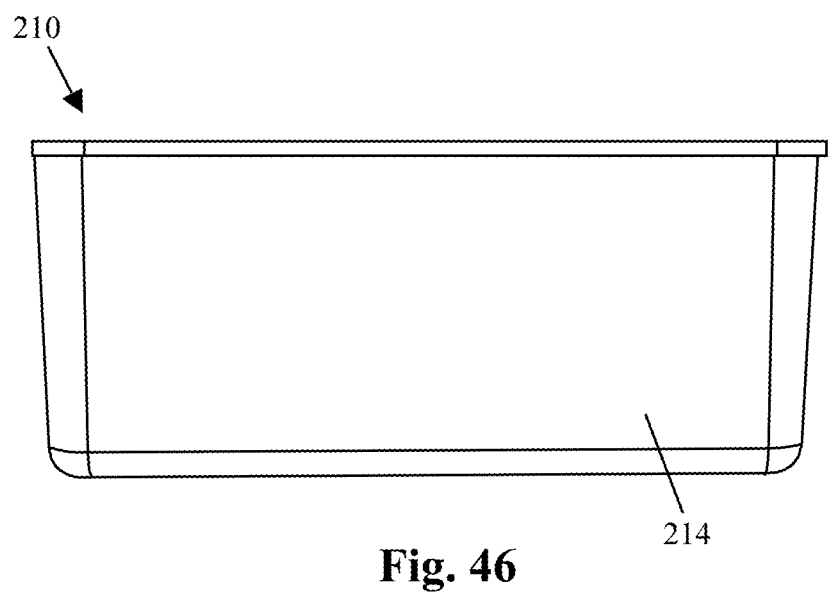
FIG. 46 is a right side view of the safety blade container illustrated in FIG. 41.
Figure 47:
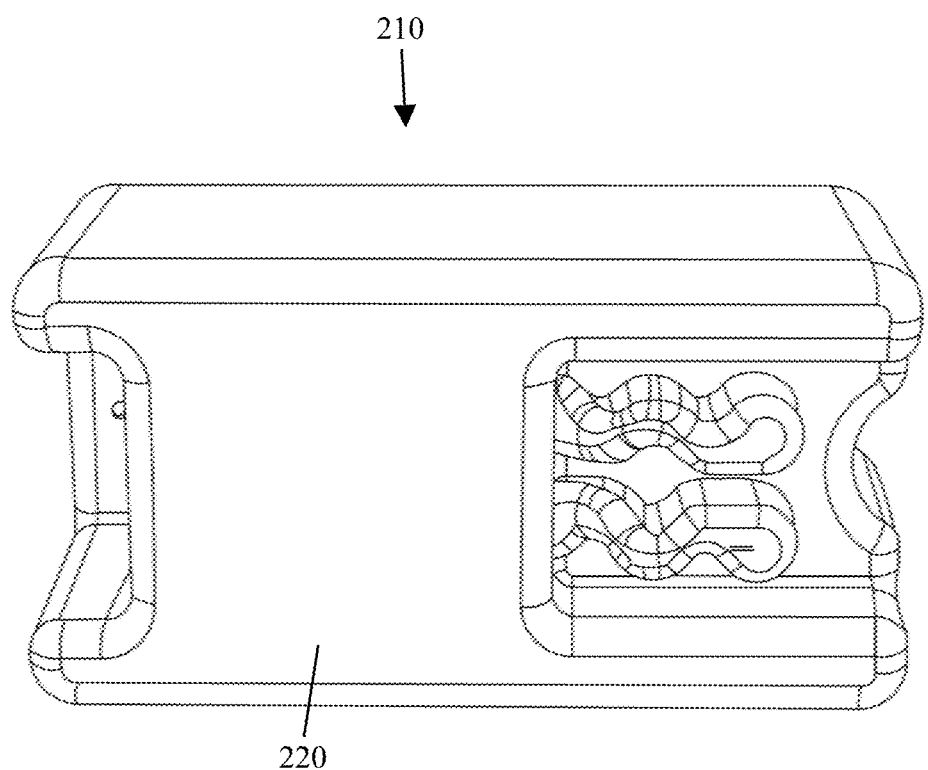
FIG. 47 is a bottom view of the safety blade container illustrated in FIG. 41.
Figure 48:
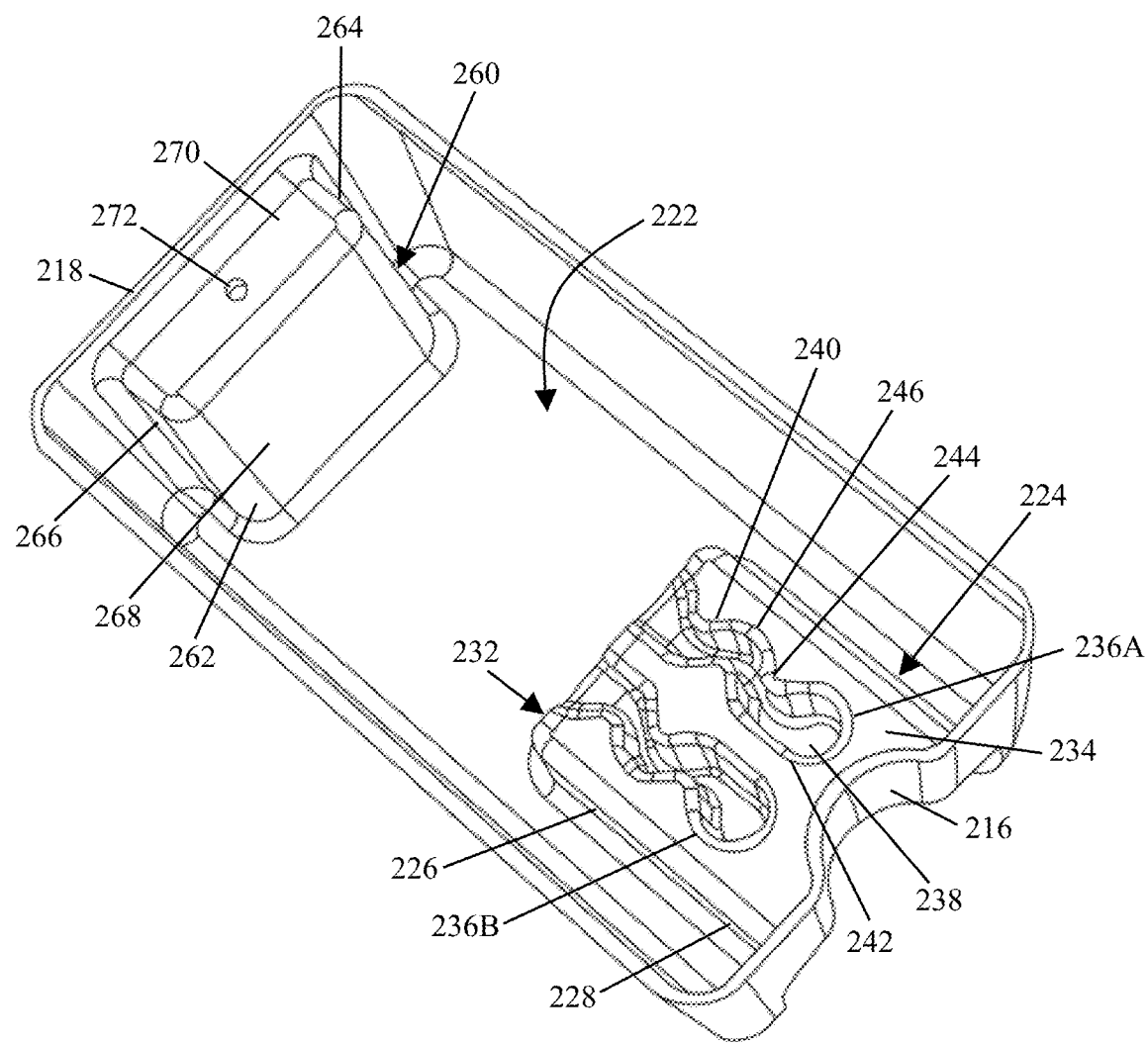
FIG. 48 illustrates the interior of the safety blade container illustrated in FIG. 41.

FIGS. 39 and 40 illustrate the surgical blade storage container 110 converted to a "smart" container. The cover 123 is adapted to include a central control unit 536 including, for example, a processor 538, memory 540, graphic processing unit 542, GPS functioning 548, and Bluetooth wireless capability 546. The central control unit 536 can be powered by a battery 550 and electrically connected to a display unit 552, such as an LED screen 554, see FIG. 39. Data input devices, such as buttons 558 or a keyboard (not shown), may be included to allow the user to input data. The surgical blade storage container 110 may also contain a connection point, illustrated herein as a USB port 560 to allow for transfer of data from the central control unit 536 to a flash drive or a computer system via cables.

The surgical blade storage container 110 can be used in any surgical procedure as a standalone device. In addition, the surgical blade storage container 110 may be a component in a system or method of preventing wrong site surgeries, such as that shown and described in the '210 PCT referenced above.

FIGS. 41-48 illustrate a safety-blade dispenser 210 for safely storing surgical blades according to yet another aspect of the present disclosure. The safety-blade dispenser 210 comprises a lower portion comprising a first set of opposing side walls 212 and 214 arranged in a generally parallel orientation, and a second set of opposing end walls 216 and 218. The end walls 216 and 218 are arranged in a generally parallel orientation. A bottom wall 220 connects side walls 212 and 214 and end walls 216 and 218 to form an interior region 222, see FIG. 48. The arrangement of the side walls 212, 214, end walls 216, 218 and the bottom wall 220 forms a partially enclosed structure. An upper portion, illustrated herein as a cover 223, secures to the side walls 212, 214 to form an enclosed structure. A material 225, such as a removable label, is placed on top of the cover 223. The label may also include a tracking mechanism. As see in FIG. 53, positioned on or with the surgical blade storage container 110 is a tracking and/or monitoring mechanism using, for example, a data capture and/or display device or system or other digital information options, illustrated herein as a Quick Response Code (QR code) 227. Alternatively, a bar code (an optical machine-readable representation of data) such as a Universal Product Code (UPC) maybe used. The QR code can be programmed with various patient identifying information similar to that of the labels described previously, including the patient name or other identification means, type of surgery, site of surgery, and physician name. As such, when a physician or medical support team member scans the QR code 227 with a bar code reader, scanner, or camera, they will be able to view the information. The surgical blade storage container 210 may also utilize an alternative embodiment of a tracking and/or monitoring mechanism, such as a radio-frequency identification (RFID) transponder.

The RFID transponder generally comprises a chip for storage and/or processing, an antenna for transmitting and receiving information, and an inlay for supporting the chip and antenna. While any RFID transponder known to one of skill in the art may be used, the RFID transponder 530 may be an active tag having a battery which runs the microchip circuitry, or a passive tag without a battery and using a RFID reader which is designed to send electromagnetic waves to induce the tag's antenna to power the microchip circuitry. The transponder may be a read-only tag which contains data pre-written thereon, a write-once tag which allows the user to write data to the tag one time, or a full read and write tag which enables the user to write new data to the transponder as needed. The inlay may be a substrate film which can support and hold the chip and antenna. Alternatively, the inlay can be a label or tag having self adhesion coating to ensure that the RFID chip and antenna adhere to a surface. The inlay may be embedded in plastic castings or casted in polyurethane resin coatings.

The surgical system contains the surgical blade storage container 210 which is preferably adapted to be trackable and/or can electronically communicate with other components of the system. The ability to be trackable and/or electronically communicate with other components of the system allows the users of the surgical procedure the ability to continuously monitor and check that the scheduled surgical procedures for a patient is correct, thereby extending the prevention of wrong site surgeries to multiple patient-medical representatives interactions.

The material 223 is removable and covers the lock member (to be described later) so access to unlock the surgical blade storage container 210 until the label is removed is prevented. In one embodiment, for example, the confirmation and signature label 131 has a front side that can be written upon and that includes a checklist to be filled out by the surgical technician, and fields where surgical team members sign after confirming that the information entered in the checklist is correct. For example, the checklist preferably provides for confirming the correctness of the patient name, the type/name of the surgical procedure, the laterality of the incision (left, right, or no laterality), and the laterality of the pathology (left, right, midline, or no laterality), and for confirming that the proper instrumentation and any surgical implants are present and accounted for. It will be understood that the confirmation and signature label 216 may be customized for the same or other surgical uses, and thus is not limited to the specific representation depicted herein. Thus, in alternative embodiments, the checklist may call for the same surgery-related information of the depicted embodiment, only some of this information, or additional information. Preferably, the confirmation and signature label 231 is adhesive-backed and has a pull tab so that it can be easily removed from the container 212 and, if desired, placed in the medical record (the patient's record/chart/file) after it has been signed and removed. The confirmation and signature label 231 must allow at least the surgeon, or other surgical team members, to fill in the surgical-site information within an input field of the label, i.e. the surgical-site information to conduct a pre-surgery assessment confirming the correct surgical site.

The interior 222 of the surgical blade storage container 210 is configured to provide a mechanism to secure a surgical instrument, such as a surgical blade, therein in a predetermined orientation. Positioned towards the end wall 216 is a surgical instrument holding member 224. While the surgical instrument holding member 224 is shown configured to hold two surgical instruments, such number is illustrative only as the surgical instrument holding member 224 can be configured to hold one surgical instrument or more than two surgical instruments.

The surgical instrument holding member 224 comprises a main body 226 formed by a plurality of side walls 228, 230, 232 and an upper wall 234. Two surgical instrument receiving areas 236A and 236B are configured to receive and hold a surgical instrument. Surgical instrument receiving area 236A comprises an open slotted channel 238 defined by a first wall 240 and a second opposing wall 242. Each of the walls 240 and 242 are irregularly shaped to contain a plurality of concave portions 244 directed inwardly, or towards the slotted channel 238, and convex portions 246 directed outwardly, or away from the slotted channel 238. As shown in the figure, each wall 242 or 244 has a plurality of concave portions 244 and convex portions 246. In some areas of the surgical instrument receiving area 236A, where a concave portion 244 is formed in one wall, a corresponding convex portion is 246 is formed in the opposite wall. In this manner, one or more concave portions 244 align with one or more convex portions 246. The concave portions 244 in each of the walls 240 and 242 provide contact points for maintaining the positioning or orientation of surgical equipment placed within the surgical instrument receiving area 236A.

Figure 49:
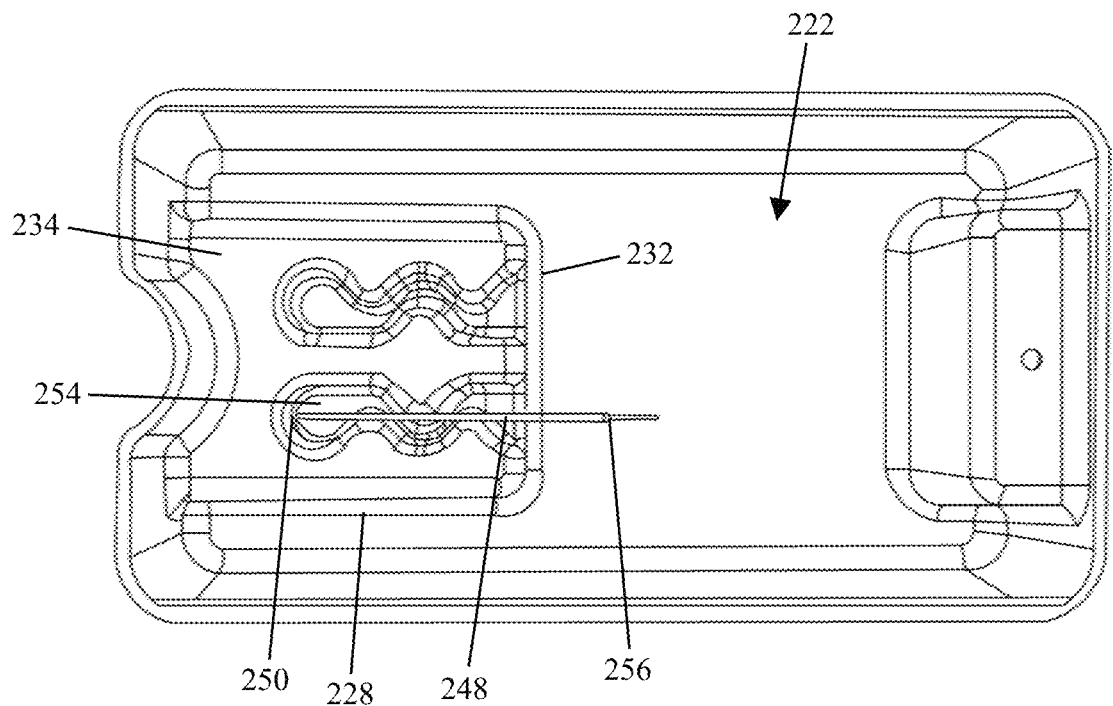
FIG. 49 illustrates the interior of the safety blade container illustrated in FIG. 41 and having a surgical blade secured therein.
Figure 50:
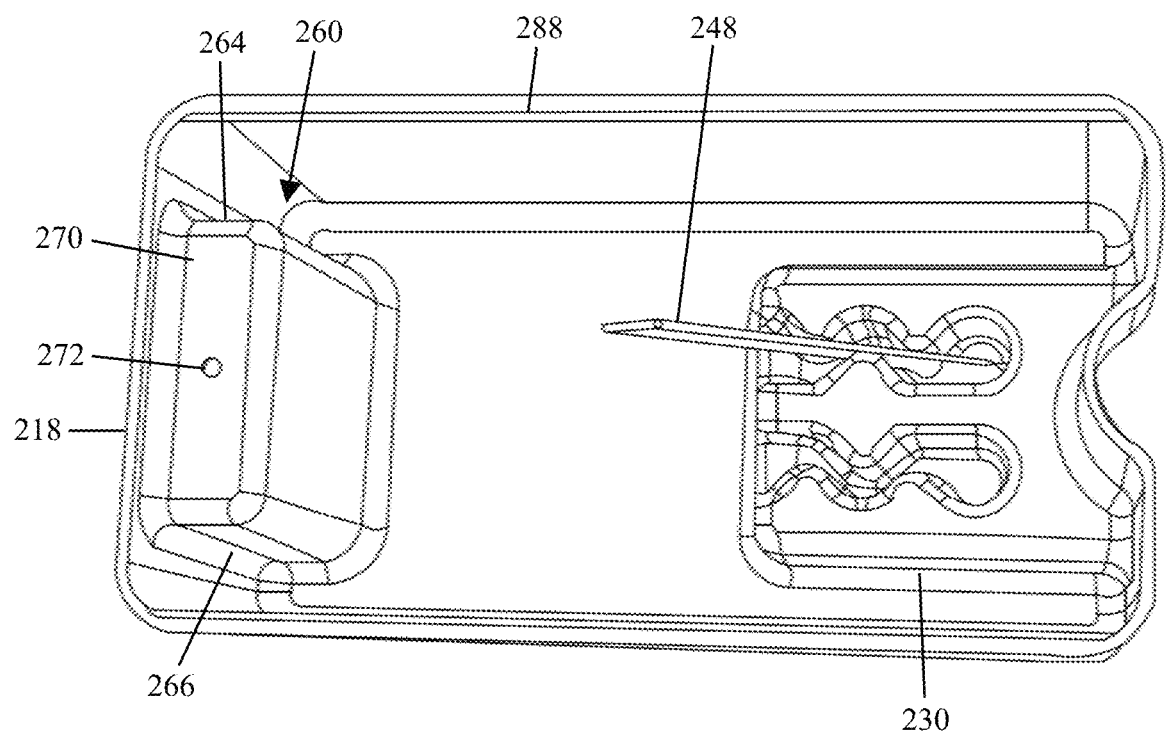
FIG. 50 is an alternative view of the interior of the safety blade container illustrated in FIG. 41 and having a surgical blade secured therein.
Figure 51:
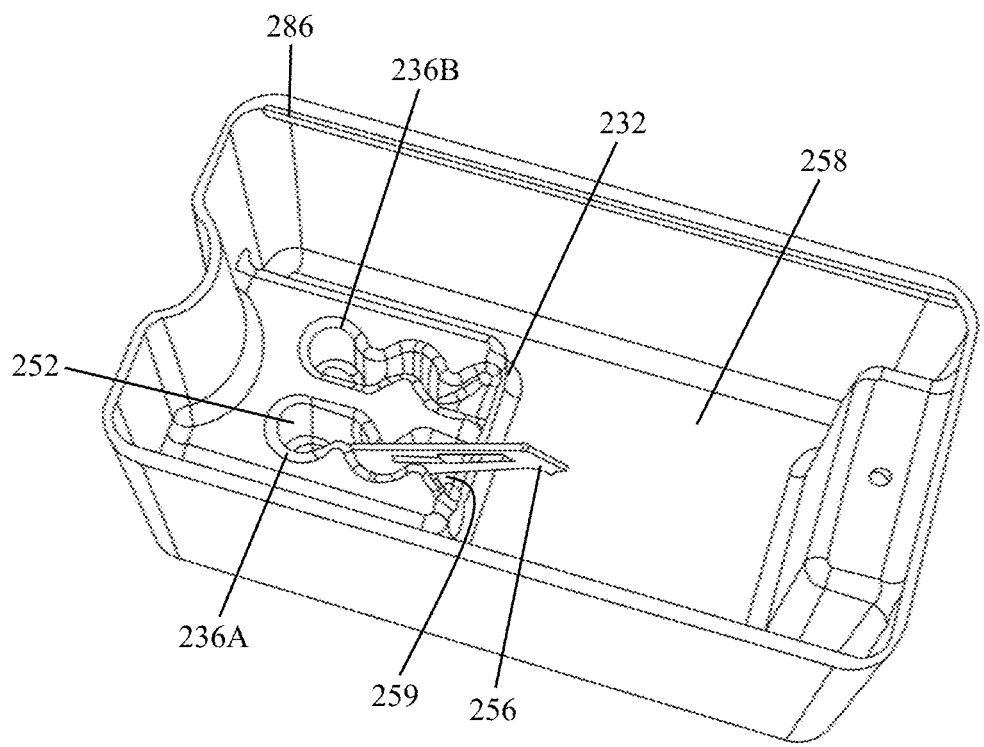
FIG. 51 is an alternative view of the interior of the safety blade container illustrated in FIG. 41 and having a surgical blade secured therein.

Referring to FIGS. 49-51, the surgical instrument receiving area 236A is shown storing/holding a surgical blade 248. A sharp or pointed edge 250 of the surgical blade 248 rests against a back wall 252 (see FIG. 51) with the cutting edge (not shown) resting against bottom surface 254. The connecting end 256 (i.e. the end that connects to a surgical cutting tool handle) of the surgical blade 248 simultaneously rests against an opposing front wall 259. The front wall 259 preferably is angled to allow the surgical blade 248 to be positioned in a particular orientation to allow a user to easily attach a surgical tool handle to the surgical blade 48 without the user having to handle the surgical blade 248 with his/her hands. This orientation, therefore, positions the surgical blade 248 so that the one end, the connecting end 256, extends up from, or is positioned above the surgical blade storage container 210 inner surface 258 or the bottom surface 254 of the surgical instrument receiving area 236A, and the other blade end, i.e., the sharp or pointed edge 250, rests at the bottom surface 254 of the surgical instrument receiving area 236A. Preferably, the surgical blade 248 is orientated at an angle from the surgical blade storage container 210 inner surface 258 and the bottom surface 254 of the surgical instrument receiving area 236A. The surgical blade storage container 210 inner surface 258 and the bottom surface 254 of the surgical instrument receiving area 236A could be the same. The surgical instrument receiving area 236B has an identical configuration as that of the surgical instrument receiving area 236A.

Positioned near wall 218 is a lid locking member 260. The lid locking member 260 comprises a main body 262 having two opposing side walls 264 and 266 separated by a front wall 268. A top wall 270 contains a locking receiving component, illustrated herein as an opening 272. The opening 272 is sized and shaped to receive at least a portion of a locking member (to be described later) associated with cover 223.

Figure 52:
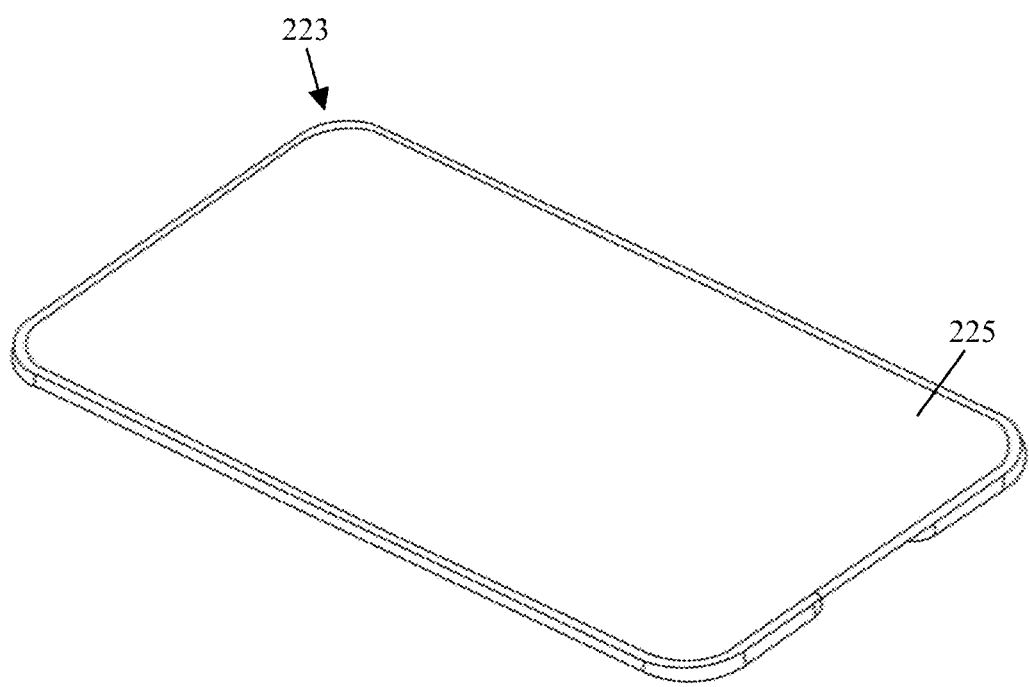
FIG. 52 is a top perspective view of an illustrative example of a safety blade container cover.
Figure 53:
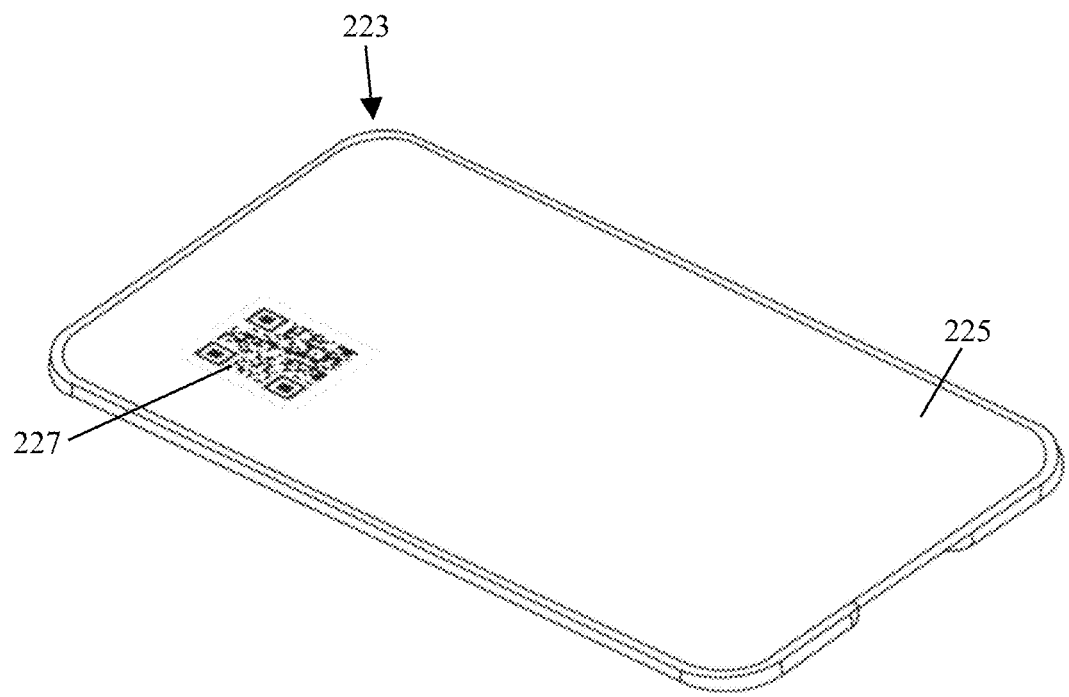
FIG. 53 is a top perspective view of an illustrative example of a safety blade container cover having a QR code.
Figure 54:
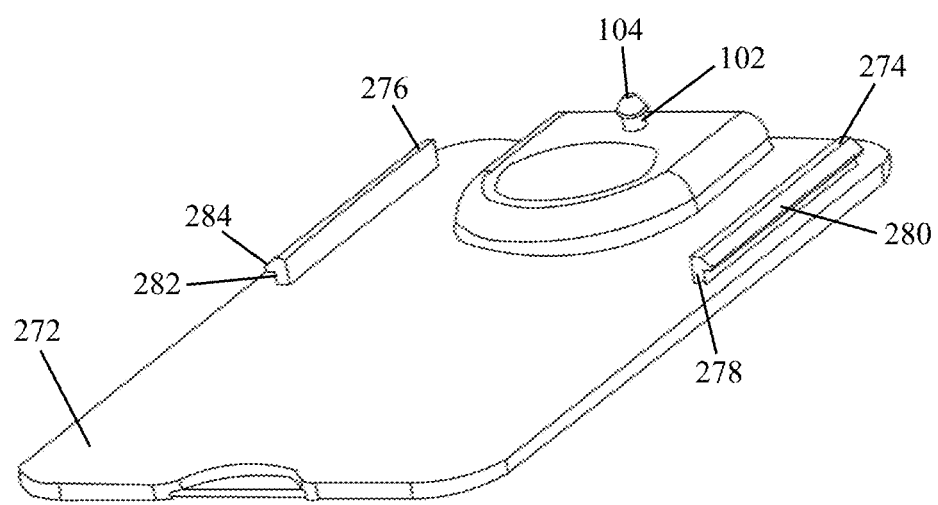
FIG. 54 is a perspective view of the interior surface of the safety blade container cover illustrated in FIG. 52.
Figure 55:
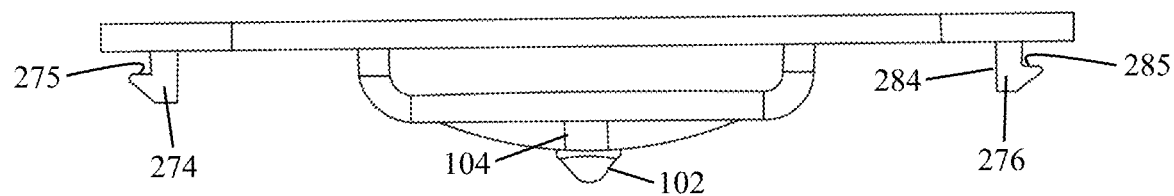
FIG. 55 is a front plan view of the safety blade container cover.
Figure 56:
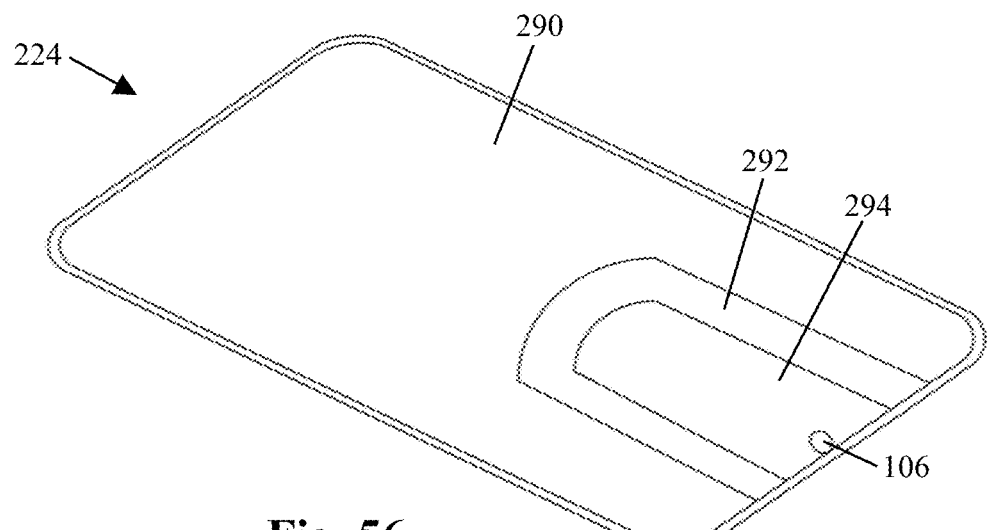
FIG. 56 is a top perspective view of the safety blade container cover illustrating the locking receptacle without a locking pin.
Figure 57:
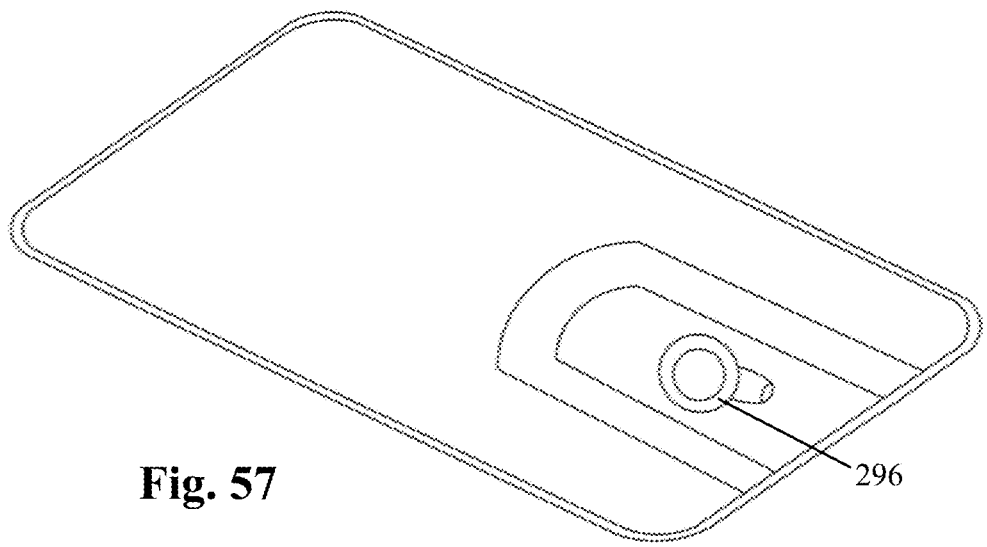
FIG. 57 is a top perspective view of the safety blade container cover illustrating the locking receptacle with a locking pin.

Referring to FIGS. 52-54, an illustrative example of the cover 223 is shown. The cover 223 is configured to slidably engage with the lower portion through engagement with the side walls 212 and 214. An inner surface 272 (see FIG. 53) contains a right guide rail 274 and a left guide rail 276. The right guide rail 274 contains a first portion 278 which extends away from the inner surface 272 and a second portion 280 that extends away from and at an angle from said first portion 278. The second portion 280 contains a first guiding surface 275. The left guide rail 276 contains a first portion 282 which extends away from the inner surface 272 and a second portion 284 that extends away from and at an angle from said first portion 282. The second portion 284 contains a second guiding surface 285. In use, the right guide rail 274 and the left guide rail 276 are positioned so that the first guiding surface 275 and the second guiding surface 285 slidably engage a first lower portion guide member 286 positioned along the length of side wall 212 and a second lower portion guide member 288 positioned along the length of side wall 214, see FIGS. 50 and 51. The second portion 280 of the right guide rail 274 and the second portion 284 of the left guide rail 276, therefore, slide against the first lower portion guide member 286 and the second lower portion guide member 288 as a user slides the cover in a first (forward) or second (reverse) linear direction.

Figure 58:
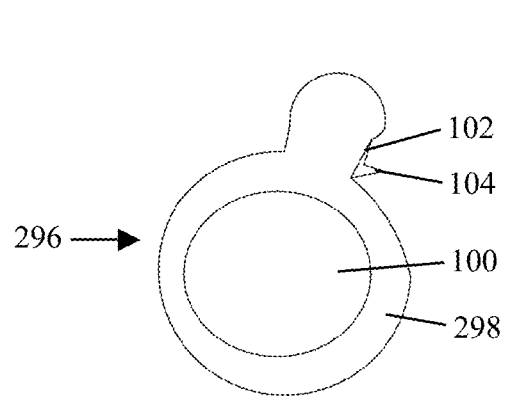
FIG. 58 is a top view of an illustrative embodiment of a locking pin.
Figure 59:
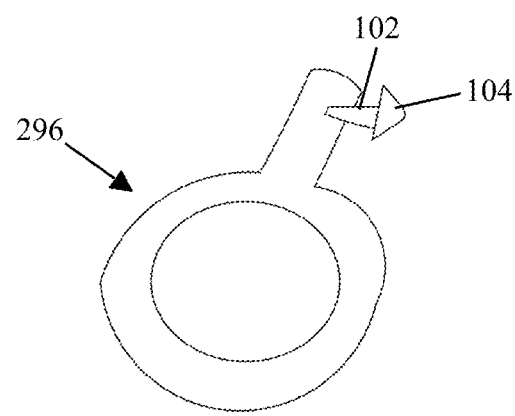
FIG. 59 is a bottom view of the locking pin shown in FIG. 58.

Integrally formed to the front surface 920 of the cover 223 is a locking receptacle 292. The locking receptacle 292 is shown as a U-shaped area having a recessed floor 294 sized and shaped to hold a locking pin 296. FIG. 58 and FIG. 59 show an illustrative embodiment of the locking pin 296. The locking pin 296 comprises a circular body 298 with an open center section 100. Extending off the circular body 298 is a locking peg 102 having a frustoconical shaped end 104. The locking peg 102 is sized and shaped to fit into opening 106 within the cover 223 and within the locking receiving component opening 272 of top wall 270. As such, when the cover 223 is placed onto the lower portion, opening 106 and opening 272 align together to allow the locking peg 102 to fit within both openings, thereby locking the cover to the side walls 212 and 214.

The surgical blade storage container 210 can be configured to provide easy and rapid visualization using a visual indicator to alert the surgical team as to which side (left or right), sometimes referred to as "laterality", of the patient a surgical procedure is to take place. All of, or some portion of the surgical blade storage container 210 may have a color coding of some shade of red, illustrated herein as pink/rose color hash markings, to indicate a right side surgical procedure. All of, or some portion of the surgical blade storage container 210 may have a color coding of some shade a purple based color, preferably a lavender color, to indicate a right side surgical procedure. Alternative visual indicators may include symbols, letters, words or phases. In any embodiment, the surgeon or surgical team member can easily ensure that the position of the surgical site or laterality aligns with the color of the container. Gray can be used to indicate neutrality, or no laterality.

Figure 60:
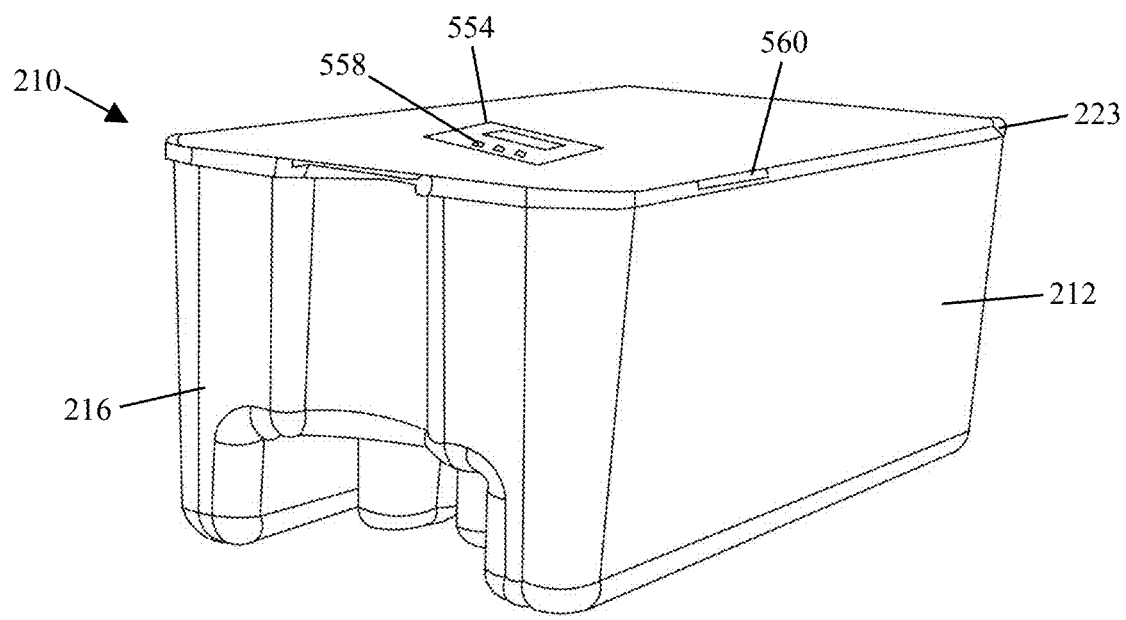
FIG. 60 is a perspective view of a container for surgical equipment according to an alternative embodiment of the invention showing the container having a central control unit.
Figure 61:
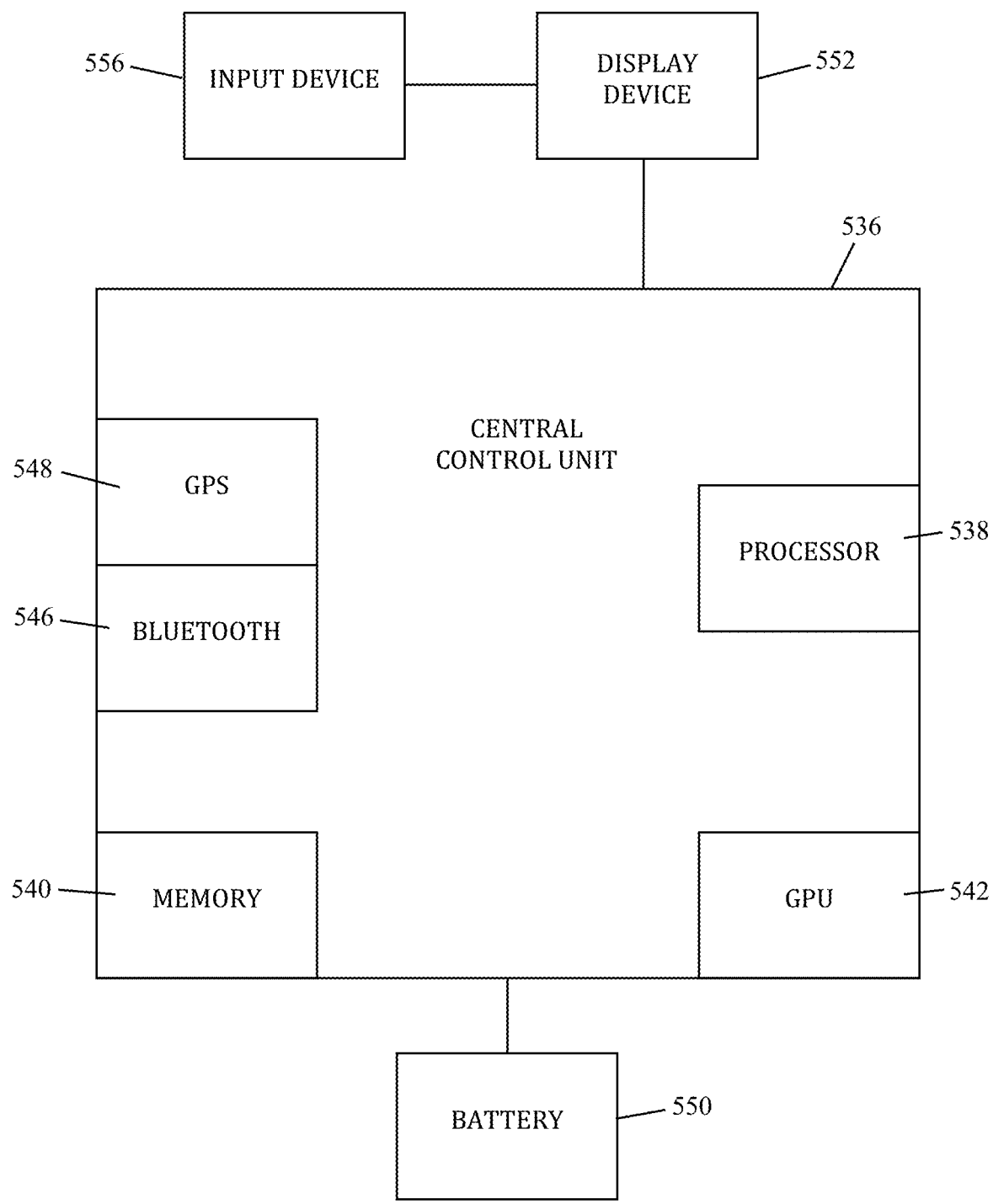
FIG. 61 is a schematic diagram of the components of an illustrative example of a central control unit shown generally in FIG. 60.

FIGS. 60 and 61 illustrate the surgical blade storage container 210 converted to a "smart" container. The cover 223 is adapted to include a central control unit 536 including, for example, a processor 538, memory 540, graphic processing unit 542, GPS functioning 544, and Bluetooth wireless capability 546. The central control unit 536 can be powered by a battery 550 and electrically connected to a display unit 552, such as an LED screen 554, see FIG. 20A. Data input devices, such as buttons 558 or a keyboard (not shown), may be included to allow the user to input data. The surgical blade storage container 210 may also contain a connection point, illustrated herein as a USB port 560 to allow for transfer of data from the central control unit 536 to a flash drive or a computer system via cables.

The surgical blade storage container 210 can be used in any surgical procedure as a standalone device. In addition, the surgical blade storage container 210 may be a component in a system or method of preventing wrong site surgeries, such as the '210 PCT described and incorporated by reference above.

The variously safety-blade dispensers disclosed herein may be provided with a unique container identification number, similar to a vehicle identification number (VIN) used for automobiles. The container identification number (CIN) may be established at the time of manufacture and remains with a particular container. This number is unique to the container in that the number is never reused and never applied to different containers. The unique identification numbers can be integrally formed into the container or may be attached to the container as part of a separate label, or part of the bar code or QR/Scan codes. Once the unique number is assigned to a container and/or is then further correlated or associated to a particular patient, the container as well as the patient information coupled to it is serialized. This allows for the container to be tracked and analyzed as it moves through the medical system. In cases in which a patient has been determined to have wrong information, i.e. the patient should have a right-side surgery, but the box is coded for a left side surgery, the container is destroyed and the reason(s) for its destruction is electronically attached to the unique number. This allows for hospitals or manufactures to review all containers manufactured or scheduled for a medical procedure to determine how many were actually used in such surgical procedures. For those containers not used, reasons as to why containers failed to be used in a medical procedure, potential errors (incorrect/inaccurate manual inputs, near misses), or wrong site surgeries/never events can be reviewed, providing insight as to when, where, and why surgical mistakes were made. Periodical reviews of such data allows hospitals to identify areas that need improvement. The system produces the first accurate and reliable near miss and WSS error data for future data mining, analysis by single and multiple attributes, root cause analysis, to assist hospital system quality control and improvement efforts.

Figure 62:
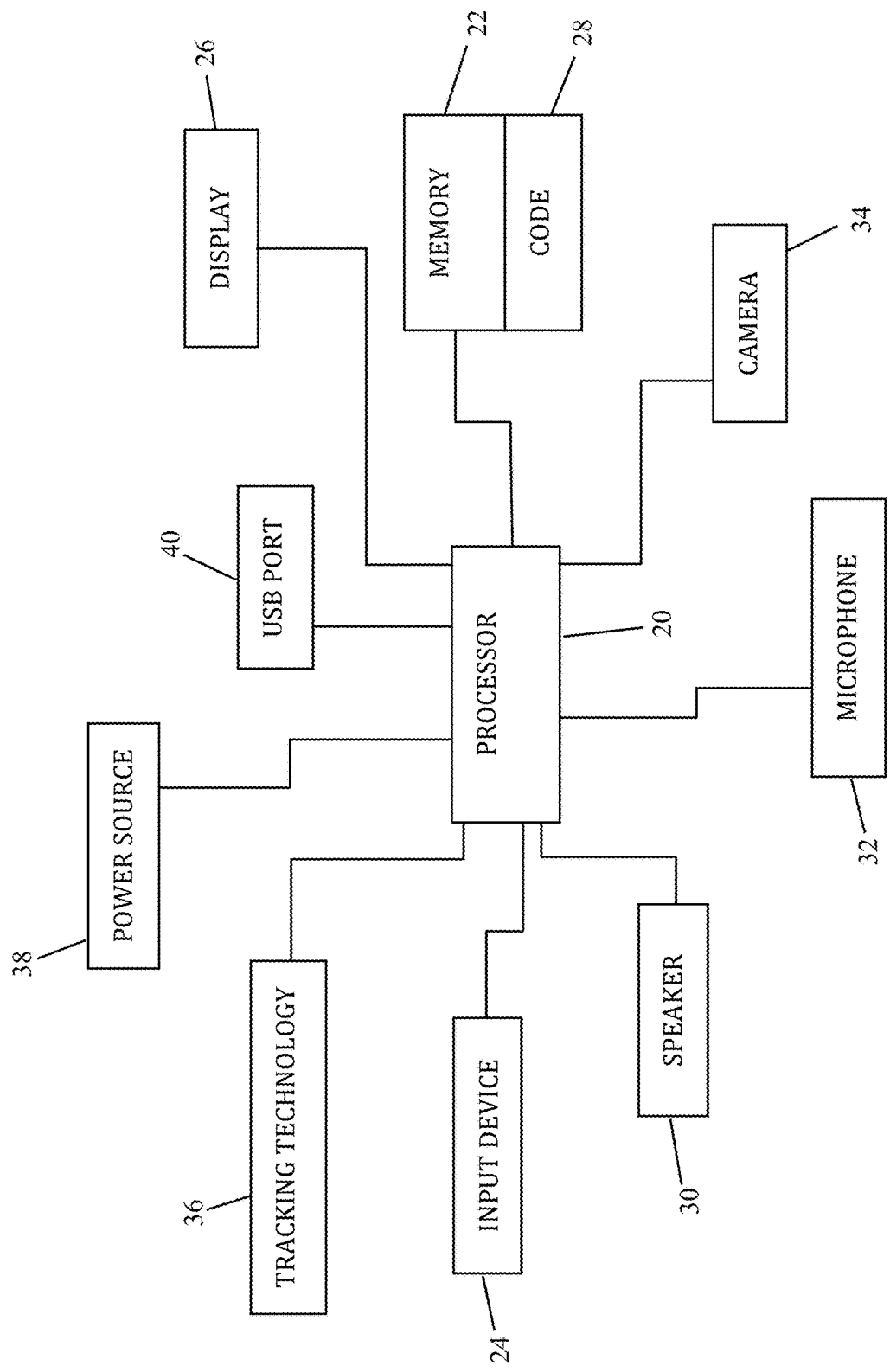
FIG. 62 is a block diagram of an illustrative computing device computing device for use in the wrong-site surgery prevention system of the present disclosure.

While computing devices are known in the art, as shown in FIG. 62 such devices generally include a central processing unit (CPU) 20 coupled to memory 22, and networking hardware. Computing devices may be operatively connected with the CPU 20 such that the CPU 20 can process network traffic inbound from the Internet and deliver outbound network traffic to the Internet utilizing, for example, a multi-layered networking protocol, such as TCP/IP. The CPU 20 is preferably connected to or may have input devices 24, such as a keyboard, mouse, or a touch screen display displaying alphanumeric and/or numeric symbols. A display unit 26, such as an LCD screen, may be used to display any data output. The memory 22 may include both volatile and non-volatile memory, and stores program code 28 executable by the CPU 20. The program code 28 causes the CPU 20 to perform various steps that direct each computer 16 and/or hand-held device 18 to perform one or more embodiment methods for preventing wrong site surgery. The program code 28 may reside in permanent memory, such as on a hard disk, and then be loaded into non-volatile memory for execution, or may (for example) be obtained from a remote server via the networking hardware and then loaded into non-volatile memory for execution. Use of a computer database (not shown) for storing user-specific data and/or a program database may also be envisioned, although persons of ordinary skill routinely make use of alternative strategies for storing data for use by a CPU 20. The computer 16 and/or hand-held device 18 may contain one or more speakers 30, microphones 32, or cameras 34. To aid in tracking capability, the hand-held device 18 may contain one or more tracking technologies 36, such as GPS (Global Positioning System) transmitters or receivers, RFID (Radio Frequency Identification) transmitters or receivers and/or other wireless tracking technology. The hand-held device 18 includes a power source 38, which may be any of a variety of suitable battery types including but not limited to a rechargeable Lithium battery. A USB port 40 may be provided on computer 16 and/or hand-held device 18 to aid in powering the device and/or for transferring data.

As described above, the safety blade-dispenser 14 includes a variety of scalpel blades for the surgeon to select from in order to perform the first incision of the operation. The safety blade-dispenser 14 (and/or label described below) is color-coded to indicate the laterality of the surgery (e.g. rose or red for "right" sided surgery, lavender for "left" sided surgery, and a neutral color (such as grey) for a surgery with no-laterality). The safety blade-dispenser 14 includes a label with a QR code capable of being scanned and linked with patient-data from the patient ID band 46 via the software assembly 12 to create a unique identifier for the particular safety-blade dispenser 14 assigned to the patient during the pre-operative assessment in the hospital after admission on the day of surgery. This unique identifier ensures that the patient receives the correct type of blade-dispenser 14, meaning the correct laterality of the intended surgery, and can be tracked throughout the remainder of the medical environment and associated with any data captured throughout the entire medical environment to ensure it is correct and used to perform the intended surgery. The label can only be removed from the safety-dispenser 14 after a timeout has been performed by the surgeon or authorized OR personnel. Once the label is removed, the surgeon then and only then has access to a variety of scalpel blades in the blade dispenser 14, the desired one of which can be safely advanced out of the dispenser 14 for engagement to a handle such that the first incision can be made and the operation commenced.

The system of preventing wrong-site surgeries and blade-related injuries 10 allows for tracking of a variety of data from pre-hospitalization to the actual surgical procedure, which the software system 12 can use to generate any of a variety of analytics 48. The analytics 48 may be based upon, but not necessarily limited to, so-called "near miss" data (that is, errors that were caught and avoided during the use of the system 10), surgery type and laterality, surgical outcomes, surgical complications, patient demographics, geographic information, as well as the date, time, location and personnel associated with each interaction or use of the system 10 for efficiency and accountability. For example, analytics 48 based on "near miss" data may provide the hospital and/or insurers and/or quality improvement specialists valuable data as to where errors or possible errors may have occurred in order to drive remediation efforts to minimize or avoid such errors in the future. The analytics 48 may also be used to identify best practices based on the data collected, either within the hospital system ("intra-system") and/or amongst multiple different hospital systems ("inter-system"), and assessed to identify best practices for further reducing wrong-site surgery errors.

The system of preventing wrong-site surgeries and blade-related injuries 10 can be designed to track location of the patient as well as the surgical supplier carrier (e.g. safety blade-dispenser 14) at any point within the medical environment. In one illustrative embodiment, an RFID tag can be embedded within the surgical supply carrier. This provides a mechanism to track the geolocation of the surgical supply carrier in the surgical environment. An RFID tag may also be tagged to the individual patient moving through the surgical environment. Associating an RFID tag to the patient allows a determination to be made as to where the patient is, and for how long he/she was at that location. If both the patient and the surgical supply carrier have an RFID tag, data can be collected and/or a notification can be sent should the patient and the surgical supply carrier be separated within the hospital or surgery center. As noted above, the system 10 may also include biometric-based identification technologies to identify the patient (and/or guardian if the patient is a minor or incapacitated) at any point throughout the medical environment.

Figure 63:
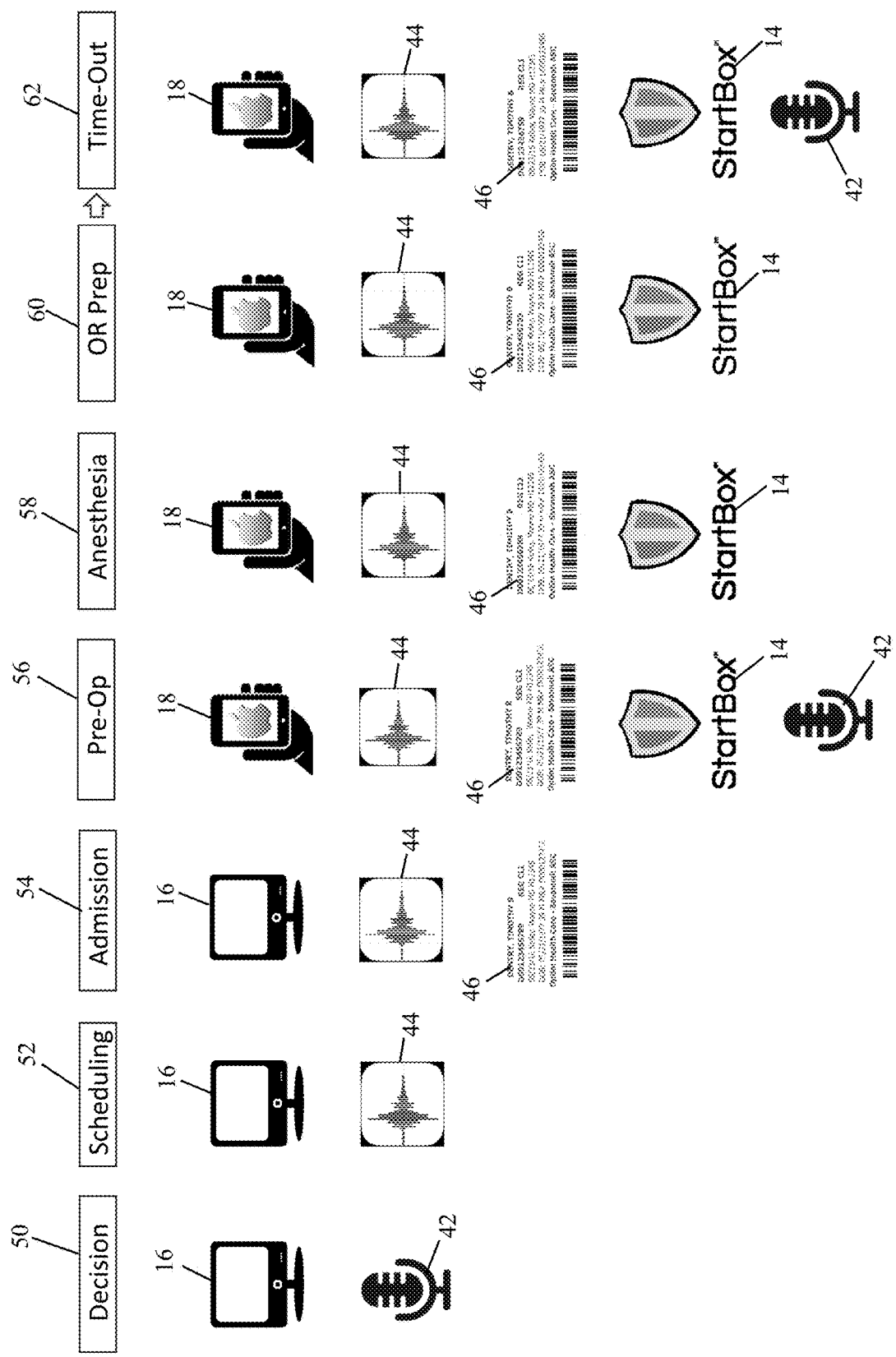
FIG. 63 is a flowchart illustrating the progression of use of the wrong-site surgery prevention system of FIG. 1 at various stages throughout the medical environment.

FIG. 63 illustrates several exemplary stages the system 10 may be used within the medical environment, including various components of system 10 which a patient may encounter during each such exemplary stage. Stage 50 involves the decision to have surgery which occurs between the surgeon and the patient and employs the use of the software system 12 (e.g. via computer 16) and voice recording 42 functionality. The decision for surgery typically occurs in the surgeon's office after one or more consults and assessments of the patient's pathology and surgical options.

The system 10 allows the surgeon to create a patient profile within the software system 12 for that particular patient, which may include any of a variety of information regarding the intended surgery. This intended-surgery information may include (but is not necessarily limited to) patient name, date of birth, procedure type, procedure location, procedure laterality, and surgeon name. Preferably, a standard coding system, such as the CPT (Current Procedural Terminology) Code Book written by the American Medical Association or other common medical coding systems (such as ICD10) should be employed so that there is no confusion as to the intended surgical procedure. The patient profile also importantly includes a voice recording 42 created by the surgeon (through the use of the software system 10) as he or she dictates aloud the intended-surgery information. The voice recording 42 may also include the patient's consent to the intended surgery. The patient profile may be input into the software system 12 via a computer 16 located in the surgeon's office and/or via a handheld device 18 running the software system 12 in application form (to be described below). The software system 12 also saves the time and date that the patient profile was created, as well as the individual in the surgeon's office who created it. The system 10 may incorporate biometrics-based identification technologies to identify the patient and/or the guardian, such as if the patient is a minor or incapacitated.

Stage 52 involves scheduling the surgery based on patient profile/electric profile and employs the use of the software system 12 (e.g. via computer 16) and the audio playback 44 functionality. To do so, the surgeon's office will contact the surgery scheduler at the hospital or surgery center to find an available date for the intended surgery based on OR availability and the schedule of the surgeon and any key support OR personnel or specialists (e.g. access surgeons, etc. . . . ). When an open date and time is selected, the surgery scheduler uses the software system 12 (e.g. via computer 16) to update the patient profile to include the date, time and location of the scheduled surgery, which may then be communicated to the surgeon's office and the patient to ensure its on their respective calendars. Importantly, the surgery scheduler may utilize the audio playback 44 of the system 10 to listen to the voice of the surgeon as he or she dictated the intended-surgery information at the decision stage 50. This recording playback 44 feature provides an advantageous cross-check on the scheduling process, in that it allows the surgery scheduler to replay the original recording to ensure: (a) the information communicated by the surgeon's office (e.g. by phone) matches that of the original voice recording 12; and/or (b) the information received from the surgeon's office (e.g. by phone) was accurately entered into the software system 12 by the surgery scheduler. The software system 12 also saves the time and date that the patient profile was updated, as well as the individual in surgery scheduling who updated it. Once the surgery has been scheduled, the software system 12 can be configured to send out a link to the patient via email, text SMS, or another electronic mechanism, which contains a written notification with details (along with date, time, location of surgery and any pre-admission restrictions, such as no-food, time to arrive at admissions, parking instructions) of the surgery or link directing the patient to an online patient portal to retrieve the content. The system 10 may also be used to track any pre-surgical clearances and/or assessments, such as (but not limited to) cardiac and/or blood work-ups that may need to be conducted and successfully passed before the day of surgery.

Stage 54 involves the admission of the patient at the location of surgery (e.g. hospital or surgery center) on the day of the scheduled surgery. This stage employs the software system 12 (e.g. via computer 16), the audio playback 44, and patient ID band 46 scanner. After showing appropriate identification (e.g. driver's license, passport, etc. . . . ) to admissions personnel and/or using patient-identification biometrics (noted above), the patient is assigned an identifying device, such as patient identification (ID) band 46 capable of being attached or coupled to the patient in some manner, most commonly around the wrist of the patient. The patient ID band 46 includes a bar code with identifying information such as patient name, date of birth, and social security number. The admissions personnel may then update the patient profile within the software system 12 to include the patient information from the patient ID band 46, such as by using a scanner in electronic communication with the software system 12. The admissions personnel may also use the software system 12 (e.g. via computer 16) to listen to the original voice recording 44 of the surgeon to double check that the intended-surgery information in the software system (as entered by the surgeon's office and updated by the surgery scheduler) is accurate and consistent with the intended-surgery information of the voice recording 44. This represents yet another cross-check on the integrity of the information in the software system 12 and ensure the scheduled surgery is as intended. The software system 12 also saves the time and date that the patient profile was updated, as well as the individual in admissions who updated it.

Stage 56 involves the patient checking in to the pre-operative stage or department (so-called "pre-op") within the location of the scheduled surgery. This stage employs the software system 12 (e.g. via hand-held device 18 running an app), the audio playback 44 functionality, the patient ID band 46 scanning functionality, the safety blade-dispenser 14 label scanning functionality, and the audio recording 42 feature. When the patient arrives at pre-op, pre-op personnel will use the software system 12 (e.g. via hand-held device 18) to distribute and assign an appropriate safety blade-dispenser 14 to the patient. To do so, pre-op personnel will use a scanner to scan the patient ID band 46, which will then bring up the patient profile for that particular patient. With the patient profile revealed, pre-op personnel may then select and distribute an appropriate safety blade-dispenser 14 depending upon the laterality of the intended surgery (e.g. rose-colored for a right-sided surgery, lavender-colored for a left-sided surgery, or neutral-colored (such as grey) for a procedure without laterality). Pre-op personnel will then use the scanner to scan a unique identifier on a label disposed on the safety blade-dispenser 14, which may take the form of a unique serial number stored in a data-storage feature on the label, such as (but not necessarily limited to) a barcode or QR code. The software system 12 may then be used by pre-op personnel to link the data from the patient ID band 46 to the data on the label of the safety blade-dispenser 14. In this fashion, the specific safety blade-dispenser 14 is assigned to the specific patient, which facilitates accurate tracking of the safety blade-dispenser 14 the rest of the way through the medical environment. The surgeon may use the voice recording 42 functionality to amend the patient profile to include a second voice recording associated with any add-on surgery he or she decides to do during the pre-op assessment. The voice recording 42 may also include the patient consent to the add-on surgery.

Pre-op personnel may also use the system 10 to listen to the original voice recording 44 of the surgeon to double check that the intended-surgery information saved in or by the software system 12 (as entered by the surgeon's office and updated by the surgery scheduler, admissions personnel and optionally any pre-surgery work-up assessment/clearance) is accurate and consistent with the intended-surgery information of the voice recording 42. This represents yet another cross-check on the integrity of the information saved in or by the software system 12 and ensure the scheduled surgery is as intended. If a problem is detected, pre-op personnel may select "No Go" functionality within the software system 12. The surgeon may review and override if he or she decides the problem has been resolved or, alternatively, cancel the surgery if he or she decides the problem has not been resolved or surgery should not go forward as scheduled. The software system 12 also saves the time and date that the patient profile was updated, as well as the individual in pre-op who updated it.

Stage 58 involves anesthesia personnel using the system and methods of preventing wrong-site surgeries and blade-related injuries 10 to confirm they are to administer anesthesia to the correct patient for the correct or intended surgery. This is an optional step and merely illustrates how the system and methods of preventing wrong-site surgeries and blade-related injuries 10 may be used by any of a variety of hospital or OR-personnel throughout the medical environment. This stage employs the use of the software system 12 (e.g. via hand-held device 18 running an app), the audio-playback 44 functionality, the patient ID band 46 scanning functionality, and the safety blade-dispenser 14 label scanning functionality. Anesthesia personnel may use the system 10 to listen to the original voice recording 42, scan the patient ID band 46 and/or scan the label of the assigned safety blade-dispenser 14 to ensure the patient and the intended-surgery are consistent with the original voice recording 44 of the surgeon, a voice recording 44 for any add-on surgery decided upon and consented during pre-op and/or with the anesthesia plan. If a problem is detected, the anesthesia personnel may select "No Go" functionality within the software system 12. The surgeon may review and override if he or she decides the problem has been resolved or, alternatively, cancel the surgery if he or she decides the problem has not been resolved or surgery (original and/or add-on) should not go forward as scheduled. The software system 12 also saves the time and date that the patient profile was updated, as well as the individual in anesthesia who updated it.

Stage 60 involves OR preparation (so-called "OR prep") wherein the patient is transferred from pre-op to the OR and prepared for surgery. This stage employs the use of the software system 12 (e.g. via hand-held device 18 running an app) and the audio-playback 44 functionality, the patient ID band 46 scanning functionality, and safety blade-dispenser 14 label scanning functionality. The patient is delivered from pre-op to the OR, which is accomplished by placing the patient on a stretcher or rolling bed and coordinating a hand-off between pre-op personnel and OR personnel. The hand-off may be accomplished by having pre-op personnel move the patient out of pre-op towards or to the OR so OR personnel can accept responsibility or, alternatively having OR personnel go to pre-op and pick up the patient. In either event, during this hand-off exchange OR personnel will use the software system 12 (e.g. via hand-held device 18) to scan the patient ID band 46 and/or the label of the safety blade-dispenser 14 that was assigned to the patient in pre-op. OR personnel will then inspect the data resulting from this scanning and compare it to, among other things, the laterality color-coding of the safety blade-dispenser 14 to ensure the correct patient has the correct and assigned safety blade-dispenser 14.

OR personnel may also use the software system 12 to listen to the original voice recording 44 of the surgeon to double check that the intended-surgery information in the software system 12 (as entered by the surgeon's office and updated by the surgery scheduler, any optional pre-surgical work-up/clearance, admissions personnel, pre-op personnel, and the surgeon during pre-op) is accurate and consistent with the intended-surgery information of the original voice recording 44 (from the surgeon's office) and any second voice recording 44 (from pre-op). This represents yet another cross-check on the integrity of the information in the software system 12 and ensure the scheduled surgery is as intended. If a problem is detected, OR personnel may select "No Go" functionality within the software system 12. The surgeon may review and override if he or she decides the problem has been resolved or, alternatively, cancel the surgery if he or she decides the problem has not been resolved or surgery (original and/or add-on) should not go forward as scheduled. If the surgery is to go forward, the patient is then transferred to an OR table where they are prepared and draped for surgery. The software system 12 saves the time and date that the patient profile was updated, as well as the OR personnel who updated it.

Stage 62 involves the time-out procedure that must be performed before the surgeon can access a blade from the safety blade-dispenser 14. This stage employs the software system 12 (e.g. via hand-held device 18 running an app), the audio playback 44 functionality, the patient ID band 46 scanning functionality, the safety blade-dispenser 14 label scanning functionality, and the audio recording 42 feature. The surgeon first scans the label of the safety blade-dispenser 14 to pull up the patient profile for the patient on the OR table. The surgeon may review that data, and augment or double check that against the laterality color-coding of the assigned safety blade-dispenser 14 and the audio-replay 44 of the original voice recording from the surgeon's office and any additional recording from pre-op.

If everything is correct and the surgeon decides to move forward with the surgery, he or she next performs the time-out by: (a) gaining the attention of everyone in the OR; and (b) stating the required time-out information such as (but not necessarily limited to) patient name, date of birth, procedure, laterality (if any), and surgeon name. The surgeon preferably uses the audio recording feature 42 of the software system 12 to record as he or she speaks while performing the time-out, which becomes part of the patient profile. Once the time-out has been completed (and optionally recorded), the surgeon may then use the software to indicate that the time-out has been performed (e.g. by toggling a switch and/or clicking a designated box within the software system 12 or related app).

At that point, the surgeon will remove the label from the safety blade-dispenser 14 and place the label in or with the patient chart. By removing the label, a plurality of blades will now be accessible that were previously covered by the label. A blade count is made to document the number of blades held in the safety blade-dispenser 14, which blade information may be saved in the patient profile via the software system 12 and/or in the patient chart. With the label removed the surgeon will be able to dispense one of a plurality of blades from the housing of the safety blade-dispenser 14, which the surgeon can couple to a handle to thereafter make the initial incision. The software system 12 saves the time and date that the patient profile was updated, as well as the OR personnel or surgeon who updated it.

Figure 64A:
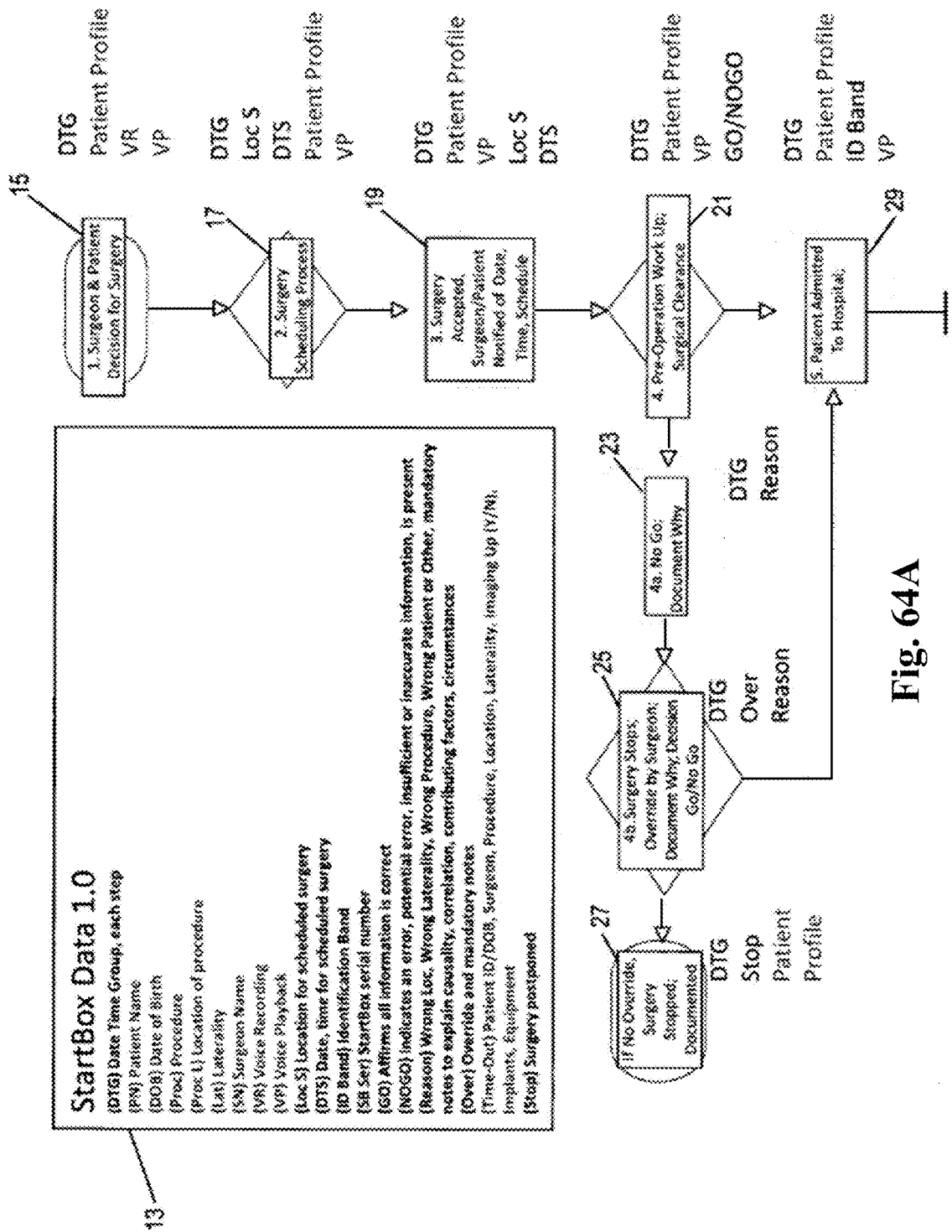
FIGS. 64A-64C illustrate flowcharts providing additional detail of the progression of use of the wrong-site surgery prevention system of FIG. 1 throughout the medical environment in accordance with the present disclosure.
Figure 64B:
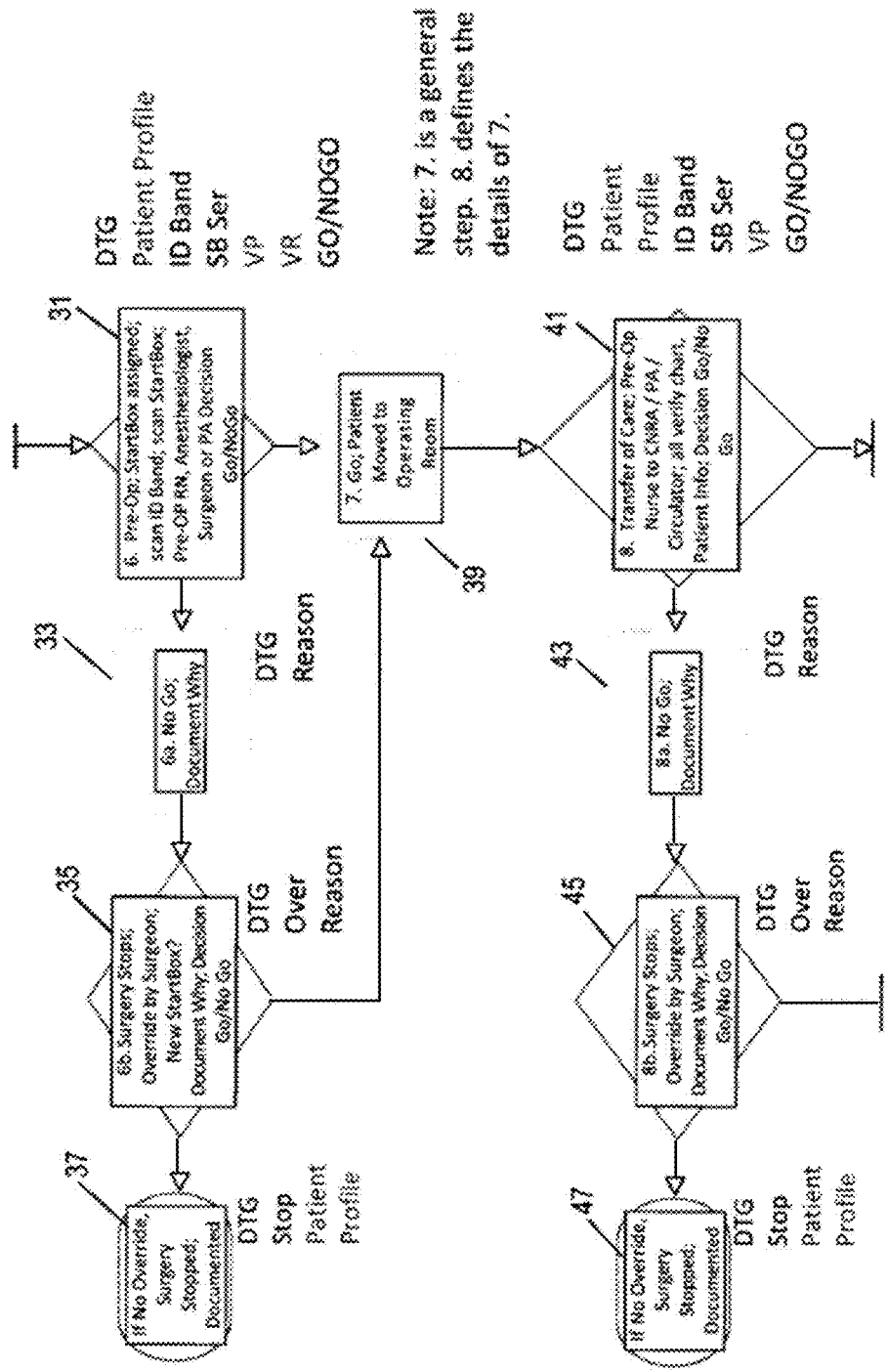
Figure 64C:
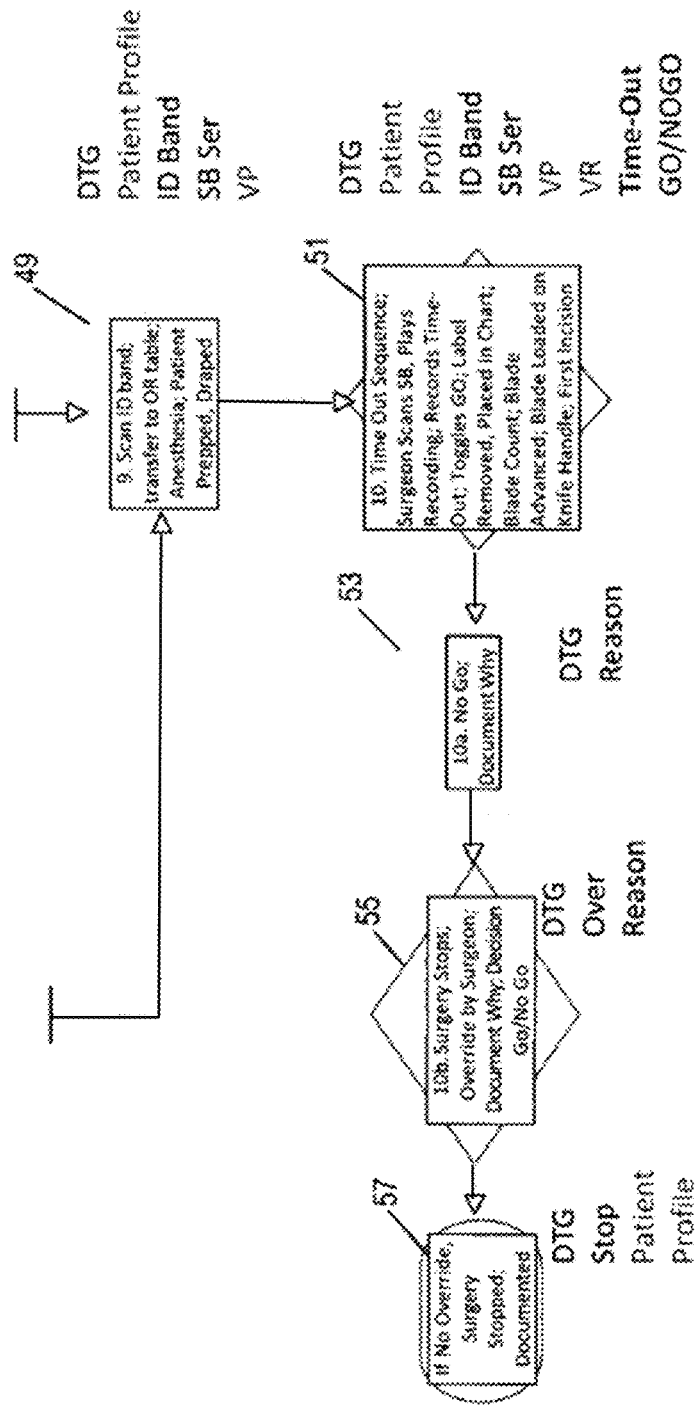

FIGS. 64A-64C are flow charts illustrating exemplary method steps of the use of the system 10, including various steps a patient might experience during his/her interaction within the medical environment with additional details beyond those described above with reference to FIG. 63. As the patient moves through the medical environment, various types of data can be used and/or obtained. Box 13 sets forth illustrative data, which may include (but is not necessarily limited to): date, time, group (DTG) of each use of the system 10 within the medical environment (where "group" means person using the system 10 for that particular use); patient name (PN); patient date of birth (DOB); intended procedure (Proc); location of the procedure (Proc L), such as the specific body part or organ; laterality (Lat) of the intended procedure; surgeon name (SN); voice recording (VR); voice playback (VP); location of the surgery (Loc S), such as specific hospital, surgery center and/or specific OR within a specific hospital or surgery center; date and time for scheduled surgery (DTS); patient ID Band (ID Band); serial number of StartBox assigned to patient (SB Ser); confirmation that all information is correct (GO); indication of error, potential error, insufficient or inaccurate information (NOGO); reason for NOGO, such as wrong location, wrong laterality, wrong procedure, wrong patient, notes to explain causality or contributing factors, existing circumstances (REASON); override and mandatory notes (OVER), where the surgeon can review and override a NOGO created by any other user at any point in the medical environment to decide whether the intended surgery can go forward or be cancelled; time-out information (Time-Out), such as patient ID (ID Band), date of birth (DOB), imaging up (Y/N) and/or reviewed if required, procedure (Proc), laterality (Lat), and whether implants and/or equipment present (Y/N); and surgery postponed or cancelled (Stop). All such data, in any combination, may be part of the patient's electronic profile.

The process begins with a first step 15 of the patient and physician together deciding to pursue a surgical treatment option. Examples of the types of actions that may occur during this step include: (a) discussing the diagnosis, patient condition, treatment options and potential recovery; (b) determining if surgery is appropriate for the patient diagnosis, condition, symptoms, and potential improvement; (c) evaluation of the desired outcomes (i.e. pros vs. cons); (d) discussing possible outcomes—identifying risks and probabilities of outcomes; and (e) patient and surgeon making a decision. There must be concurrence. Once the decision to undergo surgery has been made, the patient is associated with an electronic profile. The surgeon may provide an audio recording 44 identifying the patient and the agreed upon/intended surgery. The surgeon may further obtain an audio recording 44 of the patient's informed consent to the surgery.

The next step 17 is the Surgery Scheduling Process, during which actions may include: Surgery order is forwarded to the surgical coordinator; Surgical coordinator calls insurance for authorization (if required); Coordination of pre-op lab tests, physical exam if necessary with a physician and coordination of anesthesiology coverage; Assign a location, date, and time for the surgery. At the location where the surgery is to take place (hospital or surgery center), the patient information is checked and a Go/NoGo can be indicated via the system 10. If a NoGo is determined, the reasons why and the correction(s) are documented. An override to the NoGo can be performed. If no override is performed at this stage, the movement toward the surgery procedure is stopped and documented. Alternatively, the surgeon may wait to assess any NoGo indications later in the process, such as at pre-op. At the step of Surgery Accepted (step 19), the surgeon and patient are notified of the date, time and location of the scheduled surgery. This may be accomplished via traditional means (phone calls) or preferably having the system 10 generate automatic messages (e.g. email, texts, SMS, etc. . . . ) to the patient and/or surgeon. This may also involve communicating pre-op instructions (e.g. fasting 24 hours before surgery, etc. . . . ). The parties involved in this step may utilize the voice playback to confirm the correct patient and correct surgery.

Should the patient be required to undergo pre-surgical assessments and/or clearances (e.g. pre-surgical lab work-up, such as cardiac or blood-work), such action or patient movement within the medical environment can be tracked as well (step 21). At the Pre-Operation Work up; Clearance various actions may occur such as: If vitals, labs, or the patient present conditions which do not support or allow the procedure, the surgeon (or physician assistant, PA) stops the procedure, step 23. The surgeon (or PA) notes why the surgery is cancelled or postponed, and provides this information to the patient (or parent/guardian) and electronic profile; Surgery Stops—Override by Surgeon (reasons why), see step 25, No Go (reasons why); Documented in surgery profile, medical records; The reason for the stop is specifically noted with drop down options Wrong Site, Wrong Side, Wrong Procedure, Wrong Patient, and Other with a required notes section to assess why this occurred. This is near miss data and information; Patient (or Parent/Guardian) is informed after a stop decision. At this point in the patient movement within the medical environment, an indication of Go/NOGO can be entered and associated with the patient's electronic profile. An override to the NoGo can be performed. If no override from the surgeon is performed, the movement toward the surgery procedure can be stopped and documented, step 27. If information relating to the surgery is in order, the patient is admitted to the hospital and associated (electronic profile) with a surgical supply carrier or surgical box, such as safety blade device 14, or any other container with any one or a combination of features described herein, see steps 29 and 31. During these steps, the following may occur: Patient Admitted to Hospital; surgical box and profile Assigned; Remains with Patient: Admission procedure consists of patient's personal data being recorded (name, address, DOB, insurance, emergency contact, allergy info if any, etc.). The patient (or parent/guardian) completes any and all forms regarding detailed medical history, forms for any advance directives (medical decisions), and consent forms; A plastic bracelet is placed on the patient's wrist with the patient name, age, date of birth, room number, and medical record number on it, plus the surgical profile information (name, procedure, location, laterality, DOB); If the patient has one or more allergies, a second bracelet is placed on the patient's wrist to identify the specific allergy or allergies; The correct color, with its unique serial number, is selected and issued to the patient. This box/profile remains with the patient, at the hospital/clinic, and will remain with the patient until surgery starts. The patient receives the surgical box near the completion of the admission process; Surgery Stops—Override by Surgeon (reasons why), No Go (reasons why); Documented in surgery profile, medical records; The reason for the stop is specifically noted with drop down options Wrong Site, Wrong Side, Wrong Procedure, Wrong Patient, and Other with a required notes section to assess why this occurred. This is near miss data and information; Patient (or Parent/Guardian) is informed after a stop decision.

As the patient moves through the actual surgery component of the medical environment, the electronic patient profile can be updated accordingly. For example, the patient can be transferred to anesthesiology, where the patient profile can be checked and verified. During any point, the patient can be indicated as a Go/NoGo, see step 33, 35, 37, and 39. Actions may include may include checks by the Pre-OP RN, Anesthesiologist, Surgeon Decision at Pre-Op; and include actions such as another verification that the patient, surgery site, laterality, procedure are all correct before a patient is moved towards an operating room; Surgery Stops—Override by Surgeon (reasons why), No Go (reasons why); Documented in surgery profile, medical records. The reason for the stop may be specifically noted with drop down options Wrong Site, Wrong Side, Wrong Procedure, Wrong Patient, and Other with a required notes section to assess why this occurred. This is near miss data and information; Patient (or Parent/Guardian) is informed after a stop decision. If a NoGo is indicated, reasons for such action are documented. A new surgical carrier having a new unique identification number may be assigned to the patient and documented if required. In either case, the physician can override the action or confirm it. If there is no override by the surgeon, the surgery is stopped and documented. If the patient is deemed as a Go indication, the patient is further transferred to the next steps in the surgical procedure, see 41. Step 41 may include the following, Go; Patient moved to Operating Room: Circulating Nurse (CN) or the OR Nurse confirms/verifies identity and consent; CN/OR Nurse confirms patient information, incision site, procedure, and operating room; Patient to verify surgical site, any allergies. Actions taken can include a NoGo decision, step 43, override by surgeon, step 43, surgery stopped because of a NoGo, see step 45, or a Go. If a Go, the ID band 46 of the patient may be scanned, patient transferred to the OR table, prepped and draped, see step 49. Prior to the actual surgical procedure occurring, a timeout to verify correct information will be performed by the surgeon, see step 51. If any information is incorrect during the final timeout, a NOGo is issued and documented, see step 53. The surgeon may override the NoGo, documenting why see step 55. If the there is no override, the surgery is stopped, and the reasons why are documented see step 57. This is near miss data and information; Patient (or Parent/Guardian) is informed after a stop decision. If the surgery is a Go, the surgeon can remove the label off the surgical carrier and begin the surgery.

Figure 65:
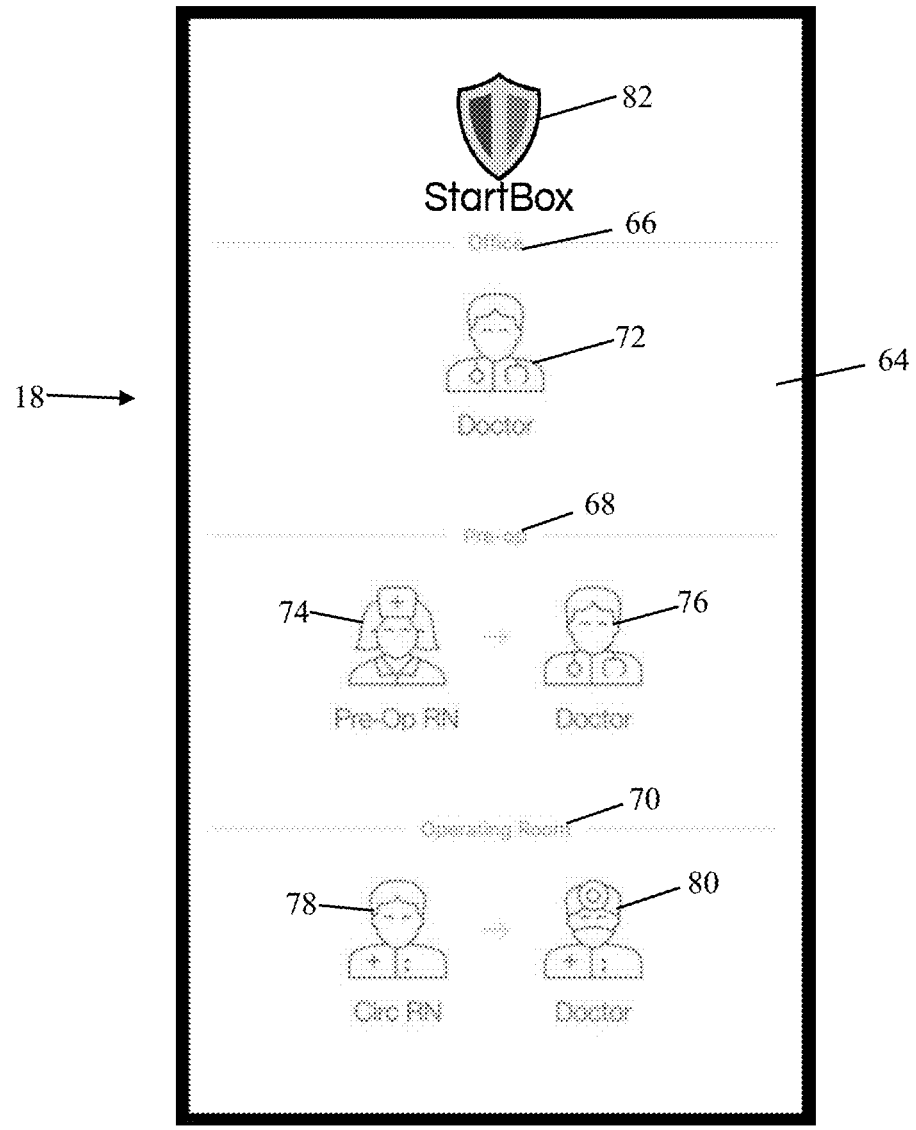
FIGS. 65-94 are representative graphical user interfaces of the software application of FIG. 1 illustrating the use of the wrong-site surgery prevention system according to an aspect of the present disclosure.

FIGS. 65-94 are illustrative examples of the software system 12 in the form of an application (or "app") running on the hand-held devices 18 of the system 10. FIG. 65 is a user-persona graphic user interface (GUI) screen 64 that identifies the potential personas that are likely to be involved with the use of the system and methods of preventing wrong-site surgeries and blade-related injuries 10 (via the application) throughout the medical environment, as based on the various roles and responsibilities of each persona. By way of example only, the user-persona graphic user interface (GUI) screen screen 64 may include an office section 66, a pre-op section 68, and an operating room (OR) section 70. The personas may include (but are not necessarily limited to) Doctor 72 in the office section 66, Pre-Op Registered Nurse (RN) 74 and Doctor 76 in the Pre-Op section 68, and Circulating RN 78 and Doctor 80 in the OR section 70. As will be seen below, the user-persona GUI screen 64 provides an easy way to visualize and track the progress of the patient through the medical environment by adding a notation after the completion of each stage in the process, such as adding the StartBox™ shield logo 82 underneath or adjacent to each persona after that stage has been completed by that persona.

Figure 66:
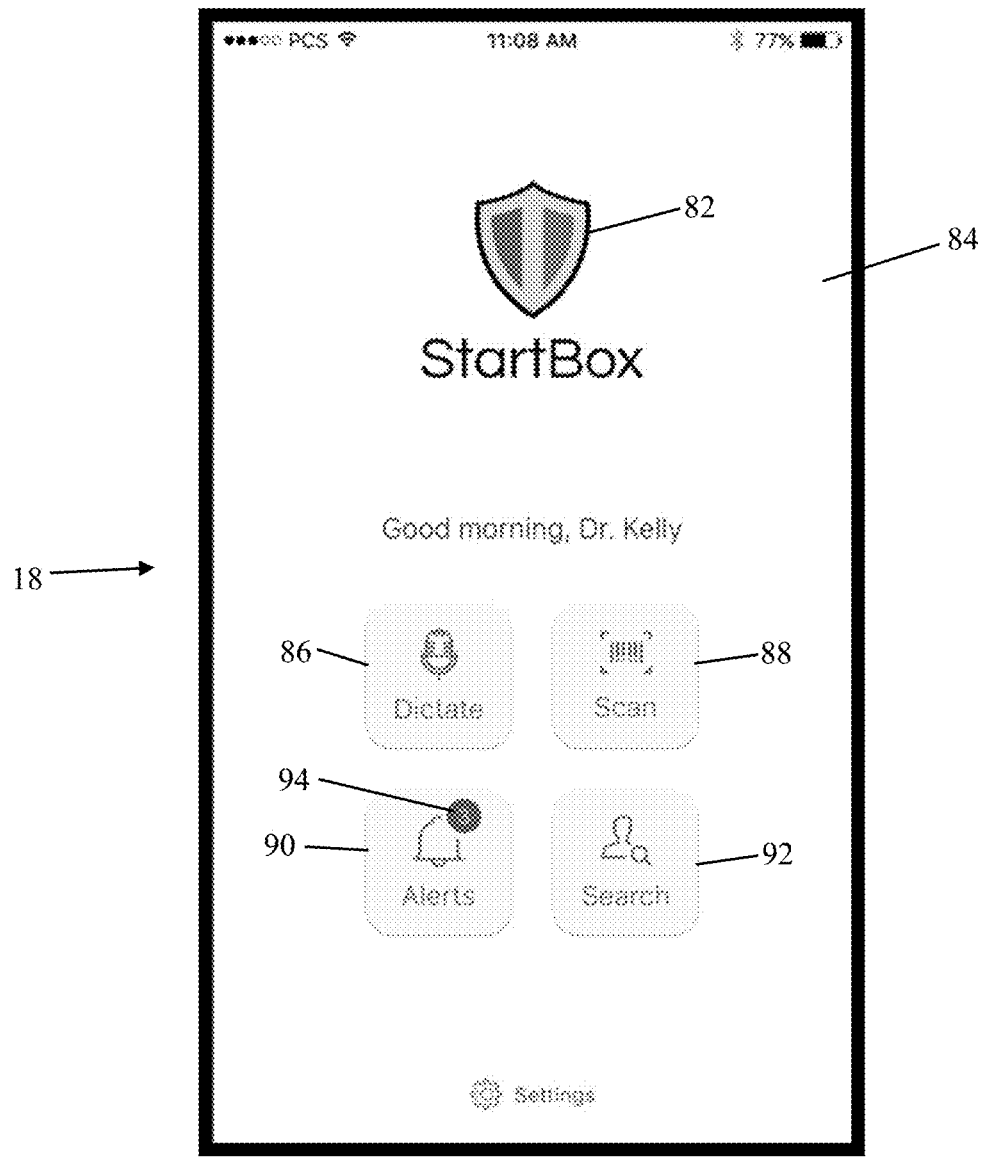

FIG. 66 is an example of an office section doctor home GUI screen 84, which is the next graphic user interface (GUI) screen in the progression of the app. While in the office section doctor home GUI screen 84, the surgeon (in this case, the fictitious Dr. Kelly) can use the app while in his office to perform one of several functions. These functions may include, but are not necessarily limited to, Dictate 86, Scan 88, Alerts 90, and Search 92. The Dictate 86 function allows the surgeon to record audio, such as the intended-surgery information (e.g. patient name, date of birth, procedure type, procedure location, procedure laterality, and surgeon name) that forms part of the patient profile created by the surgeon and/or his office staff. In addition to the intended-surgery information, the recording may also capture the consent provided by the patient during that dialogue with the surgeon. The Scan 88 function allows the surgeon to scan the patient's ID band 46 for the purposes of identifying the patient and their associated patient information. The Alerts 90 function allows the surgeon to access any of a variety of notices or alerts, such as pending prescription approvals, assessments of "no-go" selections by other medical personnel using the system 10 to determine if the surgeon wishes to override these selections and allow the surgery to proceed or cancel the particular surgery. A new item indicator 94 may appear adjacent the Alerts 90 icon to inform the surgeon of the number of new alerts, if any, that have occurred since the last time the surgeon accessed the Alerts 90 function. The Search 92 function allows the surgeon to search for any of a variety of records within the system 10, for example patient records, procedure codes, scheduled events, etc.

Figure 67:
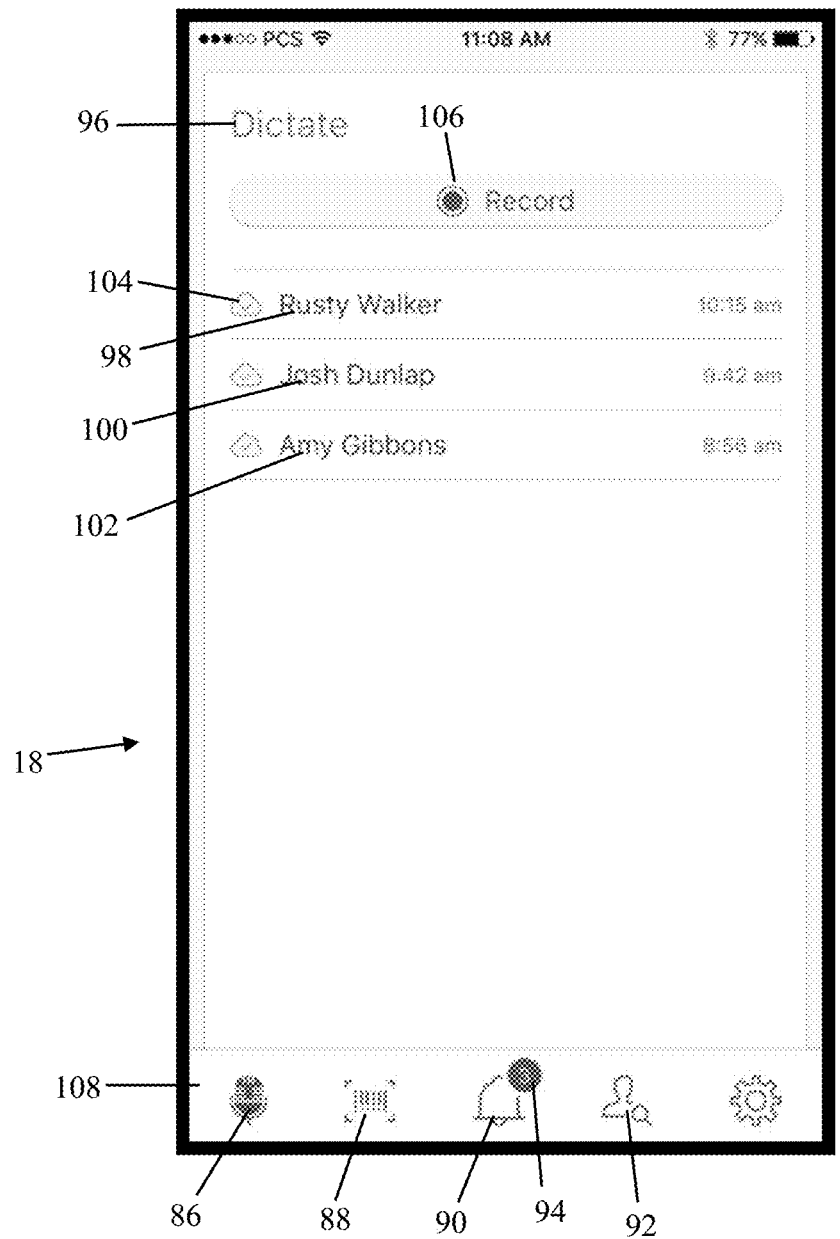

FIG. 67 shows the Dictate GUI screen 96 that appears when the surgeon selects the Dictate 86 function icon on the office section doctor home GUI 84. In an illustrative embodiment, the application will show the previous audio recordings 98, 100, and 102 made by the surgeon for prior patients over a particular time-frame (e.g. that day, that week, that month), in this example Rusty Walker (98), Josh Dunlap (100) and Amy Gibbons (102). Each prior audio recording may include a status notation 104 (e.g. a checkmark) to indicate that the prior audio recordings have been saved into a desired data storage location (e.g. a secure cloud-based data center for perpetuity). The "Record" 106 function is available to the surgeon (and surgeon only based on rules and privileges) so that only the surgeon can record new dictations. The Dictate GUI 96 further includes a menu bar 108 positioned at the bottom of the screen that includes several icons to link users to other functions, including Dictate 86, Scan 88, Alerts 90, and Search 92.

Figure 68:
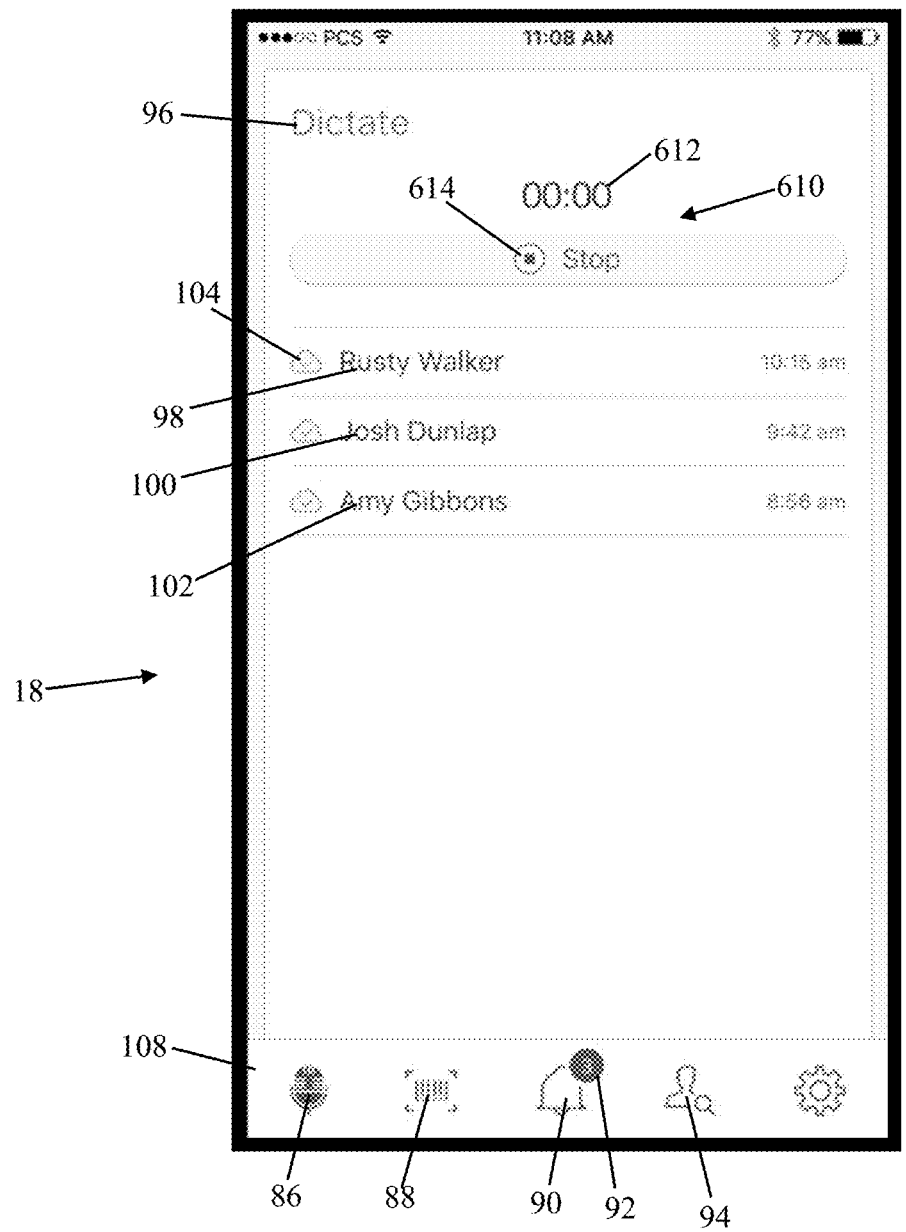
Figure 69:
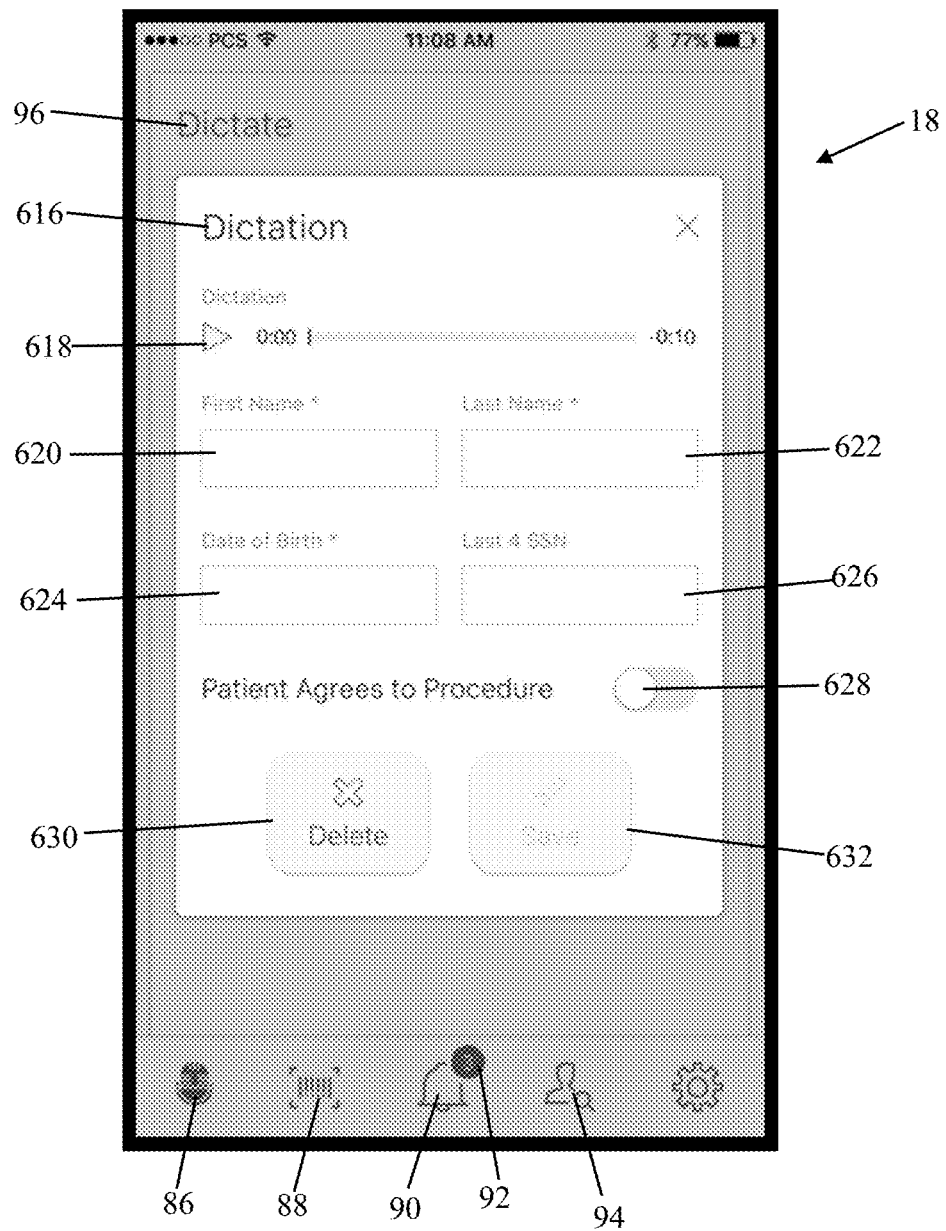

When the surgeon touches the Record 106 function, the recording modal 610 shown in FIG. 68 is presented to the surgeon-user as recording starts. The recording modal 610 includes a running timer 612 that indicates how long the dictation lasts and a stop function 614 that stops the recording when pressed. Referring to FIG. 69, when the surgeon stops the recording (by depressing the stop button 614 of FIG. 68) after the intended-surgery information is dictated by the surgeon and the patient (or guardian, as the case may be) provides verbal consent, a first pop-up window 616 is presented to the surgeon. The first pop-up window 616 includes a play icon 618 to replay the audio recording to the surgeon, data entry sections to create or update a patient profile for the particular patient (e.g. First name 620, Last Name 622, Date of Birth 624, Last 4 SSN, 626), a toggle 628 to denote that the patient consents to the procedure, and Delete 630 and Save 632 icons to perform those respective functions for that patient profile or dictation. The information may be automatically pulled from the electronic medical record (EMR) system or inputted manually into the various data entry sections.

Figure 70:
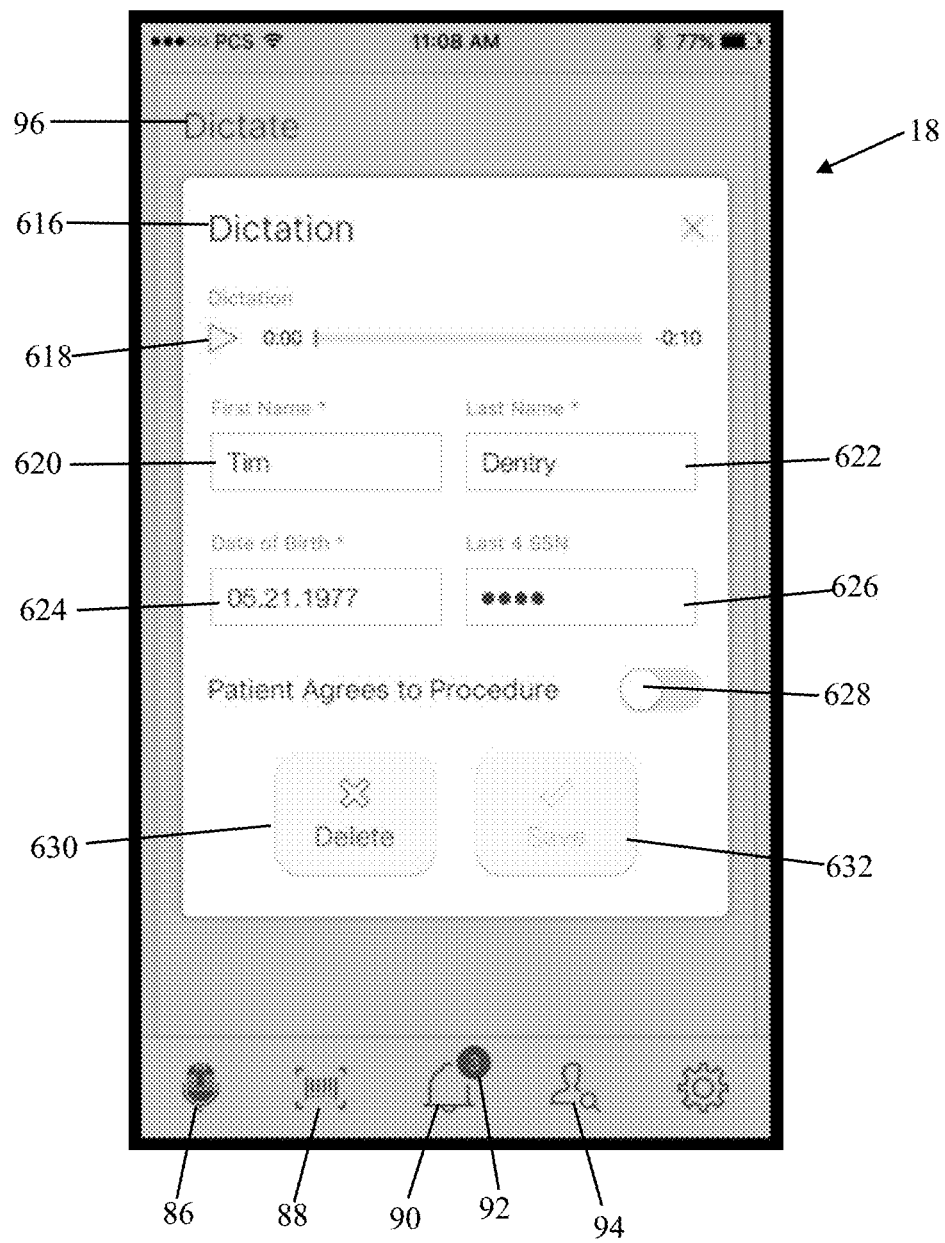
Figure 71:
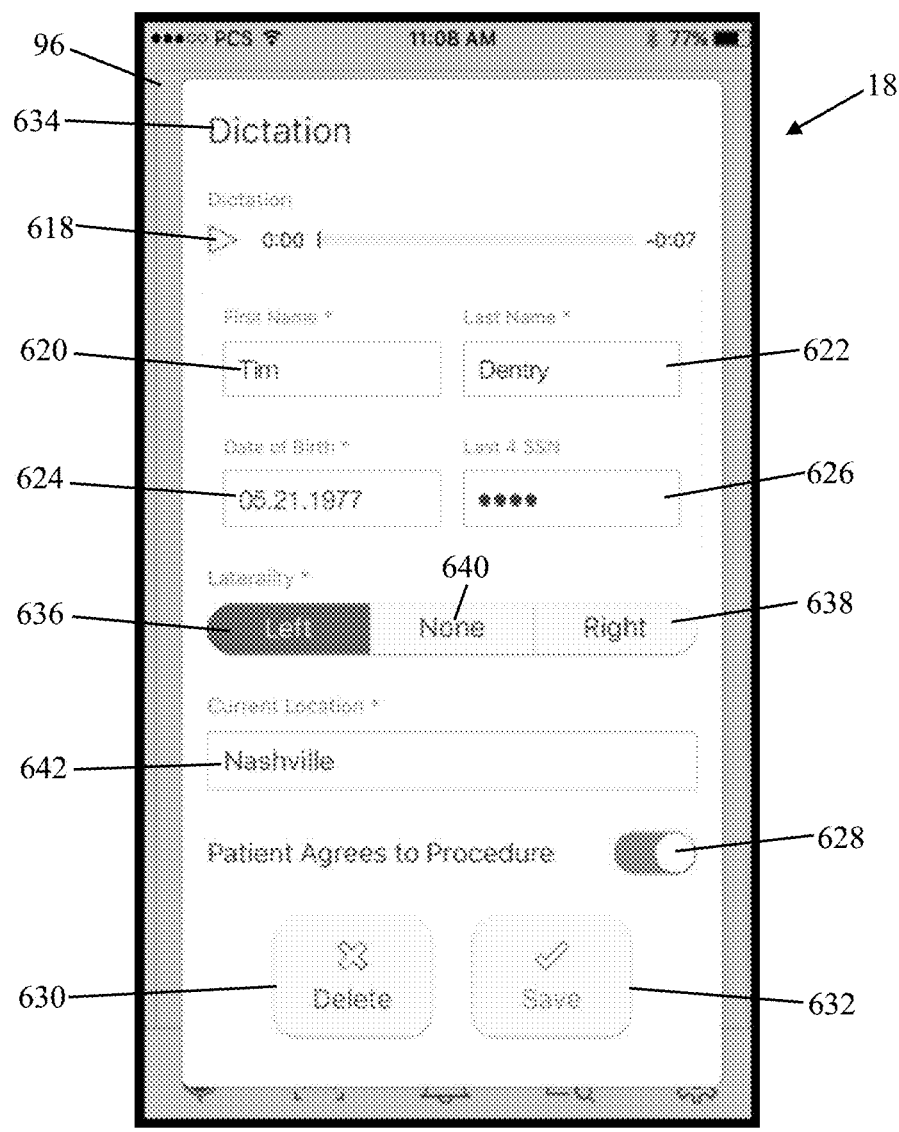
Figure 72:
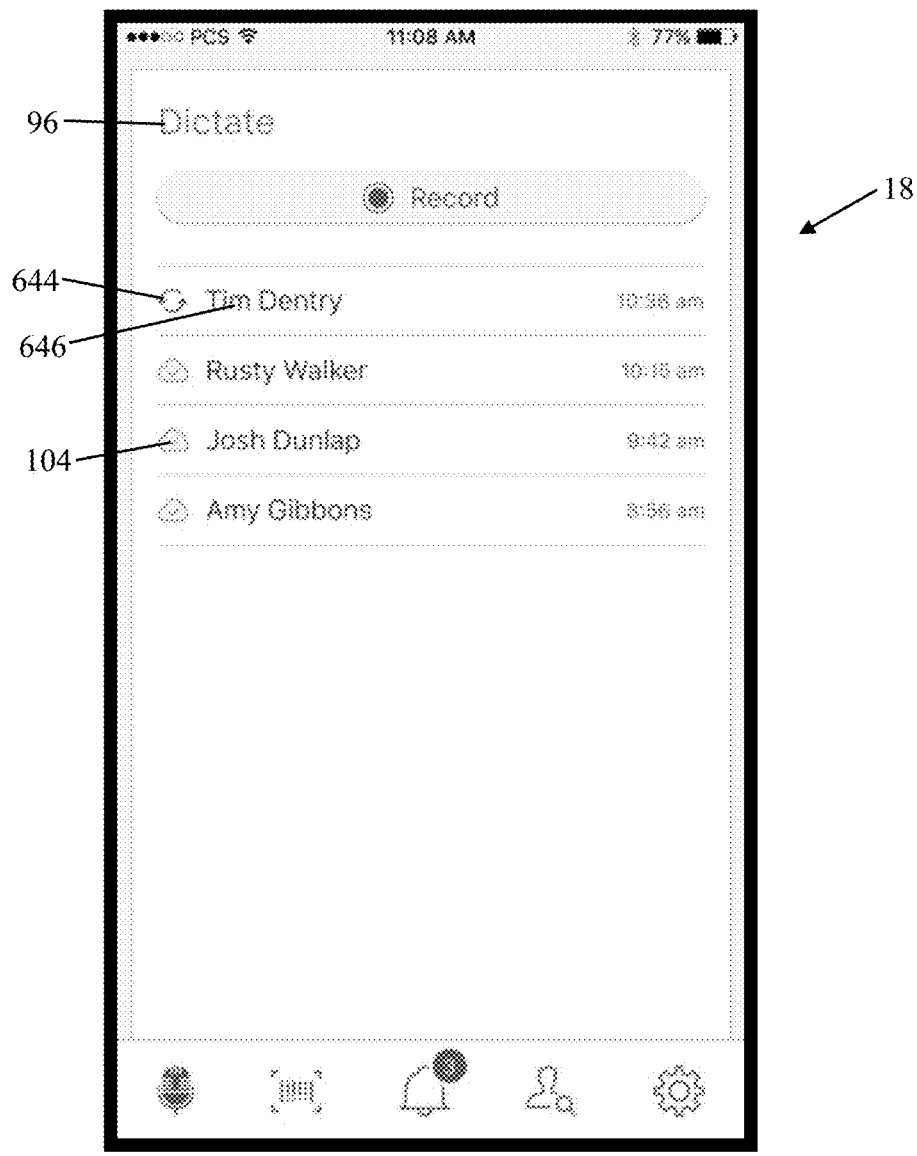

FIG. 70 shows the first pop-up window 616 of the Dictation GUI screen 96 with the information filled in for a fictitious patient "Tim Dentry", born May 21, 1977 (Social Security Number obscured). For explanation purposes, the surgery that Dr. Kelly and Mr. Dentry agreed upon was a right carpal tunnel release. The recording of Dr. Kelly's dictation (accessible by pressing the play icon 618) may include the following audio (by way of example): "This is Dr. Wayne Kelly and with me is patient Mr. Tim Dentry, date of birth May 21, 1977. I plan to perform a right carpal tunnel release on Mr. Dentry." The audio may optionally include the corresponding consent by Mr. Dentry, such as "I agree" or "Yes, I do" spoken by Mr. Dentry in response to Dr. Kelly's consent question, such as "Mr. Dentry, do you agree and consent to this procedure?" Once the information has been filled in and the patient has consented, the surgeon may operate the toggle 628 to reflect that consent has been obtained and click the Save 632 icon to save Mr. Dentry's name, date of birth, and SSN information, along with the audio dictation (surgeon and optionally patient's consent), as part of Mr. Dentry's patient profile. If an alternative pop-up window 634 (see FIG. 71) is used, the surgeon may also indicate laterality by clicking on the "Left" tab 636, the "Right" tab 638, or "None" tab 640. An indicating color, for example lavender, may be assigned to a left tab 636 click, red or rose, to a right tab 638 click, and a gray to a none tab 640 click. The procedure location 642 may also be entered. According to one aspect, the data may be saved to secure cloud-based data storage as de-identified/anonymized data or as identified data for use by the hospital system and/or insurance companies. A "working icon" 644 (see FIG. 72) may be provided adjacent to the new entry 646 for Tim Dentry to reflect that the data is in the process of being stored into the cloud. Upon completion, the working icon 644 will be replaced with a "check box" icons 104 shown adjacent to the prior patients.

Figure 73:
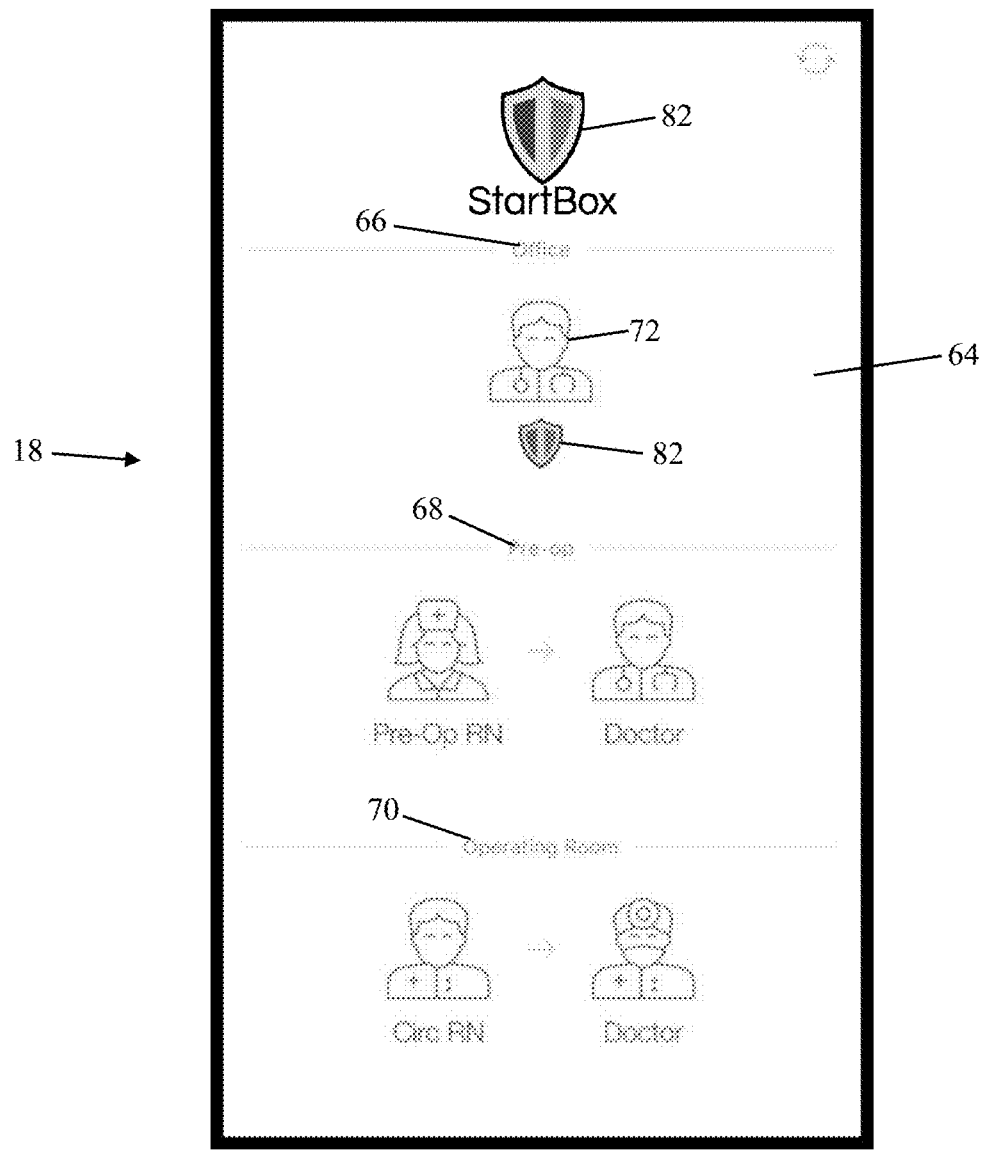

FIG. 73 shows the user-persona GUI screen 64 after the patient has progressed through the Office section 66 of the medical environment through the use of the system and methods of preventing wrong-site surgeries and blade-related injuries 10. For ease of understanding and quick visualization, a StartBox™ shield 82 is provided adjacent to the Doctor 72 persona to denote that the section has been completed. After the surgery is decided upon and consented (by the patient or guardian, as the case may be), the surgery will need to be scheduled and the patient admitted upon the day of surgery at the location of surgery (e.g. hospital or surgery center). This can be accomplished using the software system 12 as described above with reference to FIG. 63, specifically during stages 50-52. While described above in use with stationary computers 16, it will be appreciated that the steps of surgery scheduling 52 and/or patient admissions 54 may be performed via a hand-held device 18 running the app-version of the software system 12. If so, the app-version of the software system 12 (including the user-persona GUI screen 64 would need to be updated to reflect that change in personas interacting with and functions required to accomplish surgery scheduling and patient admissions.

Figure 74:
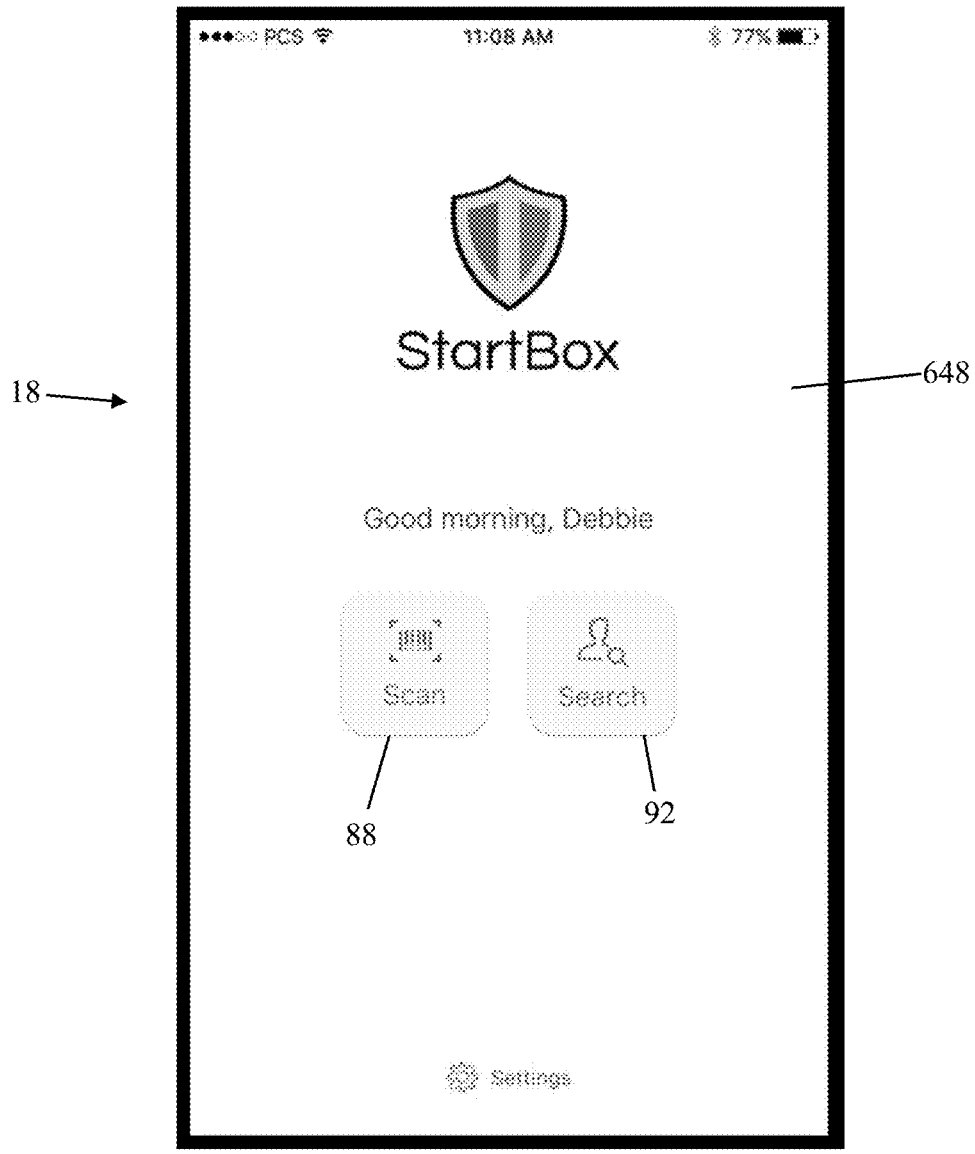

FIG. 74 illustrates an exemplary version where the app-version of the software system 12 is next used in pre-op section 68 following use in the surgeon's office section 66. When the patient has progressed to pre-op, pre-op personnel (such as a pre-operative RN 74) may use the system and methods of preventing wrong-site surgeries and blade-related injuries 10 via a hand-held device 18 running the app-version of the software system 12. The hand-held device 18 used by the pre-op RN 74 will likely be a different physical unit than that used by the surgeon 72 in his or her office. Either way, the pre-op RN 74 will need to use a password or other secure identifying information (e.g. biometrics such as retina scan, iris scan, touch-pad fingerprinting, face recognition) in order to access the functionality of the app-version of the software system 12. Once accessed, pre-established roles and privileges will dictate what functions and operations may be undertaken by the pre-op RN 74.

FIG. 14 shows an exemplary Pre-op RN GUI screen 648 that presents to the pre-op RN 74 after he or she accesses the system 10, including options to Scan 88 and Search 92. When the Scan 88 function is selected, scanning functionality within the handheld device 18 is activated and the app progresses to the Scan GUI screen 650 shown in FIG. 75. The handheld device 18 is positioned adjacent to the patient ID band 46 of the patient (in this case, Mr. Tim Dentry) and scanning function activated (automatically or manually) to capture the information on the patient ID band 46. In this embodiment, the scanner of the hand-held device 18 is capable of scanning the barcode or QR code 652 of the patient ID band 46. This is used to identify the patient using the information stored in the barcode 652 of the patient ID band 46. In addition to this type of identifying information, the handheld device 18 may include and/or interface with any number of biometric identification technologies, such as (but not necessarily limited to) iris scan, touch pad fingerprinting, genetic matching. The Search 92 icon allows the pre-op RN 74 to perform a variety of search queries, in the same manner described above with reference to the surgeon 72 in his or her office, and thus need not be repeated here.

Figure 75:
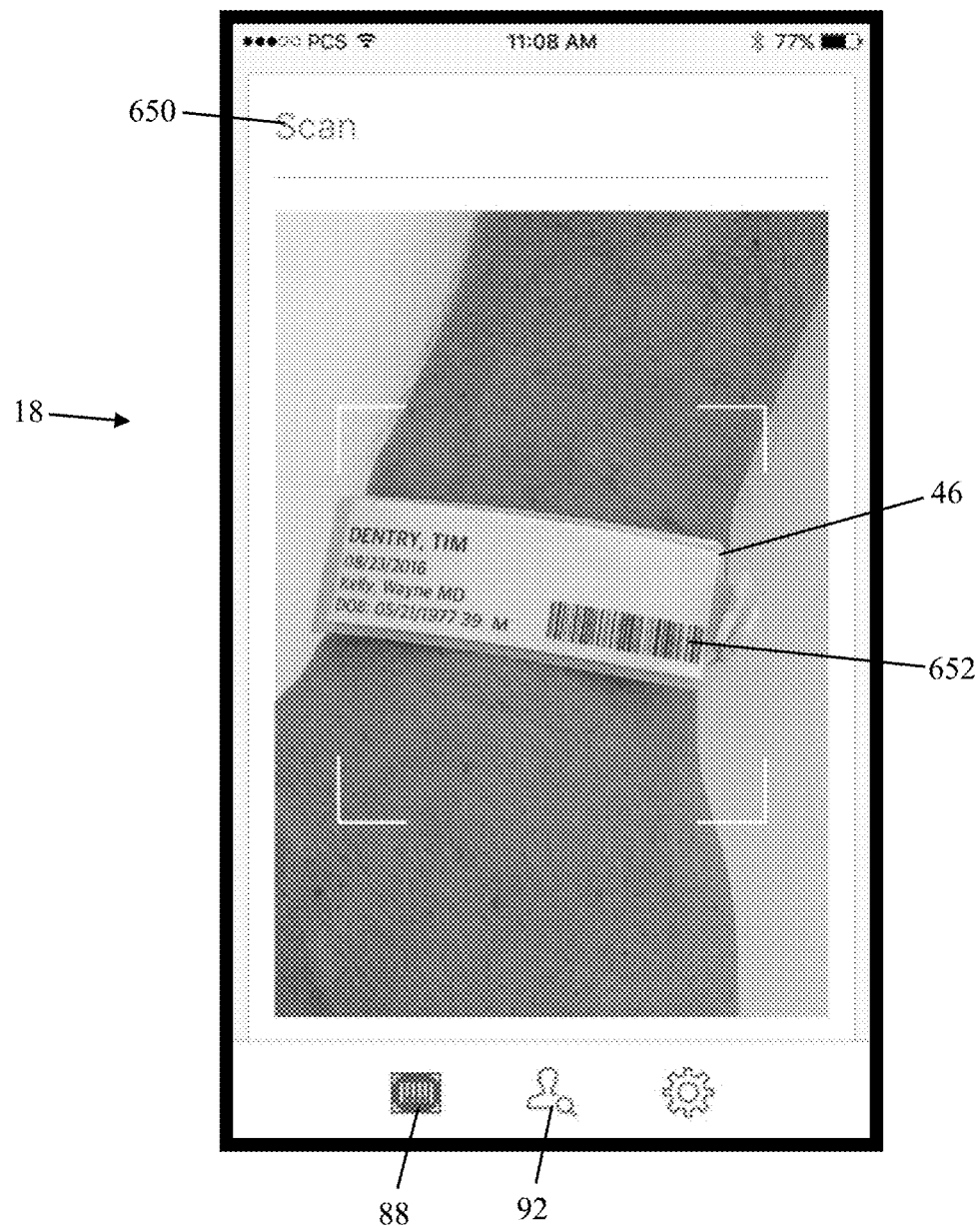
Figure 76:
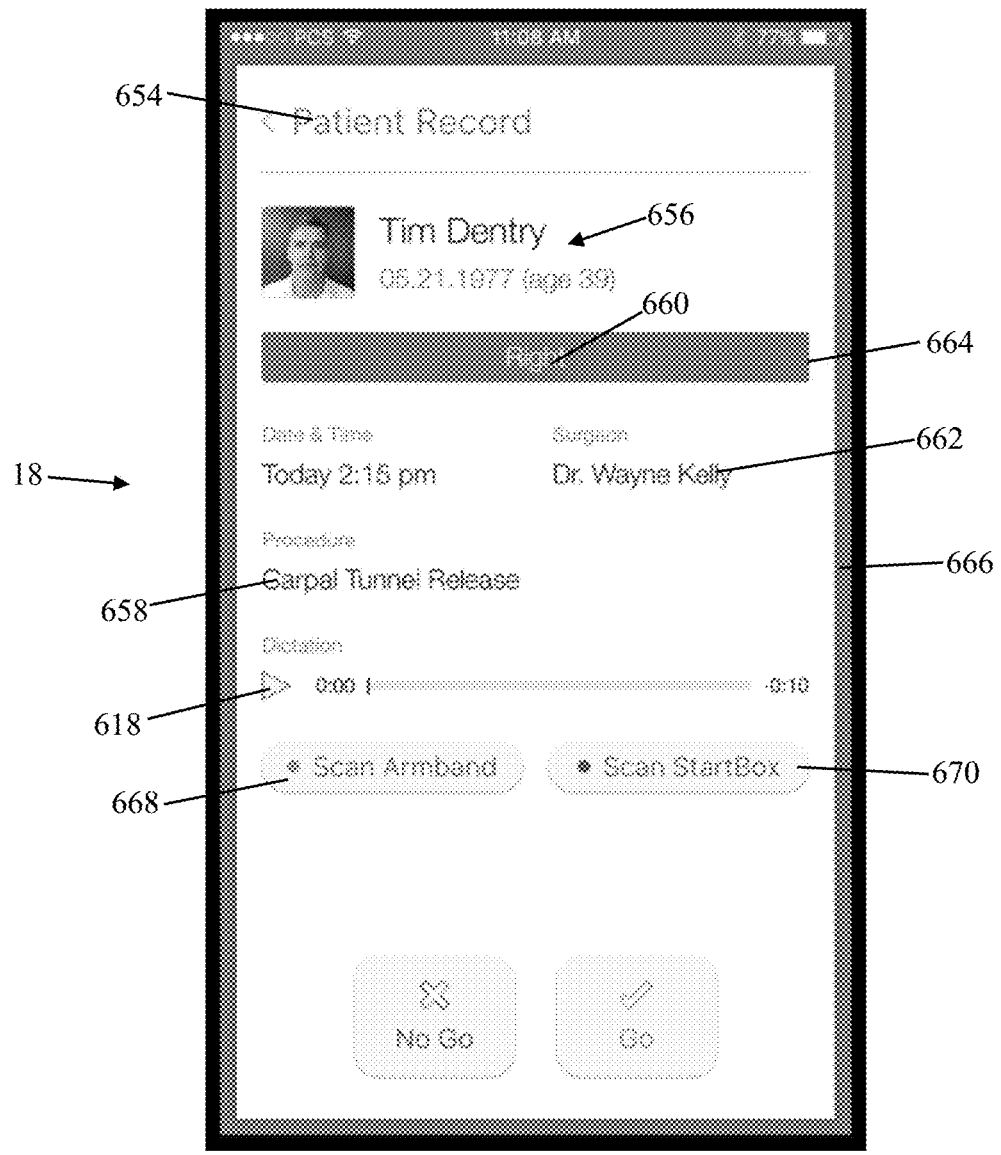

FIG. 76 illustrates an exemplary Patient Record GUI screen 654 that appears after the patient ID band 46 shown in FIG. 75 has been scanned by the hand-held device 18, including static information previously saved by others in the medical environment (e.g. surgeon's office, surgery scheduler, admissions, etc. . . . ) including demographic information 656 (name and age), surgical procedure 658, laterality 660 (color and name), and surgeon 662. The laterality 660 is visualized by box 664 colored in particular color to indicate laterality, for example a red color for right laterality and an outer colored boundary 666 colored in red as well. Playback icon 618 allows the pre-op RN 74 to play the audio-recording from the surgeon's office containing the intended-surgery information dictated by the surgeon and optionally the consent by the patient. The Scan Armband icon 668 will be illuminated green or another color indicating that the data from the patient ID band 46 has been incorporated into the system and methods of preventing wrong-site surgeries and blade-related injuries 10 by virtue of scanning the patient ID band 46 via the scanner of the hand-held device 18. At this point, the Scan StartBox icon 670 is red or a color indicating that the label of the safety blade-dispenser 14 needs to be scanned. The user (in this case, the pre-op RN 74) may then press the Scan StartBox icon 670 which opens a pop-up scan window 672 as shown in FIG. 77.

Figure 77:
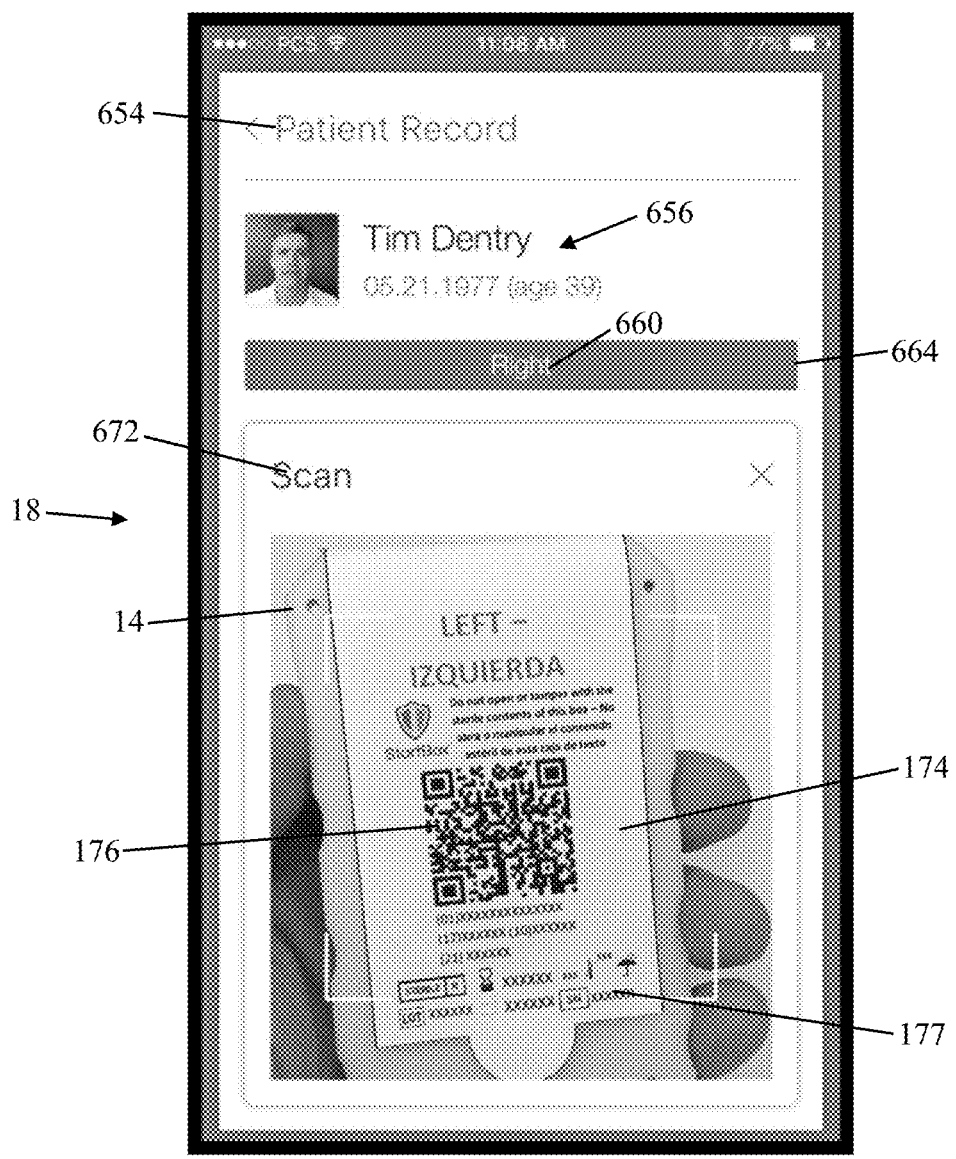

The patient record GUI screen 654 illustrated in FIG. 77 includes a pop-up scan window 672, demographic information 656 (name and date of birth) of the patient, and laterality 660 (color and name) of the procedure. The handheld device 18 is positioned adjacent to the label 174 of the safety blade-dispenser 14 and the scanning function activated (automatically or manually) to capture the information stored (by way of example only) in a QR code 176. The data on the QR code 176 of the label 174 of the safety blade-dispenser 14 includes a unique identifier or serial number (SN) 177 which includes data signifying the laterality (and color) associated with that specific safety blade-dispenser 14. The scanner of the hand-held device 18 will read the data from the label 174 and compare it against the previously saved patient information and/or intended-surgery information. In this example, the laterality of the procedure was determined to be right-sided by the surgeon in the office, which is correctly shown at band 664 as RIGHT (and colored red or rose) in FIG. 77. The label 174, however, is labeled "LEFT" above the QR code 176.

Figure 78:

FIG. 78 shows the "Laterality Mismatch" app screen 678 resulting from the comparison between the previously saved patient profile and the scanned label 174 of the safety blade-dispenser 14, including the "Laterality Mismatch" error notification 680 and "No Go" window 682. The Laterality Mismatch error 680 occurred because the previously saved patient profile within the system and methods of preventing wrong-site surgeries and blade-related injuries 10 had right-laterality while the newly scanned label 174 of the safety blade-dispenser 14 had left-laterality (name and lavender color). The No Go window 682 includes a replay button 618 to replay the original audio recording from the surgeon's office, which provides the ability to go straight to the source of the surgery decision to help determine whether and where (if anywhere) data errors occur in the patient profile. The No Go window 682 also includes data capture features to document the reasons of the No Go decision, including (by way of example only) Wrong StartBox checkbox 684, Wrong Laterality in Patient Record checkbox 686, and a Comment text box 688.

Figure 79:
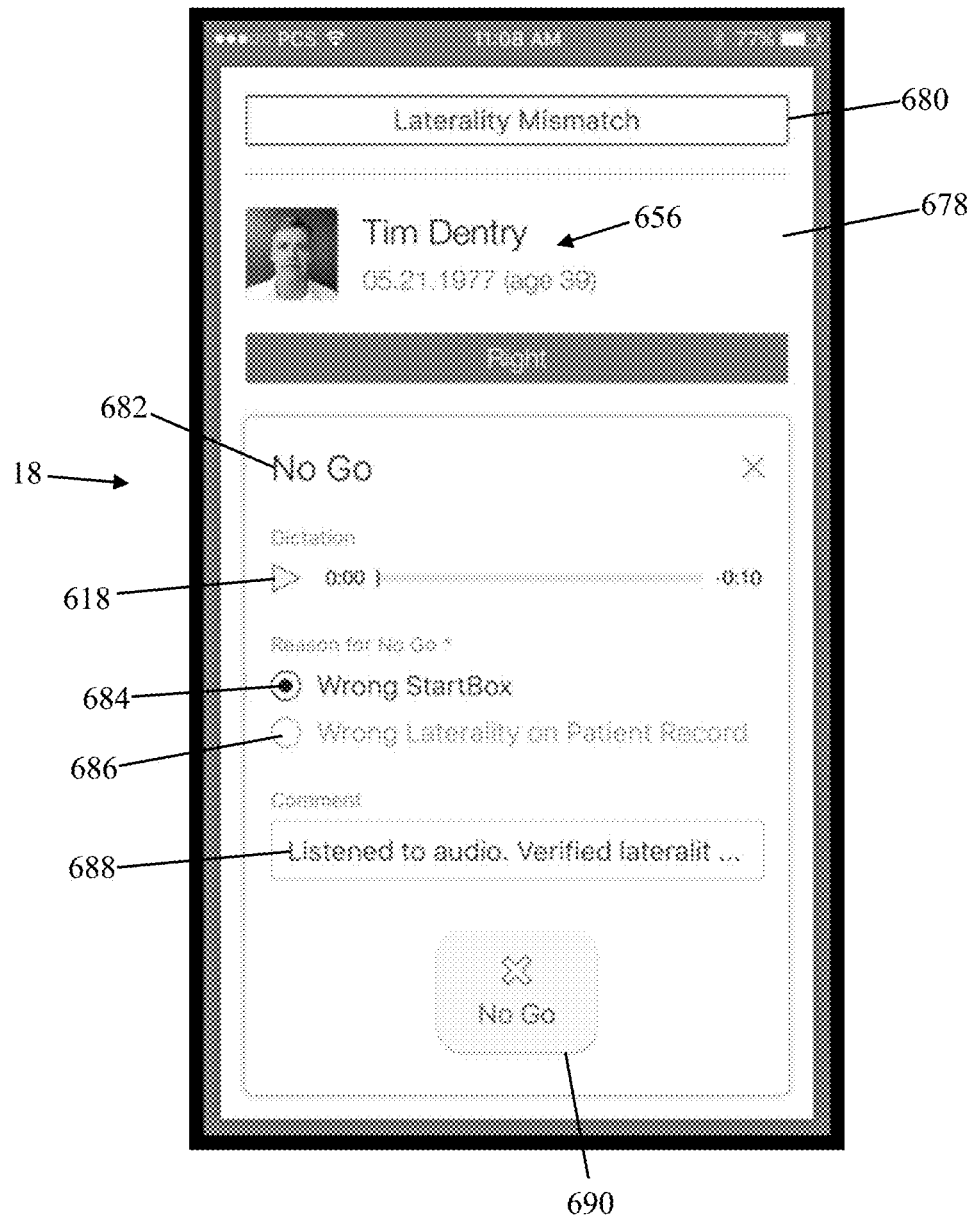

In this case, a safety blade dispenser 14 was selected by pre-op personnel with the wrong laterality (left), so as shown in FIG. 79 the pre-op RN 74 selected the "Wrong StartBox" checkbox 684 and added a comment in the Comment text box 688 to indicate what he or she did after the laterality mismatch was identified (e.g. "Listened to audio. Verified laterality. OR schedule was incorrect."). Because of the error, the pre-op RN 74 then selects the "No Go" button 690, which saves the No Go decision and underlying reasons and sends a "No Go" alert notification to the surgeon as shown in the next screen of FIG. 80. The "No Go" notification will not stop the perioperative process, but rather the surgeon will be required to review the No Go notification and decide whether it can be cleared or not before the final time-out. If yes, the final time-out (described below) can proceed. If not, the final time-out cannot be performed and the surgery will be cancelled.

Once the No Go notification is sent by the system and methods of preventing wrong-site surgeries and blade-related injuries 10 to the surgeon, the pre-op RN 74 will have a chance to remedy the problem to allow the perioperative process to continue. Each remediation will be dependent upon the type of error code, which may include (but is not necessarily limited to) Laterality Mismatch, Wrong Procedure, Wrong Patient, Wrong Dictation, Wrong Date of Birth, Patient Denied Procedure, and Other. In this case, the remediation involves discarding the incorrect safety blade-dispenser 14 (due to the left-laterality) and replace it with a new safety blade dispenser 14B with right-laterality. For other error codes, different remediation steps may be required, including surgeon intervention at that point to remedy the problem or cancel the surgery.

Figure 80:
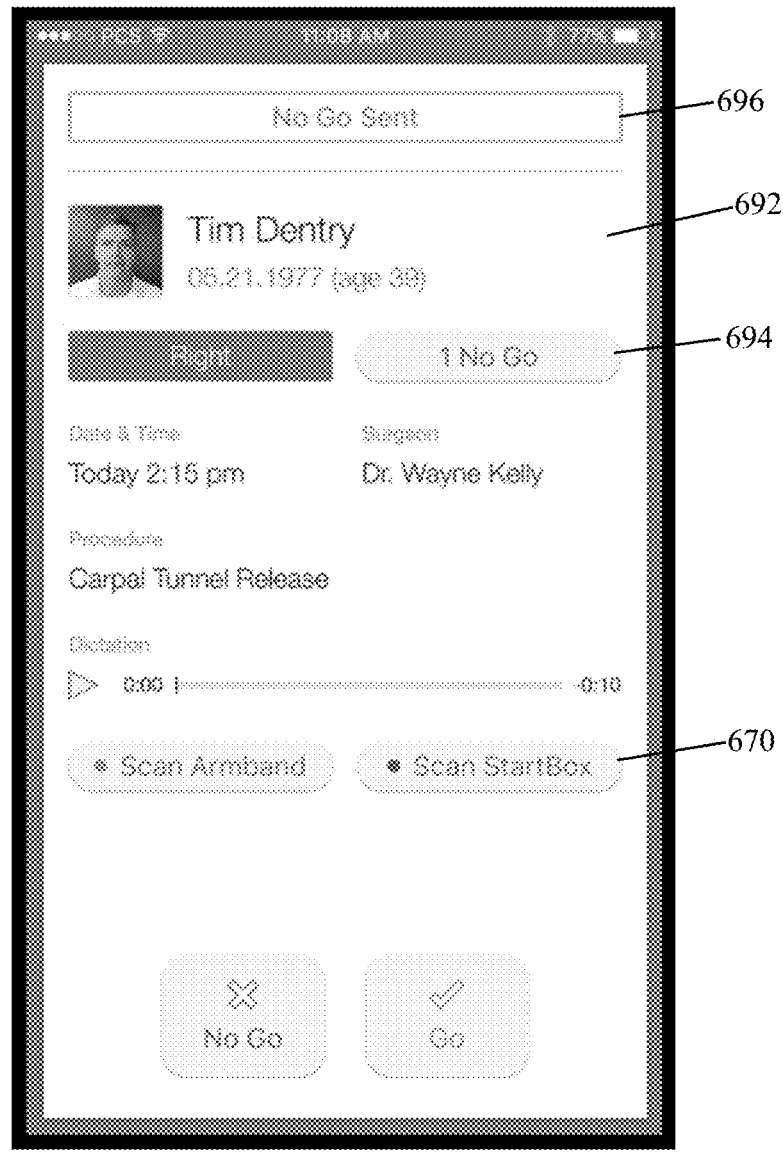
Figure 81:
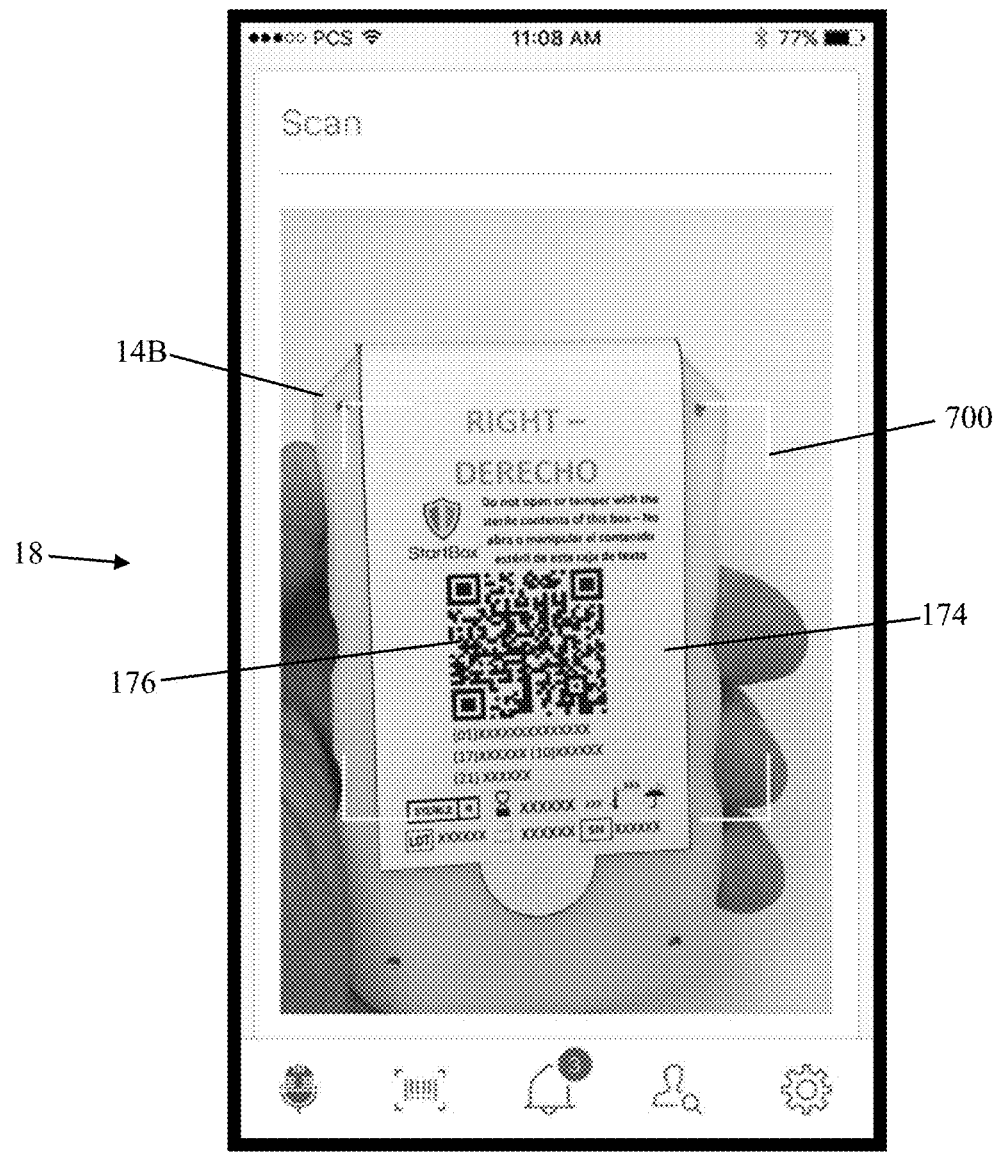
Figure 82:
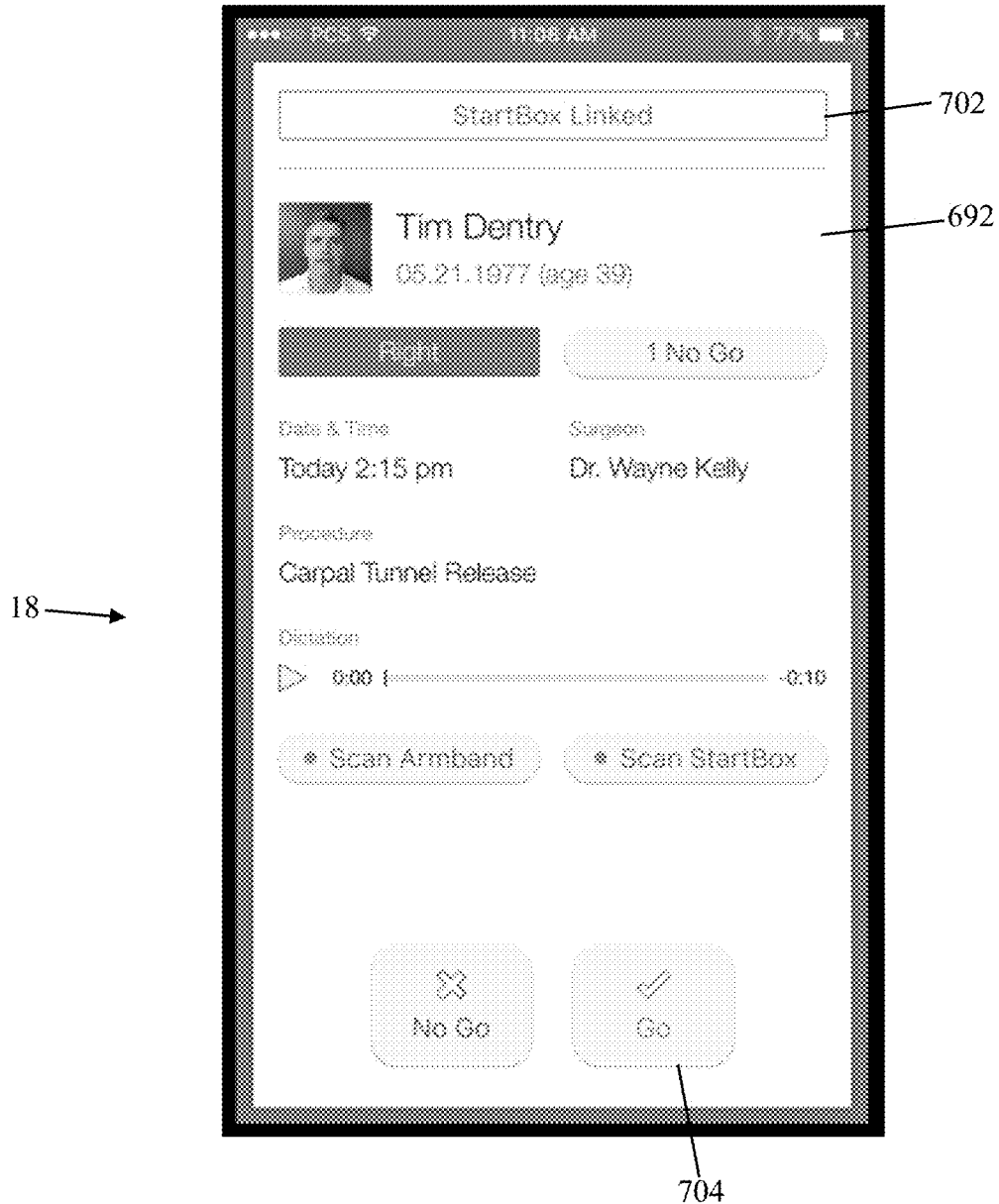
Figure 83:
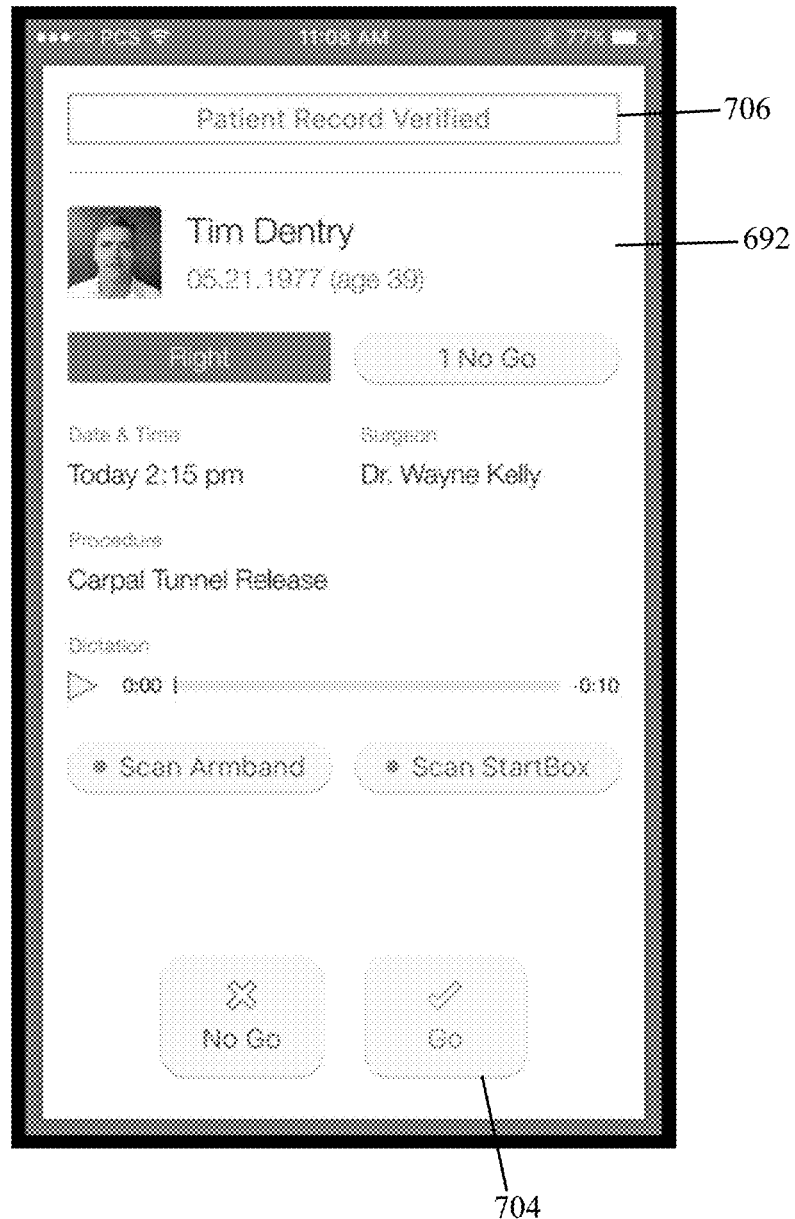

FIG. 80 illustrates an exemplary "No Go" remediation GUI screen 692 after the No Go notification has been sent and before the problem has been remediated (in this case, by the pre-op RN 74), which is identical to the Patient Record GUI screen 654 of FIG. 66 except for the inclusion of a "No Go" counter 694 and a "No Go Sent" notification banner 696. With the laterality mismatch corrected, the pre-op RN 74 may then select the "Scan StartBox" 670 icon to activate the scanner 700 of the hand-held device 18 as shown in FIG. 81. The QR code 176 of the new safety blade-dispenser 14B (which is designated right-laterality via name (RIGHT) and red or rose color) may then be scanned and compared to the previously saved patient profile and/or intended-surgery information. Because the laterality now matches, the new safety blade-dispenser 14B may be linked with the patient profile, and the No Go notification banner 696 appearing previously on the No Go remediation GUI 692 is replaced by a "StartBox Linked" notification banner 702 as shown in FIG. 82. The pre-op RN 74 may thereafter select the "GO" icon 704 to verify the patient record as denoted by the "Patient Record Verified" notification banner 706 (shown in FIG. 83), after which point the pre-op RN may select the "GO" icon 704 shown in FIG. 83 in order to close out that stage in the process.

Figure 84:
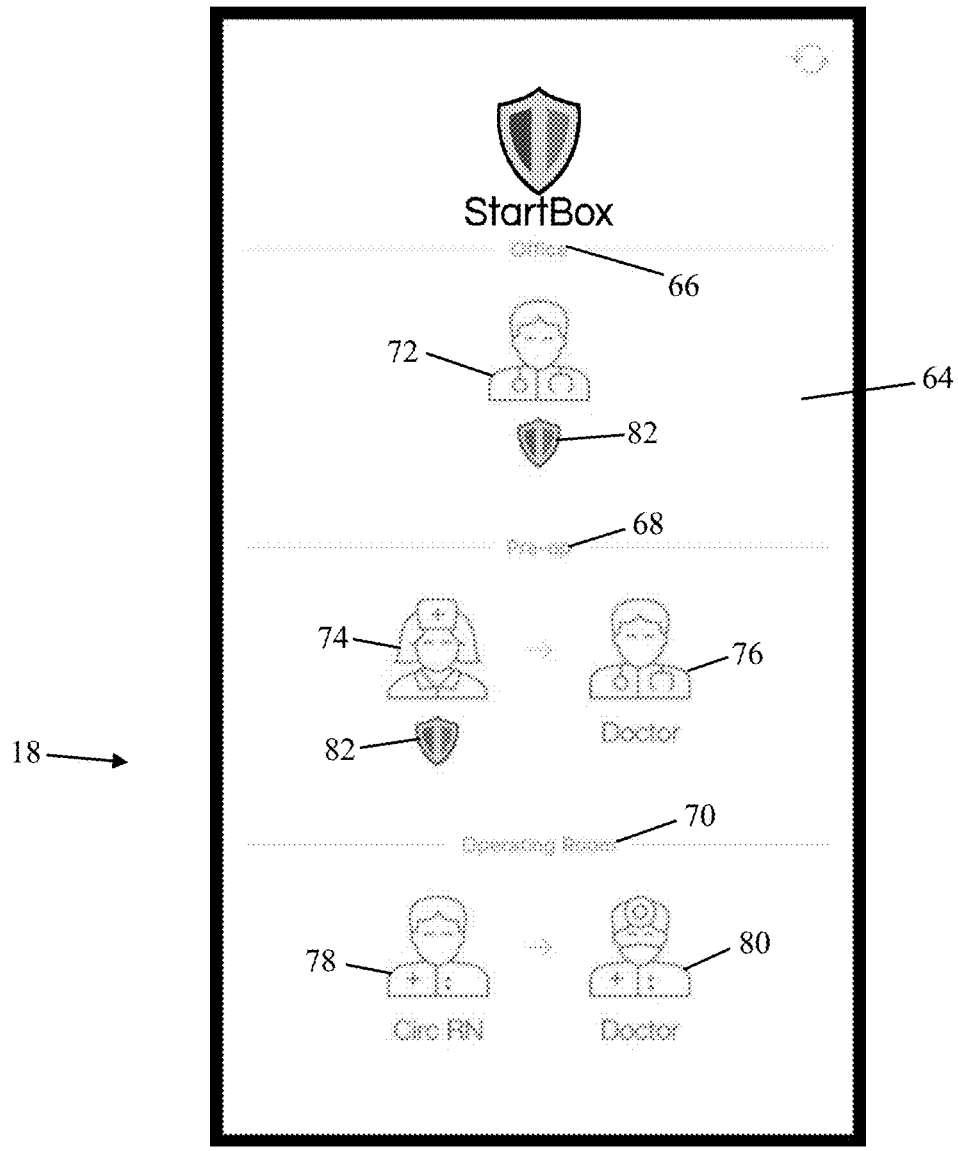

FIG. 84 shows an exemplary user persona GUI screen 64 that presents to the doctor 76 during the pre-op phase 68. In this case a StartBox icon 82 appears underneath the Pre-op RN 74 icon indicating that the steps pertaining to the Pre-op RN 74 have been completed.

Figure 85:
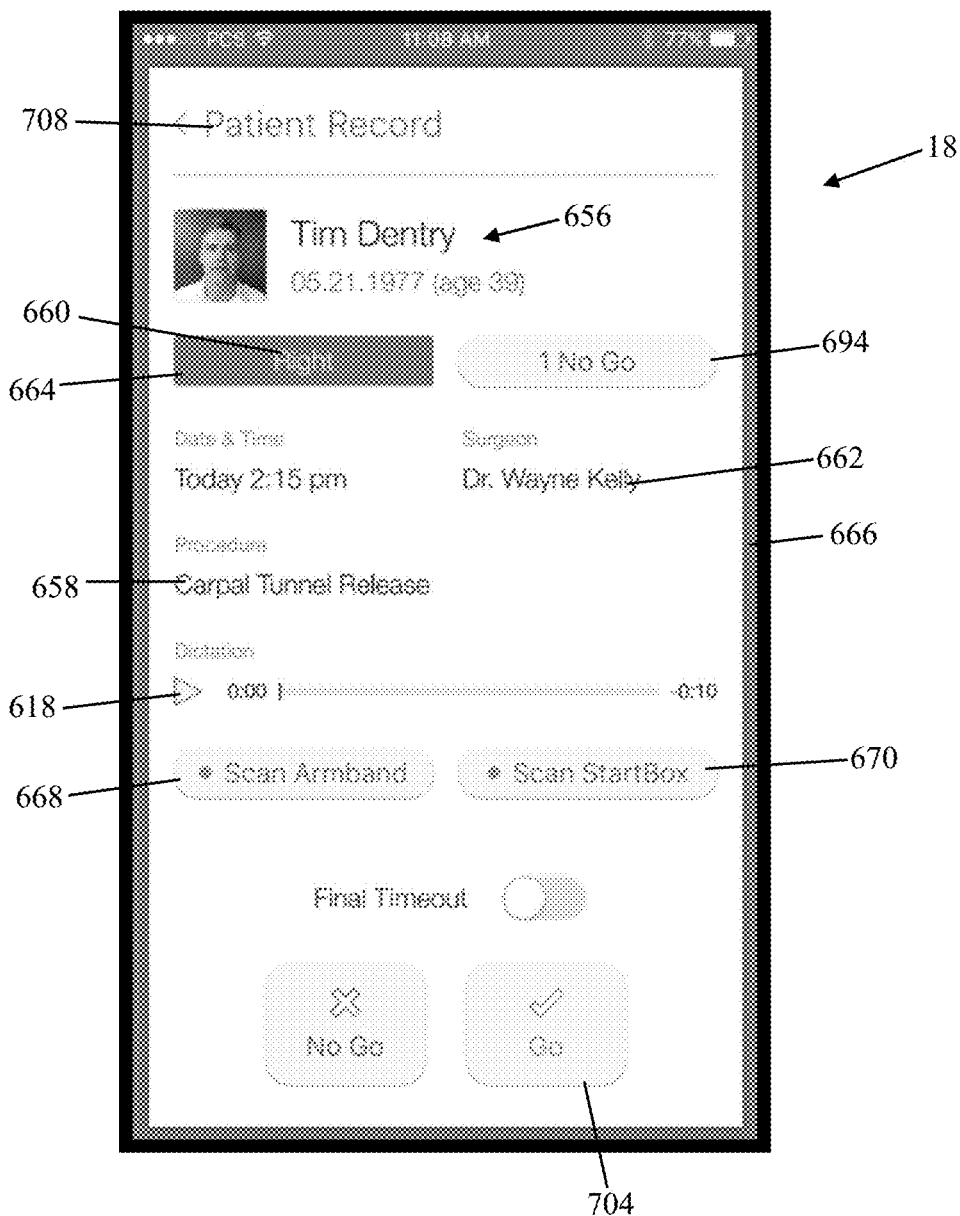
Figure 86:
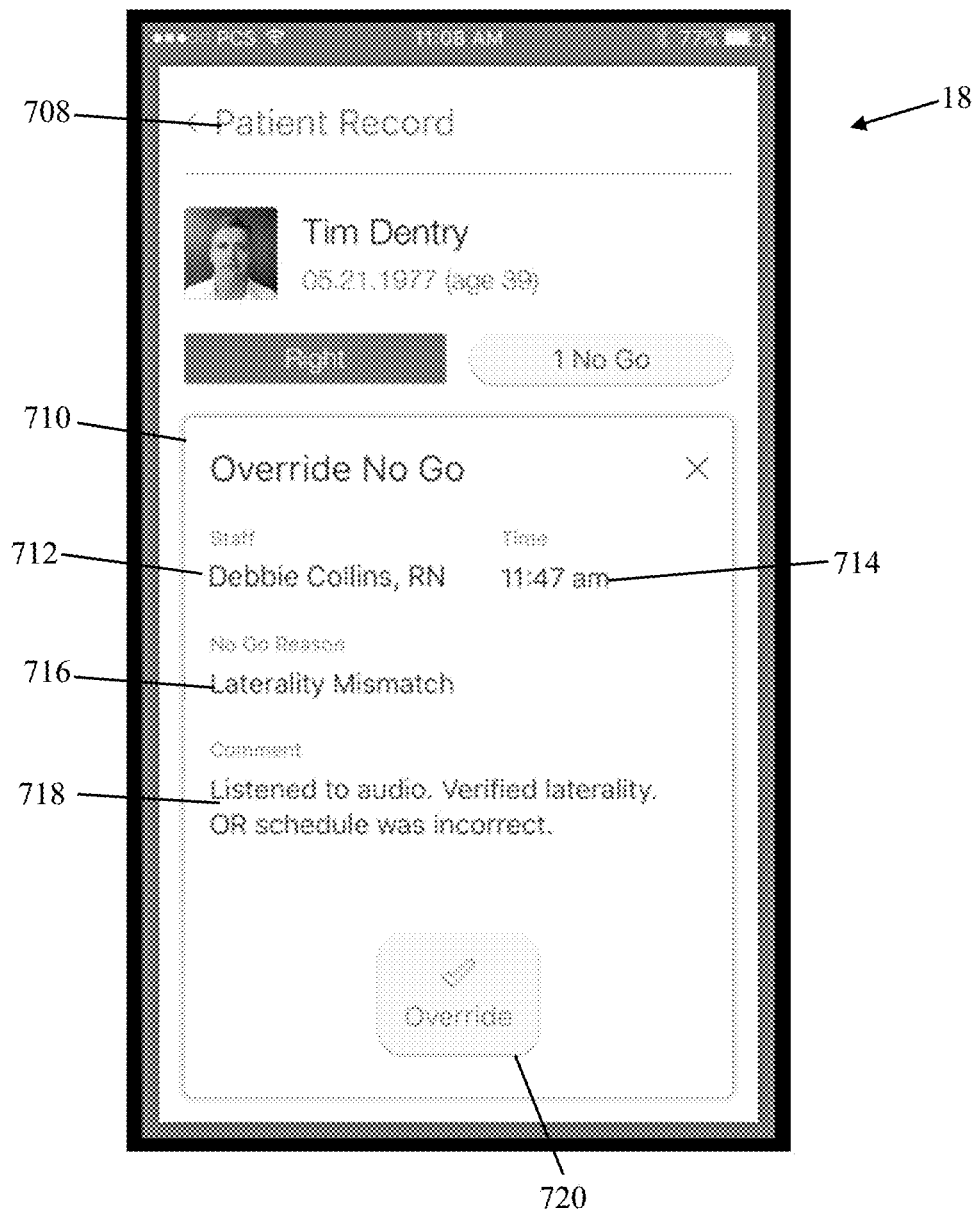

FIG. 85 illustrates the Pre-Op Patient Record GUI screen 708 after the patient ID band 46 shown in FIG. 75 has been scanned by the hand-held device 18, including static information previously saved by others in the medical environment (e.g. surgeon's office, surgery scheduler, admissions, etc. . . . ) including demographic information 656 (name and age), surgical procedure 658, laterality 660 (color and name), and surgeon 662. The laterality is visualized by box 664 colored in particular color to indicate laterality, for example a red color for right laterality and an outer colored boundary 666 colored in red as well. The playback 618 allows the pre-op doctor 76 to play the audio-recording from the surgeon's office containing the intended-surgery information dictated by the surgeon and optionally the consent by the patient. The Scan Armband icon 668 will be illuminated green or a color indicating that the data from the patient ID band 46 has been incorporated into the system and methods of preventing wrong-site surgeries and blade-related injuries 10 by virtue of scanning the patient ID band 46 via the scanner of the hand-held device 18. At this point, the Scan StartBox icon 670 is red or a color indicating that the label of the safety blade-dispenser 14 needs to be scanned. The doctor 76 may then press the GO 704 in order to advance to the next screen shown in FIG. 86.

Since there was a laterality mismatch, an "Override No Go" pop-up screen 710 is shown with information regarding the prior "No Go" selection, including (but not limited to) the name of nurse 712, the time 714 of the No Go, and reason 716 for No Go. In comment section 718, notes indicate that the nurse or doctor listened to the audio and confirmed the correct laterality. To continue in the process, the doctor touches the Override button 720.

Figure 87:
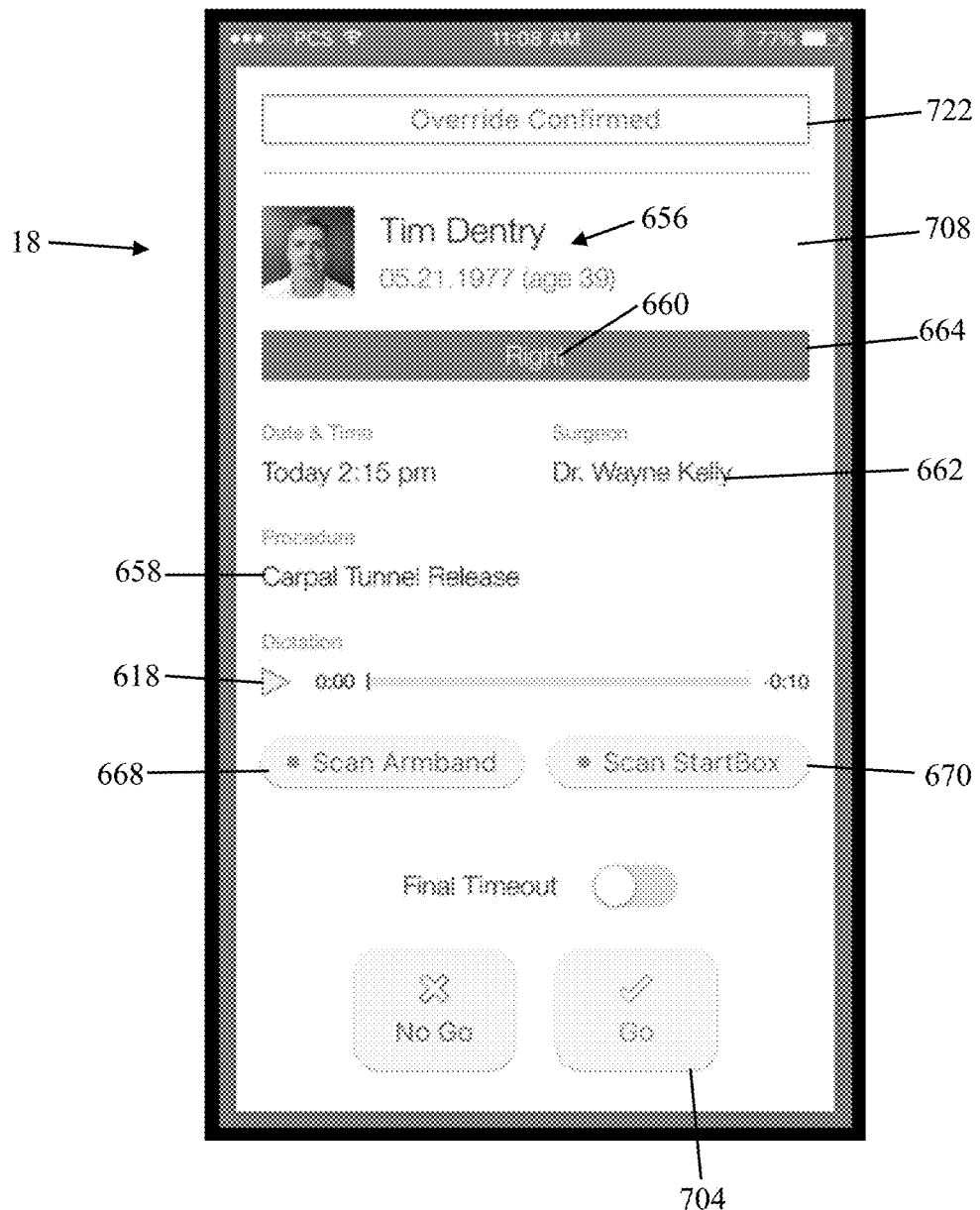

FIG. 87 illustrates the Pre-Op Patient Record GUI screen 708 once the Override button 720 has been activated and the doctor 76 scans the patient. An override confirmed notification banner 722 is displayed, along with including static information previously saved by others in the medical environment (e.g. surgeon's office, surgery scheduler, optionally any pre-surgical work-up/clearance, admissions, etc. . . . ) including demographic information 656 (name and age), surgical procedure 658, laterality 660 (color and name), and surgeon 662. The laterality is visualized by box 664 colored in particular color to indicate laterality, for example a red color for right laterality and an outer colored boundary 666 colored in red as well. The playback 618 allows the doctor 76 to play the audio-recording from the surgeon's office containing the intended-surgery information dictated by the surgeon and optionally the consent by the patient. The Scan Armband icon 668 will be illuminated green or a color indicating that the data from the patient ID band 46 has been incorporated into the system and methods of preventing wrong-site surgeries and blade-related injuries 10 by virtue of scanning the patient ID band 46 via the scanner of the hand-held device 18. At this point, the Scan StartBox icon 670 is red or a color indicating that the label of the safety blade-dispenser 14B needs to be scanned. The doctor 76 may then press the GO icon 704 in order to advance to the next screen shown in FIG. 88.

Figure 88:
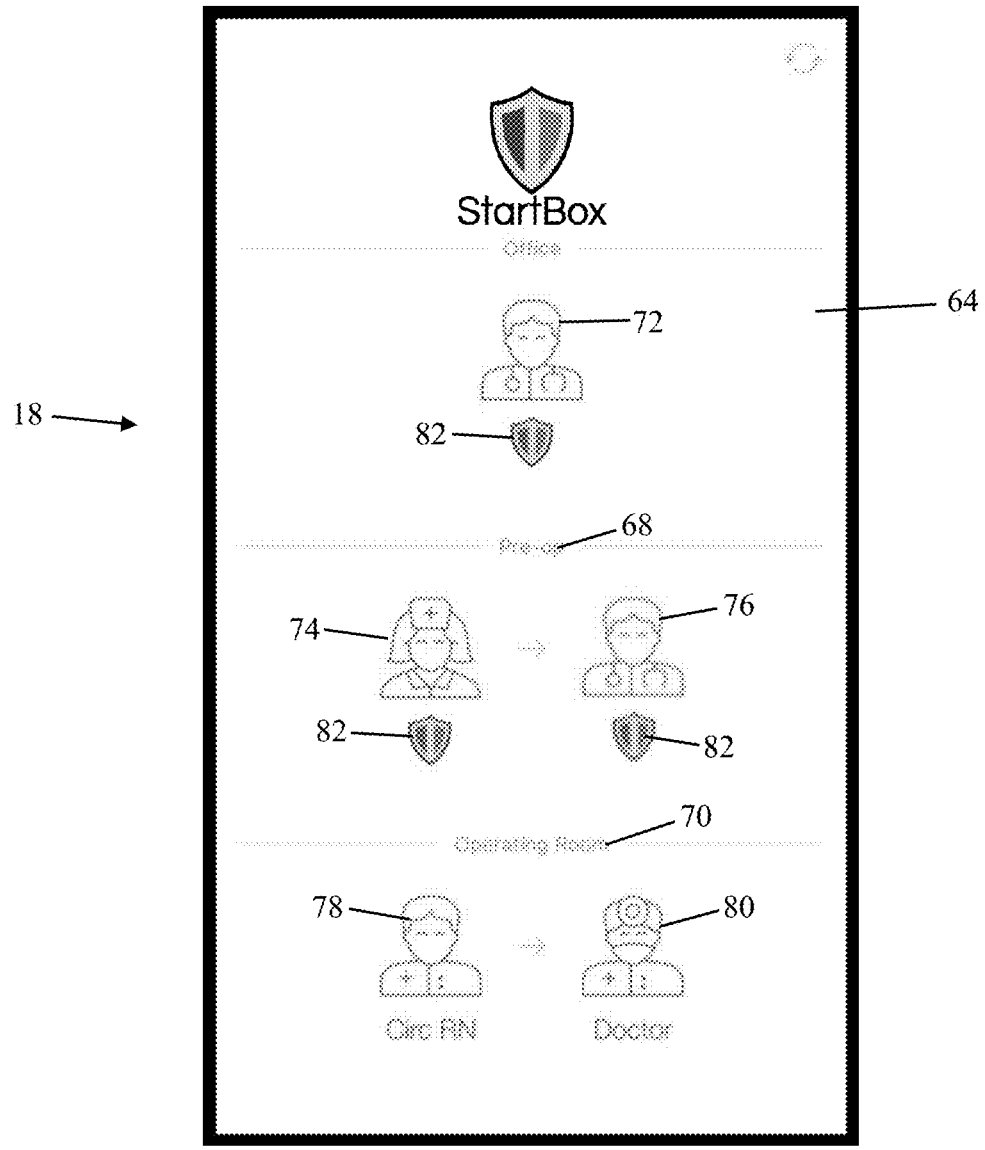

FIG. 88 shows an exemplary user persona GUI screen 64 that presents to the circulating nurse 78 during the Operating Room (OR) phase 70. In this case a StartBox icon 82 appears underneath the Pre-op doctor 76 icon indicating that the steps pertaining to the Pre-op doctor 76 have been completed.

Figure 89:
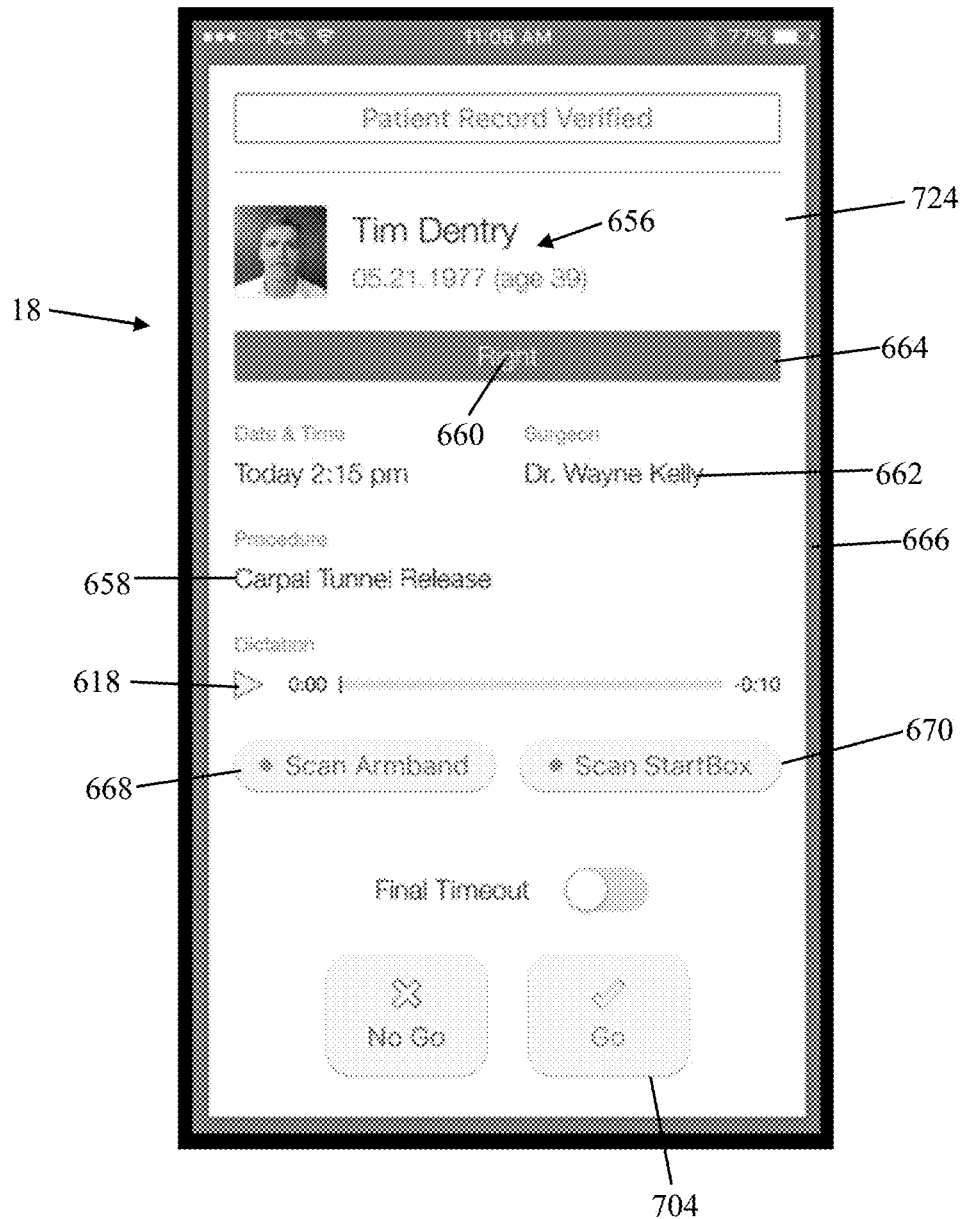

FIG. 89 illustrates the OR phase Patient Record GUI screen 224 after the patient ID band 46 shown in FIG. 75 has been scanned by the hand-held device 18, including static information previously saved by others in the medical environment (e.g. surgeon's office, surgery scheduler, admissions, etc. . . . ) including demographic information 656 (name and age), surgical procedure 658, laterality 660 (color and name), and surgeon 662. The laterality is visualized by box 664 colored in particular color to indicate laterality, for example a red color for right laterality and an outer colored boundary 666 colored in red as well. The playback 618 allows the circulating RN 78 to play the audio-recording from the surgeon's office containing the intended-surgery information dictated by the surgeon and optionally the consent by the patient. The Scan Armband icon 668 will be illuminated green or a color indicating that the data from the patient ID band 46 has been incorporated into the system and methods of preventing wrong-site surgeries and blade-related injuries 10 by virtue of scanning the patient ID band 46 via the scanner of the hand-held device 18. At this point, the Scan StartBox icon 670 is red or a color indicating that the label of the safety blade-dispenser 14B needs to be scanned. The circulating RN 78 then press the GO icon 704 in order to advance to the next screen shown in FIG. 90.

Figure 90:
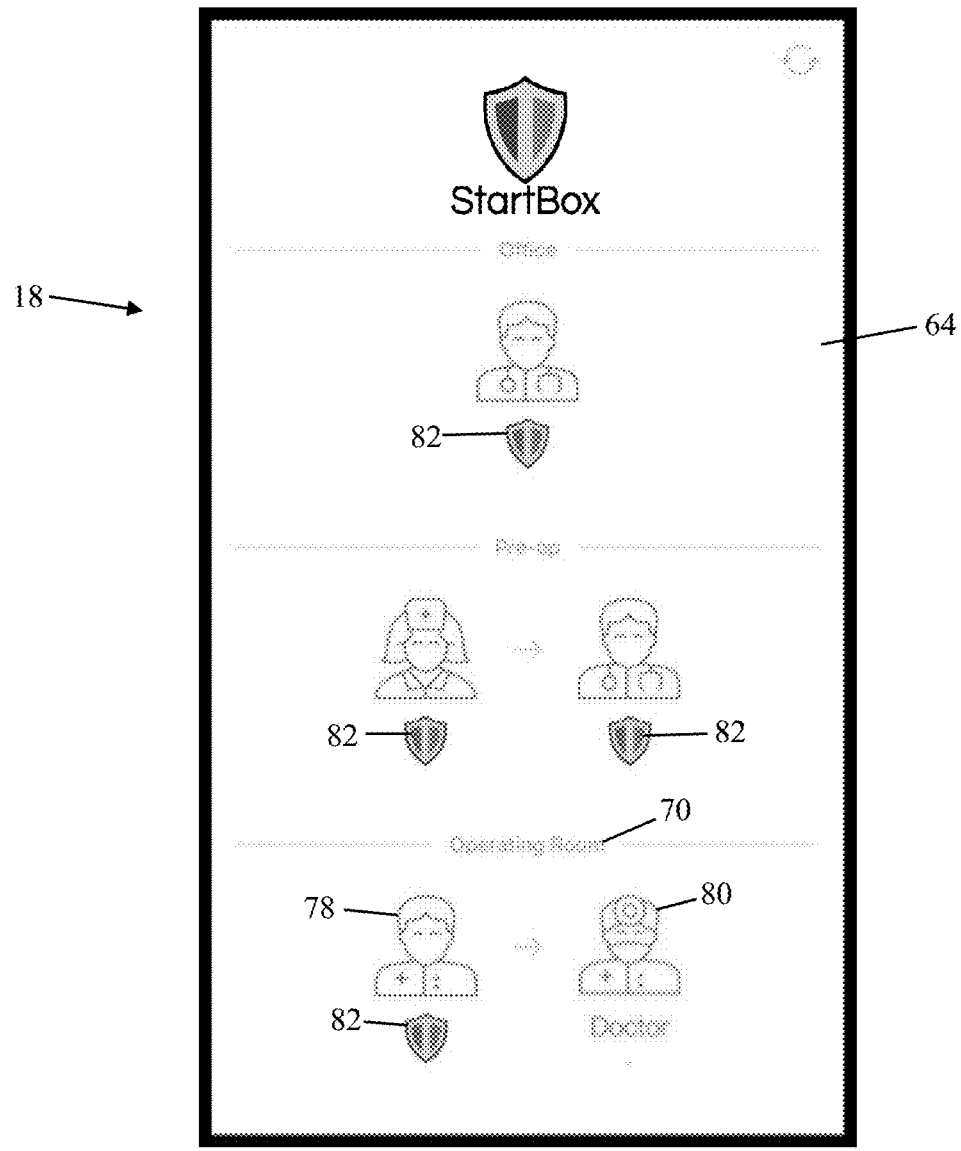

FIG. 90 shows an exemplary user personal GUI screen 64 that presents to the OR doctor 80 while in the OR 70 and just prior to performing a final timeout. In this case a StartBox icon 82 appears underneath the Circulating RN 78 icon indicating that the steps pertaining to the Circulating RN 78 have been completed.

Figure 91:
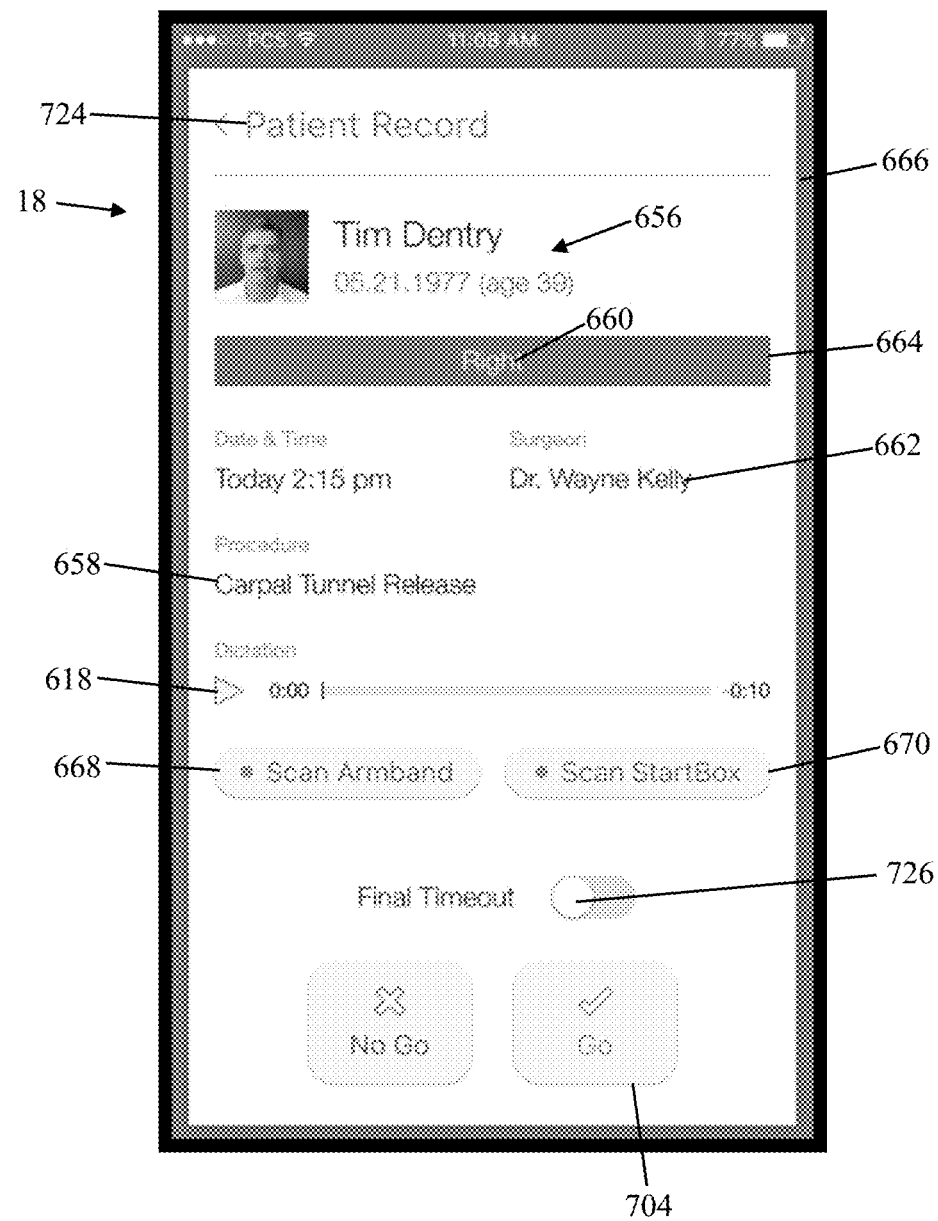
Figure 92:
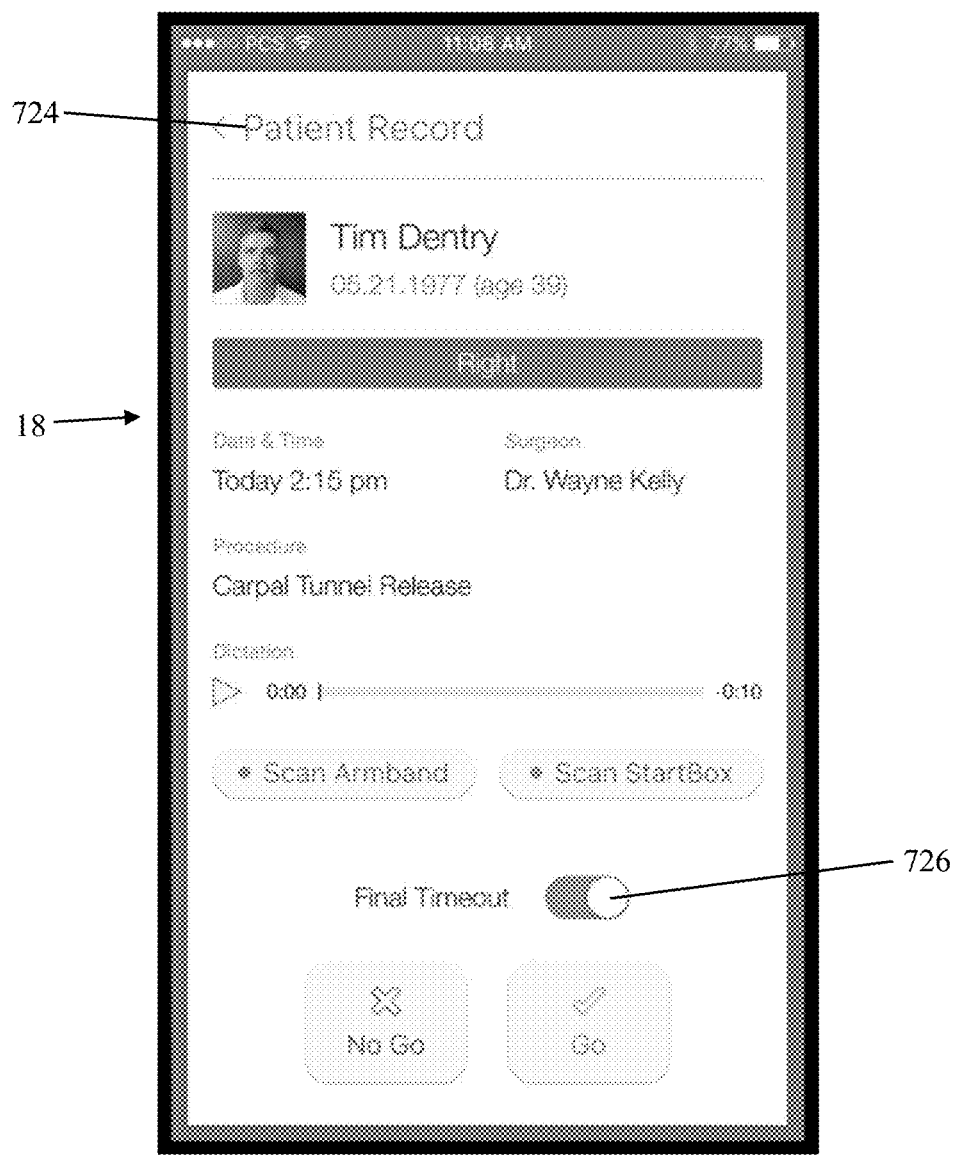

FIG. 91 illustrates the OR phase patient record GUI screen 724 after the patient ID band 46 has been scanned by the hand-held device 18, including static information previously saved by others in the medical environment (e.g. surgeon's office, surgery scheduler, admissions, and other patient-medical personnel interactions) including demographic information 656 (name and age), surgical procedure 658, laterality 660 (color and name), and surgeon 662. The laterality is visualized by box 664 colored in particular color to indicate laterality, for example a red color for right laterality and an outer colored boundary 666 colored in red as well. The playback 618 allows the OR doctor 80 to play the audio-recording from the surgeon's office containing the intended-surgery information dictated by the surgeon and optionally the consent by the patient. The Scan Armband icon 668 will be illuminated green or a color indicating that the data from the patient ID band 46 has been incorporated into the system and methods of preventing wrong-site surgeries and blade-related injuries 10 by virtue of scanning the patient ID band 48 via the scanner of the hand-held device 18. At this point, the Scan StartBox icon 670 is red or a color indicating that the label of the safety blade-dispenser 14B needs to be scanned. The OR doctor 80 may then press the GO icon 704 in order to advance to the next screen shown in FIG. 92.

Figure 93:
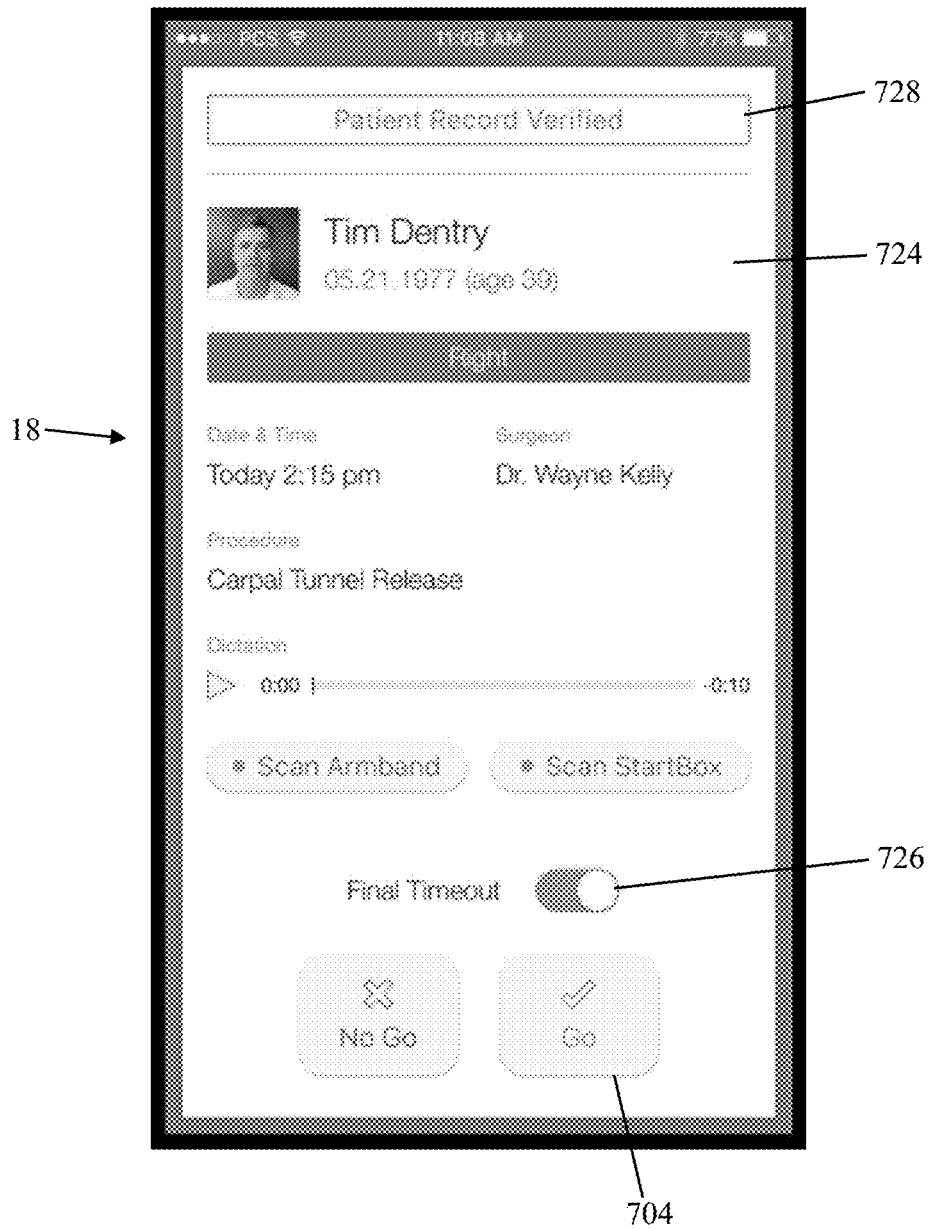

Once verified, the doctor activates the final timeout slide bar 726 (FIG. 92) to indicate that the OR doctor 80 has performed the last check to insure the patient, procedure, and laterality is correct and the procedure can be commenced. FIG. 93 shows the OR phase patient record GUI screen 724 after the OR doctor 80 has activated the Go button 704. The patient record has been verified as indicated by the "Patient Record Verified" notification banner 728 and the Final Timeout activation has been noted. The OR doctor 80 then activates the final Go button 704 before surgery begins.

Figure 94:
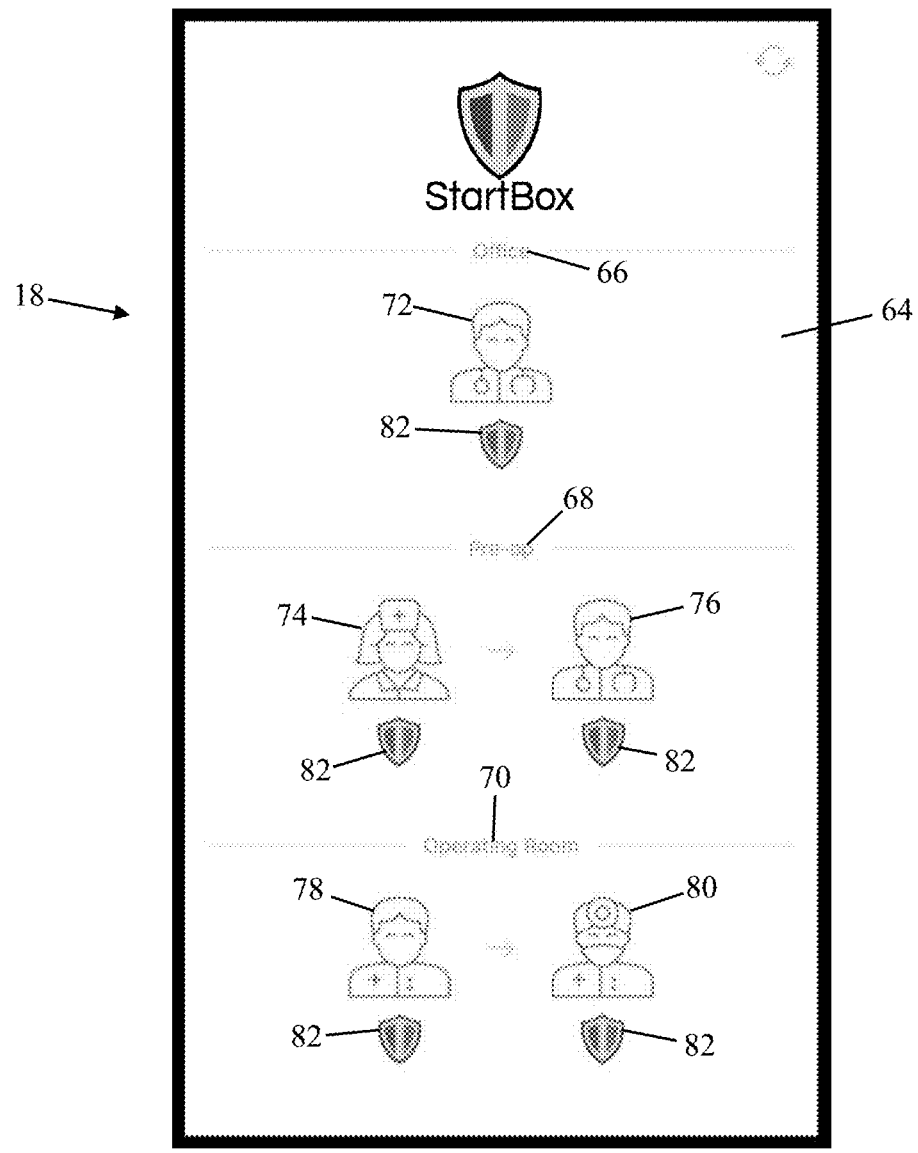

FIG. 94 illustrates the user-persona GUI screen 64 after all parts of the method have been completed and the surgery has begun. In this case a StartBox icon 82 appears underneath the OR Doctor 80 icon indicating that the steps pertaining to the OR Doctor (most notably the Final Timeout) have been completed. At this point the confirmation label 174 on the safety-blade dispenser 14 may be removed and affixed to the patient's chart (or other suitable location), allowing the surgeon access to the surgical blades needed to perform the procedure.

The system 10 of the present disclosure (as described above) may include an additional feature regarding imaging the patient for the intended surgery. More specifically, the software system 12 (whether used on computer 16 or hand-held device 18) may allow the surgeon to specify that the patient undergo certain pre-surgical imaging (such as computed tomography (CT), positron emission tomography (PET, etc. . . . ) for use in the pre-surgical work-up or clearances as well as during the surgery. For example, the software 12 may be configured such that the surgeon (at the Decision stage 50 in FIG. 63) may select or toggle a "Imaging Required" option, along with the ability to designate or describe the specific imaging he or she is requesting, which may be saved in the patient's electronic profile. If imaging is required, this information may be used by the surgery scheduler (at stage 52 of FIG. 63) to help schedule the requested imaging. The software 12 may also include related functionality for use as the patient continues through the medical, such as (but not necessarily limited to) providing a selection or toggle an "Imaging Available" option, wherein medical personnel (e.g. pre-op personnel) can check the system 10 to ensure the requested imaging is, in fact, available for use by the surgeon in the OR. If it is not, they can toggle or indicate that no imaging is available and select "No Go" so the surgeon may review and decide whether to pursue surgery without the requested imaging. The software 12 may also include functionality that allows the surgeon to review the imaging, if available, and optionally select or toggle an "Imaging Reviewed" option. Providing the ability for a surgeon to request and review imaging may help safeguard against the possibility that imaging read by other medical professionals (e.g. radiologists) may have been performed or documented inaccurately, which may cause inaccurate information to be in the patient profile. In this case, the surgeon can assess the imaging directly in the OR (or after admission) and determine if any such mistakes were made. If not, the surgery can continue. If so, the surgery can be stopped.

As previously mentioned, the system of preventing wrong-site surgeries and blade-related injuries 10 allows for tracking of a variety of data from pre-hospitalization to the actual surgical procedure, which the software system 12 can use to generate any of a variety of analytics 48. Analytics generally fall into one of five categories: descriptive, diagnostic, discovery, predictive, and prescriptive. Descriptive analytics for the most part comprise raw data pertaining to surgical events that may be collected by the system 10. These may be based upon, but not necessarily limited to, so-called "near miss" data (that is, errors that were caught and avoided during the use of the system 10), surgery type and laterality, surgical outcomes, surgical complications, patient demographics, geographic information, as well as the date, time, location and personnel associated with each interaction or use of the system 10 for efficiency and accountability.

Diagnostic analytics represent the next level of analytics and generally involve parsing the descriptive analytic data gathered by the system 10 to try to determine why a specific event (for example a "near miss" event) happened. Discovery analytics look beyond the why to determine what can be learned from the data collected. For example, discovery analytics can be used to look for trends in data associated with a particular surgical teams, hospitals, geographic areas, healthcare systems, and/or procedures. Predictive analytics builds on discovery analytics to determine what is likely to happen in the future given what has actually occurred in the past. For example, by analyzing past trends and/or events attributed to an individual contributor, team, site, or geospatial level, perhaps one can proactively alarm on probabilities for contributing events to wrong site surgery and/or other medical errors.

Finally, prescriptive analytics takes all the prior analytic information into account to help determine specific course of action to limit or prevent wrong site surgery events and/or other medical errors. For example, based upon data previously gathered and analyzed, one could identify teams or individuals that could benefit from specific training modules, identify specific procedures that might have indicators to specific wrong side near-miss events, identify healthcare systems that may improve from additional process or communications steps, and/or identify to healthcare insurers at risk clients and areas where healthcare risk consulting may be beneficial. For example, analytics 48 based on "near miss" data may provide the hospital and/or insurers and/or quality improvement specialists valuable data as to where errors or possible errors may have occurred in order to drive remediation efforts to minimize or avoid such errors in the future. The analytics 48 may also be used to identify best practices based on the data collected, either within the hospital system ("intra-system") and/or amongst multiple different hospital systems ("inter-system"), and assessed to identify best practices for further reducing wrong-site surgery errors. These best practices (e.g. that eliminating shift changes during certain stages within the medical environment reduces near-misses) may be shared with the participating hospitals or surgery centers and implemented to further reduce the likelihood or chance of wrong-site surgeries.

Figure 95:
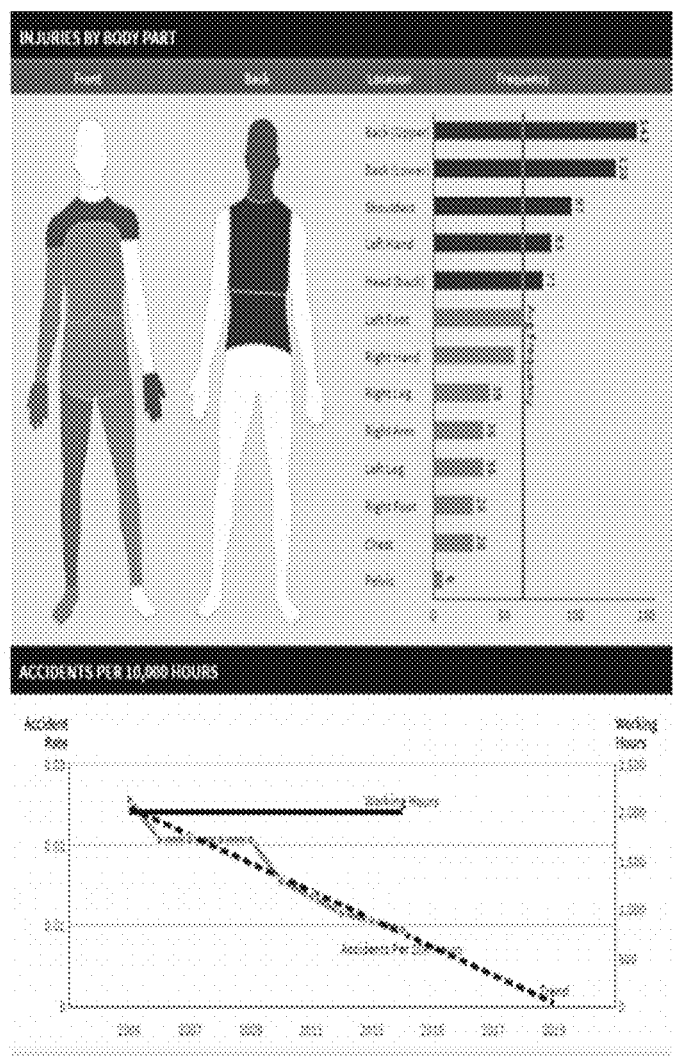
FIGS. 95-100 are various example diagrams illustrating the use of analytics with the wrong-site prevention system of FIG. 1.
Figure 96:
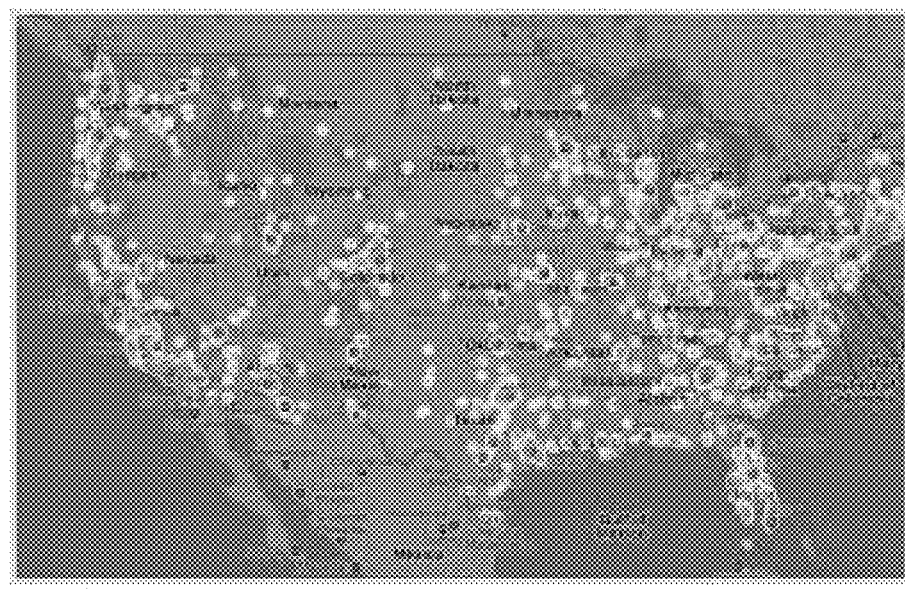
Figure 97:
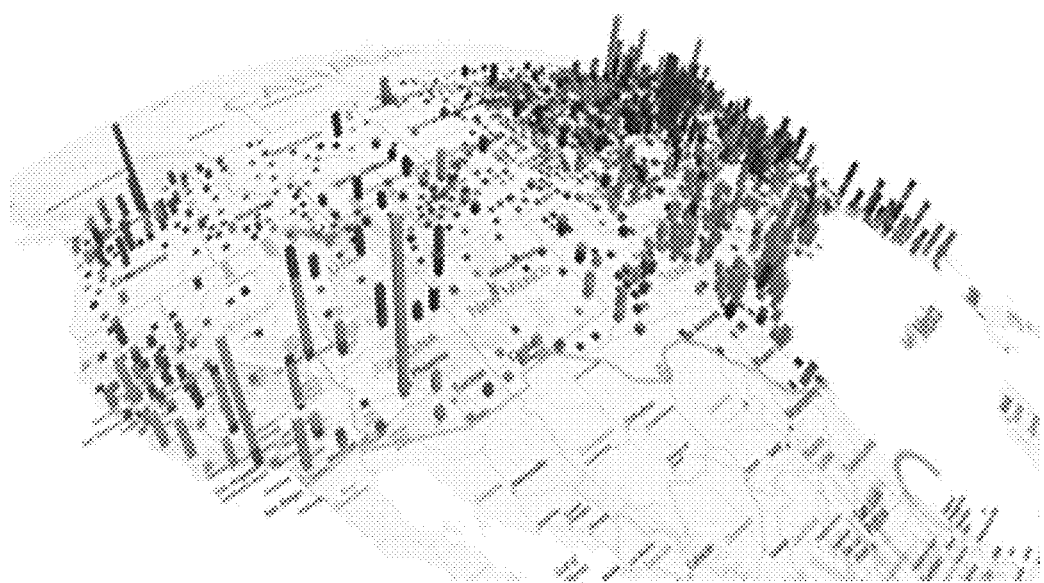
Figure 98:
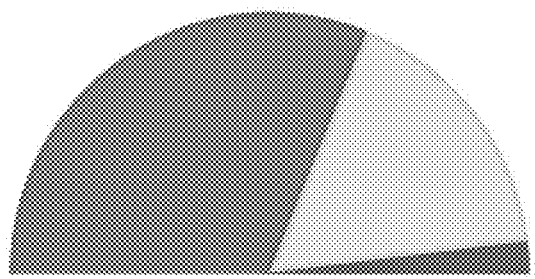
Figure 99:
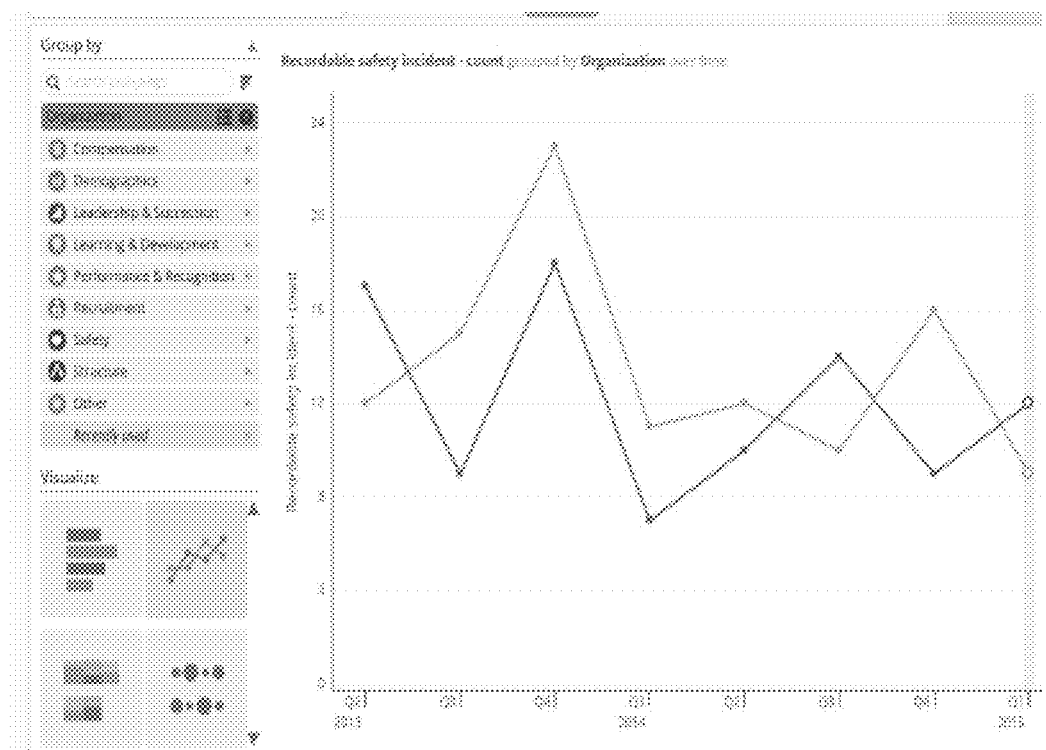
Figure 100:
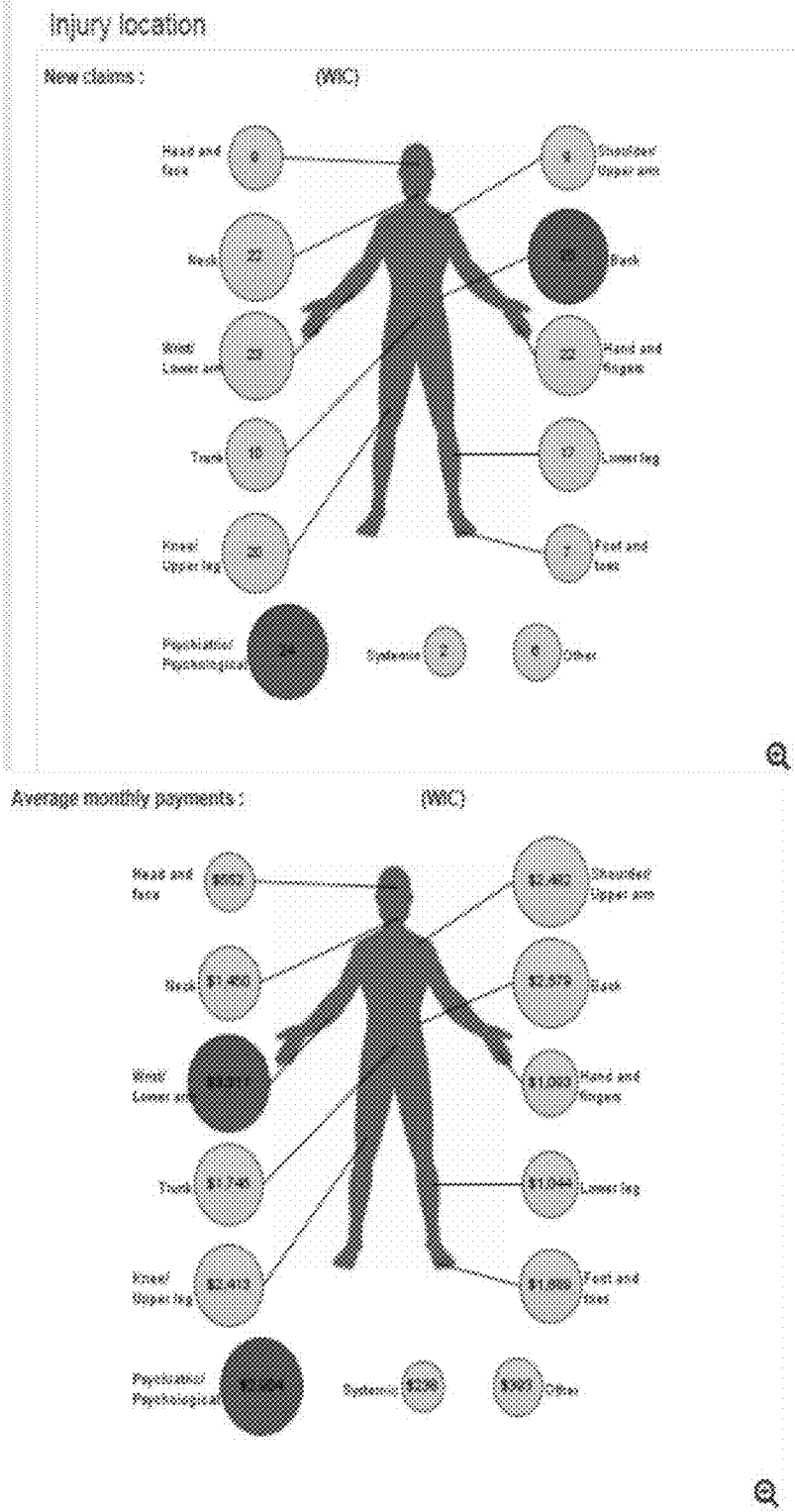

FIGS. 95-100 illustrate several examples of analytics that may be collected by the system 10 during use. FIG. 95 is one example of descriptive analytics (e.g. Injuries by body part) that presents frequency of injury data relative to an average frequency. FIG. 96 illustrates a map of the United Space and the geospatial occurrence of certain medical events. FIG. 97 is another map of the United States shown in perspective view, giving a more three dimensional view of occurrence of certain medical events, for example. This is an example of discovery analytics in which the analysts are looking for patterns or trends in the data from which they can draw conclusions. FIG. 98 is another example of descriptive analytics showing occurrence of near-miss data among otherwise successful surgical events for a particular week. FIG. 99 may be an example of Discovery analytics, where recordable safety incidents are grouped by organization, perhaps to look for trends in the data. FIG. 100 is another descriptive analytic that illustrates number of injuries by location, as well as some of the costs associated with each event.

Wrong Level Surgery Prevention

Certain surgeries (including but not limited to spine surgery) can be performed at more than one level or location within a particular organ, structure or region of the patient's anatomy, which can create challenges for the surgeon to correctly identify the level of the intended surgery. According to one aspect of the disclosure, the system of preventing wrong-site surgeries and blade-related injuries 10 may include a correct site verification process that extends beyond the "Timeout Recorded" step (e.g. Step 62 of FIG. 63) and may be performed before and/or after the time-out is conducted by the surgeon.

In spine surgery, for example, the risk of wrong site surgery, and in particular wrong level surgery continues even after the final time out checks have been completed and verified. In part due to the repetitive vertebral structure of the spine, a surgeon may not always be able recognize if, for example, the operative window has shifted a level for whatever reason. It is not uncommon for surgeons in spine procedures to use intraoperative fluoroscopic imaging to verify details such as for example the positioning of spinal implants, surgical approach angles, and the like. The system of preventing wrong-site surgeries and blade-related injuries 10 described herein enables the surgeon to intraoperatively verify the location of the affected spinal level to help avoid a wrong level event.

Figure 101:
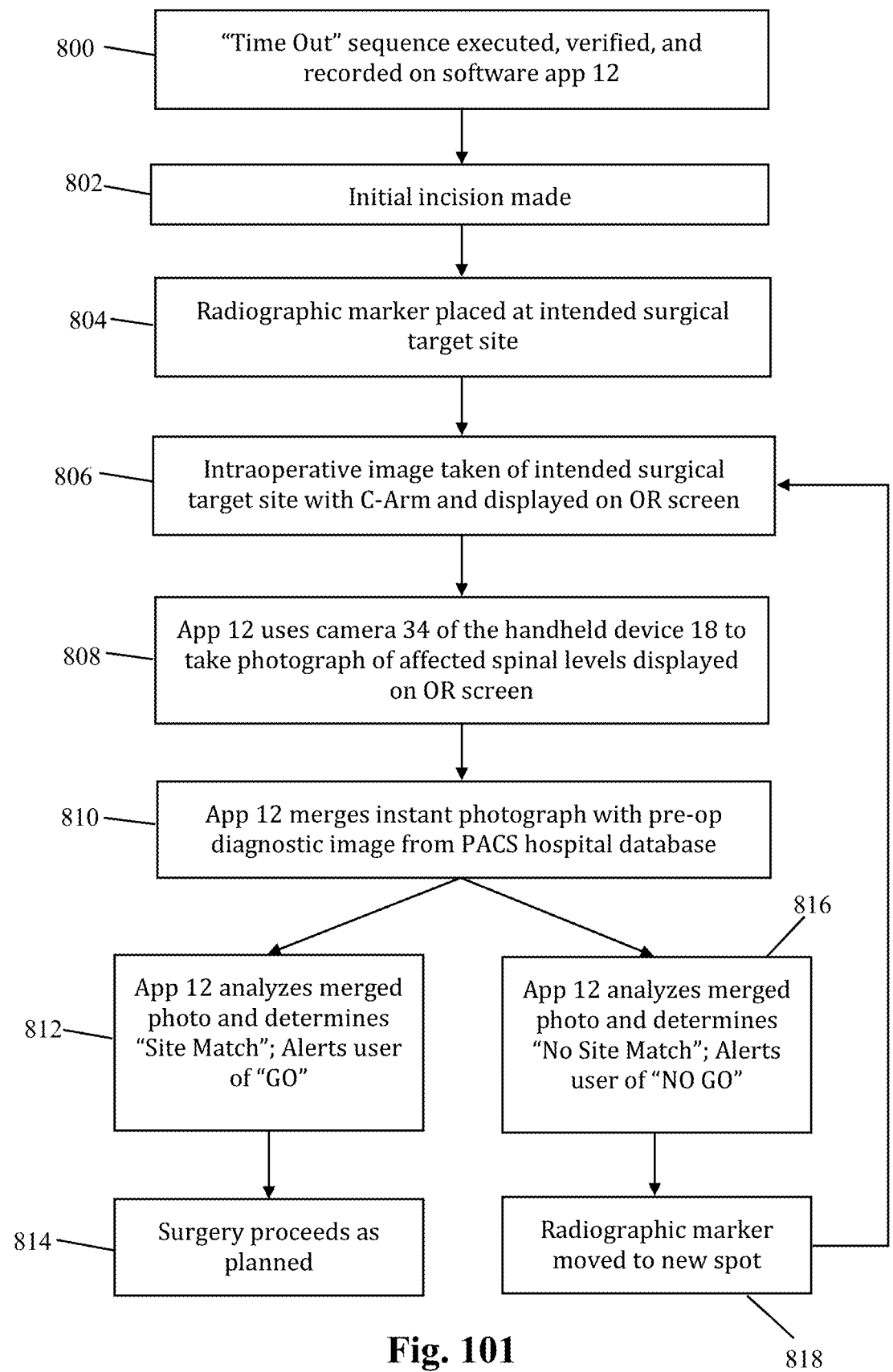
FIG. 101 is flow chart describing example method steps of preventing wrong-level surgeries (in spine surgery, by way of example only) which may form an optional part of the wrong-site surgery prevention system and method of the present disclosure.

FIG. 101 illustrates a flowchart depicting the steps of an exemplary method of using the system of preventing wrong-site surgeries and blade-related injuries 10 during a spine surgery to prevent wrong level surgeries. In step 800, the "time out" sequence of the instant example is executed, verified, and recorded within the App. This allows the procedure to commence and the initial incision 802 is made. After exposure has been established to the intended spinal level, a radiographic marker 804 is placed at the intended surgical site. In the next step 806, an intraoperative image is taken of the intended surgical site, for example using a C-Arm. This image is customarily displayed on a screen in the OR. The user would then use the camera 34 (FIG. 62) of the handheld device 18 operating the system of preventing wrong-site surgeries and blade-related injuries 10 via the software application 12 to take at least one photograph of the affected spinal levels (Step 808) displayed on the screen. The software application 12 then compares via merge or overlay (Step 810) the photograph recently attained of the intended site with a pre-op diagnostic image located in the PACS hospital database. If the system of preventing wrong-site surgeries and blade-related injuries 10 indicates that there is a site match (step 812), the user may tap a "Go" button to confirm this verification and proceed with the surgery as intended (Step 814). If, however, the system of preventing wrong-site surgeries and blade-related injuries 10 determines that the photographs do not match (step 816), a No Go message is generated and the surgeon may be prompted to move the marker and re-image (step 818). This sequence may be repeated as many times as necessary to obtain a site match verification in step 812.

In some instances, the system of preventing wrong-site surgeries and blade-related injuries 10 includes an image-comparison correct site verification process that could be performed prior to the "Timeout Recorded" step (e.g. Step 62 of FIG. 63). For example, the correct level could be determined using pre-op images that are based on an existing marker from a previous surgical procedure in the same or close location. In a spine patient, for example, existing markers could include any implanted hardware (e.g. screws, rods, implants, interspinous spacers, and the like). In a prostate patient, an example of existing marker would be radiographic beads previously implanted. The software application 12 then compares via merge or overlay the image of the intended site from the prior surgery with a pre-op diagnostic image located in the PACS hospital database. If there is a match, then the surgeon can confirm the location of the target level relative to the marker prior to initial incision.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A safety-blade dispenser for use in a surgical procedure, comprising:
 a housing unit sized and configured for holding in a single user's hand, the housing unit having a perimeter defined by first and second opposing panels, first and second opposing ends, and first and second opposing sides, the housing unit further including an interior cavity within the perimeter, the first end including at least one aperture formed therein for dispensing a surgical sharp for use in surgery, and the second end including at least one aperture formed therein for receiving a used surgical sharp after use in surgery;
 a plurality of surgical blade holder assemblies, each surgical blade holder assembly adapted to releasably hold a respective surgical sharp, the at least one surgical blade holder assembly slideably positioned within said interior cavity and moveable between a first position in which the surgical sharp is fully contained within said interior cavity to a second position in which a portion of said surgical sharp protrudes through said at least one aperture formed in the first end; and
 a blade removal assembly comprising the at least one aperture formed in the second end and a flexible element, the at least one aperture formed in the second end extending into the interior cavity, and the flexible element being adapted to releasably pinch a portion of said used surgical sharp in the at least one aperture formed in the second end.

2. The safety-blade dispenser of claim 1, wherein the flexible element is moveable between a released position in which the portion of said used surgical sharp is received within said interior cavity to a compressed position in which the portion of said used surgical sharp is pinched in the at least one aperture formed in the second end.

3. The safety-blade dispenser of claim 1, wherein the flexible element is an integral part of one of the first or second opposing panels of the housing.

4. The safety-blade dispenser of claim 1, wherein said first and second sides include scalloped edges.

5. The safety-blade dispenser of claim 1, wherein the plurality of surgical blade holder assemblies are positioned side by side.

6. The safety-blade dispenser of claim 1, wherein said surgical sharp is a surgical blade having a leading end comprising a blade portion and a trailing end comprising a connector portion.

7. The safety-blade dispenser of claim 6, wherein said surgical blade is positioned within said at least one surgical blade holder assembly such that said trailing end protrudes from said housing unit when said at least one surgical blade holder assembly is in said second position.

8. The safety-blade dispenser of claim 1, wherein said surgical sharp is a surgical blade that includes a handle.

9. The safety-blade dispenser of claim 8, wherein said surgical blade and said handle are positioned within said housing unit such that a portion of said handle protrudes from said housing unit when said at least one surgical blade holder assembly is in said second position.

10. The safety-blade dispenser of claim 1, further comprising a confirmation label removably attached to the housing unit, the confirmation label positioned such that movement of the at least one surgical blade holder assembly is prevented while the confirmation label is attached to the housing unit.

11. The safety-blade dispenser of claim 10, wherein a portion of the confirmation label covers at least a portion of the first panel, a portion of the second panel, and a portion of the first end of the housing.

12. The safety-blade dispenser of claim 10, wherein the confirmation label includes electronically scannable code, the electronically scannable code containing at least one of patient information and surgical procedure information.

13. The safety-blade dispenser of claim 12, wherein the electronically scannable code is one of a QR code and a bar code.

14. The safety-blade dispenser of claim 10, wherein the confirmation label includes at least one visual indicator conveying to a user the laterality of the surgical procedure.

15. The safety-blade dispenser of claim 14, wherein the at least one visual indicator includes at least one of words and color.

16. The safety-blade dispenser of claim 12, further comprising a packaging assembly adapted to receive the safety-blade dispenser prior to the surgical procedure.

17. The safety-blade dispenser of claim 16, wherein said packaging assembly comprises a first transparent sterile pouch, a second transparent sterile pouch, and a non-sterile outer container.

18. The safety-blade dispenser of claim 17, wherein said safety-blade dispenser is sealed within said first transparent sterile pouch, which is sealed within said second transparent sterile pouch, which is placed within said non-sterile outer container.

19. The safety-blade dispenser of claim 18, wherein said non-sterile outer container includes a transparent window.

20. The safety-blade dispenser of claim 19, wherein said safety-blade dispenser is placed within said packaging assembly such that said electronically scannable code is scannable through said first transparent sterile pouch, said second transparent sterile pouch, and said transparent window while contained within said packaging assembly.

\* \* \* \* \*